(12) United States Patent
Huang et al.

(10) Patent No.: US 7,563,567 B1
(45) Date of Patent: Jul. 21, 2009

(54) USE OF ECIST MICROARRAYS IN AN INTEGRATED METHOD FOR ASSESSING DNA METHYLATION, GENE EXPRESSION AND HISTONE ACETYLATION

(75) Inventors: Tim Hui-Ming Huang, Columbia, MO (US); Huidong Shi, Columbia, MO (US)

(73) Assignee: The Curators of the Univeristy of Missouri of Columbia, Columbia, MO (US)

( * ) Notice: Subject to any disclaimer, the term of this patent is extended or adjusted under 35 U.S.C. 154(b) by 445 days.

(21) Appl. No.: 10/414,540

(22) Filed: Apr. 14, 2003

Related U.S. Application Data

(60) Provisional application No. 60/372,140, filed on Apr. 12, 2002.

(51) Int. Cl.
C12Q 1/68 (2006.01)
C12P 19/34 (2006.01)
C07H 21/04 (2006.01)

(52) U.S. Cl. .................. 435/6; 435/91.2; 536/24.31; 536/24.32; 536/24.33

(58) Field of Classification Search .................. 435/6, 435/91.2; 536/24.31, 24.32
See application file for complete search history.

(56) References Cited

U.S. PATENT DOCUMENTS

| | | | |
|---|---|---|---|
| 4,682,195 A | 7/1987 | Yilmaz | |
| 4,683,202 A | 7/1987 | Mullis | |
| 4,800,159 A | 1/1989 | Mullis et al. | |
| 5,143,854 A | 9/1992 | Pirrung | |
| 5,589,339 A | 12/1996 | Hampson et al. | |
| 5,591,575 A | 1/1997 | Hampson et al. | |
| 5,665,549 A * | 9/1997 | Pinkel et al. .................. | 435/6 |
| 5,786,146 A | 7/1998 | Herman et al. | |
| 5,858,659 A | 1/1999 | Sapolsky et al. | |
| 5,871,917 A | 2/1999 | Duffy | |
| 6,045,994 A | 4/2000 | Zabeau et al. | |
| 6,251,601 B1 * | 6/2001 | Bao et al. .................. | 435/6 |
| 6,262,116 B1 * | 7/2001 | Pandolfi et al. .............. | 514/557 |
| 6,300,071 B1 | 10/2001 | Vuylsteke et al. | |
| 6,605,432 B1 | 8/2003 | Huang | |
| 6,884,597 B1 * | 4/2005 | Taya et al. .................. | 435/7.92 |
| 2003/0129602 A1 | 7/2003 | Huang | |

FOREIGN PATENT DOCUMENTS

| WO | WO 00/26401 | 5/2000 |
|---|---|---|
| WO | WO/03087774 | 10/2003 |

OTHER PUBLICATIONS

Yan et al. CPG island arrays: An application toward deciphering epigentic signatures of breast cancer. Clin Cancer Res., vol. 6, pp. 1432-1438, 2000.*
Cross et al. Purification of CpG islands using a methylated DNA binding column. Nature Genetics, vol. 6, pp. 236-244, 1994.*
Laird et al. DNA methylation and cancer. Human Molecular Genetics, vol. 3, pp. 1487-1495, 1994.*
Magdinier F et al. Regional methylation of the 5' end CpG island of BRAC1 is associated with reduced gene expression in human somatic cells. FASEB J. vol. 14, pp. 1585-1594, 2000.*
Adams et al. GeneCore; EST clone AA313068, Nature, 1995, 377 (6547, Supplement) 3-174.
Ahluwalia et al., "DNA Methylation and Ovarian Cancer," Gynecol. Oncol. 82:261-268, 2001.
Akopyants et al., "PCR-based Subtractive Hybridization and Differences in Gene Content Among Strains of *Helicobacter pylori*," Proc. Natl. Acad. Sci. USA 95:13108-13113, 1998.
Antequera, F., et al., "High Levels of De Novo Methylation and Altered Chromatin Structure at CpG Islands in Cell Lines," Cell 2:503-514, 1990.
Baylin et al., "Alterations in DNA Methylation: A Fundamental Aspect of Neoplasia," Advances in Cancer Research, pp. 140-196, 1998.
Baylin, Stephen B., "Tying it all Together: Epigenetics, Genetics, Cell Cycle, and Cancer," Science 277:1948-1949, 1997.
Belinsky et al., "Aberrant Methylation of $p16^{INK4a}$ is an Early Event in Lung Cancer and a Potential Biomarker for Early Diagnosis," Proc. Natl. Acad. Sci. USA 94:11891-11896, 1998.
Belinsky et al., "Increased Cytosine DNA-methyltransferase Activity is Target-cell-specific and an Early Event in Lung Cancer," Proc. Natl. Acad. Sci. USA 94:4045-4050, 1996.
Bloom, H.J.G. and Richardson, W.W., "Histological Grading and Prognosis in Breast Cancer," British Journal of Cancer 11:359-377, 1957.
Brandeis, M. et al., "Sp1 Elements Protect a CpG Island from *de novo* Methylation," Nature 371:435-438, 1994.
Carotti et al., "Influence of Pre-existing Methylation on the de Novo Activity of Eukaryotic DNA Methyltransferase," Biochem. J. 37:1101-1108, 1998.

(Continued)

*Primary Examiner*—Suryaprabha Chunduru
(74) *Attorney, Agent, or Firm*—Barry L. Davison; Davis Wright Tremaine LLP

(57) ABSTRACT

Novel methods are herein provided for high-throughput, dual analysis of DNA methylation and gene expression, and triple analysis of DNA methylation, gene expression and gene-associated histone acetylation in cancer cells using arrayed expressed CpG island sequence tags (ECISTs). ECISTs correspond to genomic DNA fragments comprising GC-rich segments along with promoter and/or exon (e.g., first exon) portions of genes. The GC-rich segments are useful for screening hypermethylated CpG sites in cancer cells, while the corresponding promoter and exon-containing portions are useful for determining corresponding transcript levels and assessing histone acetylation. Also provided are high-throughput methods for either confirming methylation-dependent gene silencing, or identifying therapeutically effective demethylating agents, using the ECIST array panels to identify hypermethylated loci, and measure expression levels thereof after cellular exposure to demethylating agents. Further provided are high-throughput methods for distinguishing between direct (primary) demethylation-dependent gene up-regulation, and indirect (secondary) demethylation-dependent up-regulation within apparent epigenetic cascades.

47 Claims, 19 Drawing Sheets

OTHER PUBLICATIONS

Christman et al., "5-Methyl-2'-deoxycytidine in single-stranded DNA can act in cis to Signal de novo DNA Methylation," Proc. Natl. Acad. Sci., USA 92:7347-7351, 1995.

Chuang et al., Human DNA-(Cytosine-5) Methyltransferase-PCNA Complex as a Target for $^{P21WAF1}$- Science 277:1996-2000, 1997.

Craig et al., "Removal of Repetitive Sequences from FISH Probes Using PCR-Assisted Affinity Chromatography," Hum. Genet. 100:472-476, 1997.

Cross et al. GeneCore; GenEmbl, clone HS13F74, Nature Genetics, 1994, 6(3):236-244.

Cross et al., "Purification of CpG Islands Using a Methylated DNA Binding Column," Nature Genet. 6:236-244, 1994.

Donini et al., "AFLP fingerprinting reveals pattern differences between template DNA extracted from different plant organs," Genome 40:521-526, 1997.

Frommer, M. et al., "A Genomic Sequencing Protocol that Yields a Positive Display of 5-Methylcytosine Residues in Individual DNA strands," Proc. Natl. Acad. Sci. USA 89:1827-1831, 1992.

Frudakis et al., GenCore; Geneseq, clone V 49815, WO97/25426, published Jul. 17, 1997.

Frudakis et al. GenCore; Geneseq, clone VX83369, WO97/25426, published Jul. 17, 1997.

Graff et al., "Mapping Patterns of CpG Island Methylation in Normal and Neoplastic Cells Implicates Both Upstream and Downstream Regions in de Novo Methylation," J. Biol. Chem. 272(35):22322-22329, 1997.

Herman et al., "Methylation-specific PCR: A Novel PCR Assay for Methylation Status of CpG Islands," Proc. Natl. Acad. Sci. USA 93:9821-9826, 1996.

Huang, T.H., et al., "Methylation Profiling of CpG Islands in Human Breast Cancer Cells," Human Molecular Genetics 8(3): 459-470, 1999.

Jackson-Grusby et al., "Loss of genomic methylation causes p53-dependent apoptosis and epigenetic deregulation," Nature Genetics 27:31-39, 2001.

Jones, P.A., "DNA Methylation Errors and Cancer," Cancer Res. 56:2463-2467, 1996.

Karpf et al., "Inhibition of DNA methyltransferase stimulates the expression of signal transducer and activator of transcription 1, 2, and 3 genes in colon tumor cells," Proc. Natl. Acad. Sci. 96(24):14007-14012, 1999.

LaFranchi et al., GenCore; EST, clone F16311, Genome Research, 1996, 6(1):35-42.

Laird et al., "DNA Methylation and Cancer," Hum. Mol. Genet. 3:1487-1495, 1994.

Lee J.H. and Welch D.R., "Identification of Highly Expressed Genes in Metastasis-Suppressed Chromosome 6/Human Malignant Melanoma Hybrid Cells Using Subtractive Hybridization and Differential Display," Int. J. Cancer. 71:1035-1044, 1997.

Li et al., "Role for DNA Methylation in Genomic Imprinting," Nature 366:263-265, 1993.

Mummaneni, P., et al., "Epigenetic Gene Inactivation Induced by a Cis-acting Methylation Center," J. Biol. Chem. 270 (2): 788-792, 1995.

Pan, GenCore, Genseq, clone X22302, WO99/06426, published Feb. 11, 1999.

Pfeifer, G.P., et al., "Polymerase Chain Reaction-Aided Genomic Sequencing of an X Chromosome-linked CpG Island: Methylation Patterns Suggest Clonal Inheritance, CpG Site Autonomy, and an Explanation of Activity State Stability," Proc. Natl. Acad. Sci. USA 87:8252-8256, 1990.

Saiki et al., "Primer-Directed Enzymatic Amplification of DNA with a Thermostable DNA Polymerase," Science 239:487-491, 1988.

Schena et al., "Quantitative Monitoring of Gene Expression Patterns with a Complementary DNA Microarray," Science, 270:467-470, 1995.

Singer-Sam, J. and Riggs, A.D., "X-Chromosone Inactivation and DNA Methylation," DNA Methylation: Molecular Biology and Biological Significance, pp. 358-384, 1993.

Tubby, GeneCore; Geneseq, clone HS29K1, Dec. 18, 1997.

Vertino et al., "De Novo Methylation of CpG Island Sequences in Human Fibroblasts Overexpressing DNA (Cytosine-5)—Methyltransferase," Mol. Cell Biol. 16:4555-4565, 1996.

Wu et al., "Expression of Prokaryotic Hhal DNA Methyltransferase is Transforming and Lethal to NIH 3T3 Cells," Cancer Res. 56:616-622, 1996.

Yan et al., "CpG Island Arrays: An Application toward Deciphering epigenetic Signatures of Breast Cancer," Clin. Cancer Res. 6:1432-1438 2000.

Yan et al., "Dissecting Complex epigenetic Alterations in Breast Cancer Using CpG Island Microarrays," Cancer Res. 61:8375-8380 2001.

Shi Huidong et al., ECIST (expressed CpG island sequence tag (microarrays for dual screening of DNA hypermethylation and gene silencing in cancer cells, Proc Amer Assn for Cancer Res Annual Meeting, vol. 43, Mar. 2002 p. 456 & 93$^{rd}$ Annual Meeting of the American Assn. for Cancer Res., San Francisco, CA USA Apr. 6-10, 2002.

Schena, M., Genome analysis with gene expression microarrays, BioEssays 18(5):427-431, 1996.

Duggan et al., Expression profiling using cDNA microarrays, Nature Genetics Suppl. 21:14, 1999.

Hanash et al., Integrating cancer genomics and proteomics in the post-genome era, Proteomics 2:69-75, 2002.

Model et al., Feature selection for DNA methylation based cancer classification, Bioinformatics, Oxford University Press, Oxford, GB, vol. 17, No. Suppl. 1, 2001, pp. 157-164.

\* cited by examiner

Figs. 9A and B

Figures 19A and B

Figures 20A, B, C and D

US 7,563,567 B1

USE OF ECIST MICROARRAYS IN AN INTEGRATED METHOD FOR ASSESSING DNA METHYLATION, GENE EXPRESSION AND HISTONE ACETYLATION

CROSS-REFERENCE TO RELATED APPLICATIONS

This patent application claims the benefit of priority to U.S. Provisional Patent Application Ser. No. 60/372,140, entitled "ECIST MICROARRAYS FOR DUAL SCREENING OF DNA HYPERMETHYLATION AND GENE SILENCING," filed on 12 Apr. 2002.

STATEMENT REGARDING SPONSORED RESEARCH

This work was supported in part by National Cancer Institute grant nos. CA-69065 and CA-84701 from the National Cancer Institute, and by grant DAMD17-98-1-8214 from the Army Medical Research Command. This work was also supported in part by National Cancer Institute grant CA-85289, and by Epigenomics, Inc. The United States Government has certain rights in this invention.

SEQUENCE LISTING

A Sequence Listing, pursuant to C.F.R. 37 1.52(e)(5), has been provided on compact disc (1 of 1) as a 1.66 MB file, entitled 40629-4.txt, and which is incorporated by reference herein in its entirety.

FIELD OF THE INVENTION

The present invention relates to novel high-throughput methods for dual analysis of DNA methylation and gene expression using expressed CpG island sequence tags. The present invention additionally relates to the identification of novel methylation-silenced genes that are reactivated upon demethylation, and to methods for determining the efficacy and mechanisms of demethylation action in cancer cells. The present invention further provides a novel integrated triple analysis microarray system to assess gene expression, DNA methylation, and histone acetylation in parallel. Further embodiments provide novel ECIST microarrays.

BACKGROUND

GC-rich DNA sequences are found within the promoter and first exon of approximately 50% of all genes in the human genome (Antequera & Bird, *Proc. Natl. Acad. Sci. USA*, 90:11995-11999, 1993). These sequences are known in the art as CpG islands. CpG islands can be targets of DNA methylation, an epigenetic phenomenon associated with altered chromatin structure and transcriptional repression (Rountree, M. R. et al., *Oncogene*, 20:3156-3165, 2001). Mammalian cells possess methylases that methylate cytosine residues on DNA that are 5' neighbors of guanine in CpG dinucleotides (CpG). Methylation occurs after cytosine has been incorporated into DNA in a process catalyzed by DNA methyltransferases ("Dnmts"), which transfer the methyl group from S-adenosylmethionine to the 5'-position of the pyrimidine ring in, characteristically but not exclusively, the context of the palindromic CpG dinucleotide (Ramsahoye et al., 2000). 5-Methylcytosine is asymmetrically distributed in the genome and is most commonly found in CpG-poor regions, since most CpG islands in somatic cells remain methylation-free, except for the promoters of imprinted genes and genes on the inactive X-chromosome (Bird et al., 1985) where methylation of 5' regulatory regions can lead to transcriptional repression.

Thus, in normal cells, CpG island methylation plays an important role in regulating gene expression in a developmentally significant and tissue-specific manner (Jones & Takai, *Science*, 293:1068-1070, 2001). In cancer cells, however, aberrant methylation (typically hyper-methylation) of CpG islands has been found in the 5'-end of the regulatory region of many tumor-suppressor genes and of genes responsible for genomic stability (Esteller, M. et al., *Cancer Res.*, 61:3225-3229, 2001; Baylin, S. B. et al., *Hum. Mol. Genet.*, 10:687-692, 2001; Jones & Laird, *Nat. Genet.*, 21:163-167, 1999). Current data is consistent with a causal link between his type of epigenetic control and tumor development (Jones & Laird, 1999). Accordingly, critical tumor-suppressor and stability genes are silenced, leading to clonal proliferation of tumor cells (e.g., Id).

Thus, hypermethylated CpG islands that can be associated with gene silencing provide at least potential markers for novel genes that are subject to epigenetic control, and thereby have potential important diagnostic and prognostic utility. However, efficient identification in such associated cases of a direct or primary (causative) association of methylation and gene silencing is problematic, because many genes participating in cell-cycle control, growth factor/receptor signaling, and mobilization of retroelements appear to be generally up-regulated in a demethylated cellular state (Jackson-Grusby, L. et al., *Nat. Genet.*, 27:31-39, 2001), and such regulation is likely to be secondary, or indirectly related to CpG-island methylation as part of a downstream, epigenetic expression cascade.

Therefore, prior art methylation assays, alone or in combination with prior art gene expression assay methods do not provide efficient and accurate methods for identification of novel direct associations between methylation and gene silencing. This is because divergent sets of reagents (e.g., methylation probes, and cDNA probes) would be required in independent assay procedures (e.g., methylation assays, and Northern blots or cDNA array screens), followed, if possible, by careful data correlation.

For example, there are various art-recognized assays for assessing the methylation state at particular CpG sequences, once the sequence region comprising them has been identified so that specific primers and/or probes can be constructed. Such assays include: DNA sequencing methods; Southern blotting methods; MethyLight™ (fluorescence-based real-time PCR technique described by Eads et al., *Cancer Res.* 59:2302-2306, 1999; U.S. Pat. No. 6,331,393); MS-SNuPE (Methylation-sensitive Single Nucleotide Primer Extension assay described by Gonzalgo & Jones, *Nucleic Acids Res.* 25:2529-2531, 1997; U.S. Pat. No. 6,251,594); MSP (Methylation-specific PCR assay described by Herman et al. *Proc. Natl. Acad. Sci. USA* 93:9821-9826, 1996; U.S. Pat. No. 5,786,146); and COBRA (Combined Bisulfite Restriction Analysis methylation assay described by Xiong & Laird, *Nucleic Acids Res.* 25:2532-2534, 1997).

Likewise, assays for the discovery of novel differentially methylated CpG sequences, while less numerous, include such methods as: restriction landmark genomic scanning ("RLGS"; Eng et al., *Nature Genetics* 25:101-102, 2000; Costello et al., *Nature Genetics* 25:132-138, 2000; Zhu et al., *Proc. Natl. Acad. Sci.* USA 96:8058-8063, 1999); RLGS in combination with virtual genome scans ("VGS"; Rouillard et al., *Genome Research* 11:1453-1459, 2001); methylated CpG island amplification ("MCA"; Toyota et al., *Cancer Res.*

59:2307-2312, 1999; WO 00/26401A1); arbitrarily primed-polymerase chain reaction ("AP-PCR"; Liang et al., *Genomics* 53:260-268, 1998); and differential methylation hybridization ("DMH"; Yan et al., *Clin. Canc. Res.* 6:1432-1438, 2000).

Restriction Landmark Genomic Scanning. Restriction landmark genomic scanning ("RLGS") approaches have been employed to identify sequences and regions of differential methylation, and regions so-identified have been cloned and sequenced. RLGS methods take advantage of the fact that specific DNA cleavage by particular restriction enyzmes, such as NotI is methylation sensitive. Moreover, NotI has a CG-rich octanucleotide recognition motif, and cleaves predominantly in CpG-rich "islands." Thus, digestion of genomic DNA with NotI and end-labeling of the NotI staggered ends, followed by further restriction digestion (e.g., with 5-base and/or 6-base recognition sequence enzymes) in combination with 2-dimensional electrophoresis has been used to generate resolved patterns of CpG-island-related fragments having at least one labeled NotI end. Such patterns can be used to compare the methylation status among various genomic DNA samples, and if a particular NotI site is methylated in a test genomic DNA sample, relative to that in normal genomic DNA, no corresponding end labeled fragment(s) will be visible in the RLGS pattern of the test sample (corresponding 'spot disappearance,' or absence). Boundary libraries (e.g., of NotI-EcoRV fragments) can be used to obtain cloned DNA corresponding to such regions.

Significantly, however, such prior art RLGS methods for detection of CpG methylation are limited, inter alia, by: (i) the use of only particular methylation-sensitive restriction enzymes, which effectively limits analyses to CpG sequences within CpG island regions; (ii) dependence (for detection) upon NotI end-labeling (or the equivalent); and (iii) upon the disappearance of (more accurately, the absence of) a test DNA spot (i.e., where a particular NotI site in a test DNA sample is methylated and therefore not cleaved by NotI digestion) relative to a corresponding spot present in the normal (test) DNA 2-dimensional pattern. Moreover, RLGS methods reveal nothing about gene expression, and therefore nothing about methylation-dependent gene silencing.

Virtual Genome Scans. Virtual genome scans (VGS) provide methods for use in conjunction with RGLS methods to identify fragments of interest displayed in RLGS scans. Informatics tools are used, in conjunction with known human genome sequence information, to produce virtual scans, for example, with NotI and EcoRV (as first-dimension RLGS restriction enzymes), and, for example, HinfI or DpnII (as second-dimension enzymes). The size of the expected NotI-EcoRV and NotI-NotI fragments (if no intervening EcoRV site is present) are computed, along with the second-dimension fragments, based on the HinfI or DpnII site nearest to a particular NotI site (Rouillard et al. *Genome Research* 11:1453-1459, 2001). Thus, identification of RLGS sequences can be made without the use of boundary libraries.

However, the method still depends on determining the differences between two samples using RLGS, and is thus subject to most of the limitations thereof. Moreover, as for RLGS, VGS reveals nothing about gene expression or methylation-dependent gene silencing.

Methylated CpG Island Amplification. Methylated CpG island amplification ("MCA") is a PCR-based technique for rapid enrichment of hypermethylated CG-rich regions, that requires the sequential digestion by a particular methylation sensitive, methylation insensitive isoschizomeric enzyme pair (i.e., SmaI and XmaI, respectively), followed by PCR amplification based on primers that specifically hybridize to adapters ligated to the staggered XmaI ends. Additionally, the restriction sites must be closely situated (<1 kb apart).

Thus, as in the case of prior art RLGS applications, the method is primarily limited to particular CpG sequences within CpG-rich genomic regions (Toyota et al., *Cancer Res.* 59:2307-2312, 1999). Additionally, the technique is sensitive to artifacts relating to incomplete digestion with SmaI, the methylation sensitive restriction enzyme. The technique can be combined, in a more complex multistep method with substractive hybridization (RDA; representational difference analysis) to obtain cloned fragments enriched for hypermethylated sequences (Id). Nonetheless, as for RLGS and VGS methods, MCA reveals nothing about gene expression or methylation-dependent gene silencing.

Methylation-Sensitive Arbitrarily Primed PCR. Likewise, methylation-sensitive arbitrarily primed-polymerase chain reaction ("AP-PCR") is a PCR-based technique for rapid enrichment of hypermethylated CG-rich regions, that involves co-digestion of DNA with a methylation-insensitive enzyme (e.g., RsaI) to generally reduce the size of DNA fragments, plus, in separate reactions, a methylation-sensitive member, and a methylation-insensitive member of a isoschizomeric enzyme pair (e.g., RsaI plus HpaII, and RsaI plus MspI, respectively), followed by PCR amplification using one or more specific oligonucleotide primers. In this case, no PCR products are produced if the region between two primer sites contains an unmethylated HpaII (CCGG) sequence. Digestion of the DNA with RsaI only, and with RsaI and MspI serve as controls for determining whether bands observed in the AP-PCR of RsaI- plus HpaII-digested DNA are actually due to differential methylation of CCGG sequences within the region of amplification (Conzalgo et al., *Cancer Research* 57:594-599).

Thus, methylation-sensitive AP-PCR methods are limited commensurate with primer choice, and as for RLGS and MCA described above, are primarily biased toward CpG island regions, especially when extensively CG-rich primer sequences are employed (Liang et al., *Genomics* 53:260-268, 1998). Generally, methylation-sensitive AP-PCR is subject to many of the same artifacts that limit the effectiveness of MCA methods, such as incomplete digestion by restriction enzymes, and distance between primer sites. Moreover as for RLGS, VGS, and MCA, AP-PCR reveals nothing about gene expression or methylation-dependent gene silencing.

Differential Methylation Hybridization. Differential methylation hybridization ("DMH") is an array-based method involving differential probing of arrayed CpG-rich tags (e.g., from a CpG island genomic library) with amplicons from reference, or, e.g., tumor DNA samples (Huang, T. H.-M. et al., *Hum. Mol. Genet.*, 8:459-470, 1999; see also applicant's U.S. Ser. No. 09/497,855, filed 4 Feb. 2000, Notice of Allowance received 7 Mar. 2003, and incorporated by reference herein in its entirety). The differences in tumor and reference signal intensities on the tested CpG island arrays reflect methylation alterations of corresponding sequences in the tumor DNA (Yan et al., *Clin. Canc. Res.* 6:1432-1438, 2000). Using a panel of CpG island tags arrayed on solid supports, DMH has been applied to identify hypermethylated genes in breast and ovarian cancer (Yan, P. S., et al., *Clin. Cancer Res.*, 6:1432-1438, 2000; Ahluwalia, A. et al., *Gynecol. Oncol.*, 82:261-268, 2001).

To produce DMH amplicons, the DNA is digested to produce small (e.g., about 200 bp) DNA fragments while preserving CpG islands (e.g., by digestion with MseI, which recognizes TTAA). Linkers are ligated to the fragment ends, and the fragments are digested with a methylation-sensitive enzyme, e.g., BstUI (77% of known CpG islands contain BstUI sites), prior to filling in the protruding linker ends and PCR amplification using linker primers. Fragments cleaved by the methylation-sensitive enzyme are rendered non-amplifiable by the linker primers, so that the amplified fragment pool is enriched for methylated amplicons.

DMF is thus favorably distinguished from other prior art methods as a high-throughput method for the analysis of CpG-rich genomic DNA regions. Currently, however, DMH is limited by the fact that only about 2% of the total genomic CpG island regions are represented in the available arrayed panels (Id). Moreover, as for all the prior art methods discussed above, including RLGS, VGS, MCA, and AP-PCR, the DMH protocol alone reveals nothing about gene expression and methylation-dependent gene silencing.

Demethylating Drugs and Gene Expression Assays. DNA methylation is unique in that it is a mechanism for modifying the base sequence of DNA without altering its coding, and because it is a heritable reversible epigenetic change. Currently, therefore, there is renewed enthusiasm for administration of demethylating drugs in cancer treatment (Santini, V., et al., *Ann. Intl. Med.,* 134:573-86, 2001). Effective demethylating treatments, however, will require an understanding of how particular genes respond to particular demethylating agents in cancer cells. Specifically, as discussed above in relation to methylation assays and gene silencing, expression assays are needed, along with a method to efficiently correlate gene expression with gene methylation state.

Prior art gene expression assay methods include Northern blotting methods, RT-PCR-based methods, and cDNA-based screening methods. However, prior art expression assays reveal absolutely nothing about the methylation status of the subject genes, and significantly fail to distinguish between direct and indirect epigenetic effects. For example, cDNA microarrays have been applied to determine global profiles of gene expression in demethylated cells (Karpf, A. R. et al., *Proc. Natl. Acad. Sci. USA,* 96:14007-14012, 1999; Jackson-Grusby, L. et al., *Nat. Genet.,* 27:31-39, 2001). However, such assays reveal nothing about the methylation state of the subject genes, and as discussed above, many genes participating in cell-cycle control, growth factor/receptor signaling, and mobilization of retroelements appear to be secondarily regulated as part of a down-stream epigenetic cascade, or could be regulated in diseased cell states independent of methylation.

Therefore prior art DNA expression methods cannot themselves be used to differentiate between or among genes that directly respond (primary response) to demethylation, and those indirectly-(secondary response) or independently-regulated genes.

Likewise, while DMH and other prior art methylation assays have great potential for identification of differentially methylated CpG sequences, they do not in themselves provide for an efficient method for the determination of whether the particular sequences so identified, are sequences that are transcriptionally regulated by the identified differential methylation.

Therefore, there is a need in the art for novel high-throughput methods that serve not only to identify and validate genes with hypermethylated promoters in neoplasia and other diseases, but also to simultaneously measure gene expression and thereby enable efficient identification of genes that are relevant to tumorigenesis or other aberrant cell functions. There is a need in the art for novel methods that can be utilized to efficiently study the efficacy, and optimal dosages of various types of demethylating agents in cancer treatment regimens.

Repressed chromatin and gene silencing. Microarray approaches used to study functional DNA-protein interactions (e.g., Ren et al., *Science (Wash. DC)* 290:2306-2300, 2000; Weinmann et al., *Genes Dev.,* 16:235-244, 2002; and Suzuki et al., *Nature Genet.* 31:141-149, 2002) have revealed that many transcription regulators are linked to chromatin remodeling (Suzuki et al., *Nature Genet.* 31:141-149, 2002; and Cameron et al., *Nature Genet.* 21:103-107, 1999), placing this type of epigenetic change at the center of gene regulation. Specifically, repressed chromatin and gene silencing are associated with changes in DNA methylation and histone acetylation (Jones & Baylin, *Nature Rev. Genet.* 3:415-428, 2002), and these epigenomic modifications are widely recognized as a contributing factor in human tumorigenesis. Methylated DNAs at the 5'-end regulatory regions of genes recruit MBD (methyl-CpG binding domain) proteins, which are known to complex with histone deacetylases and other transcriptional corepressors (Ballestar & Esteller, *Carcinogenesis* 23:1102-1109, 2002). Deacetylation of lysine groups on histones 3 and 4 occurs via HDACs (histone deacetylases), resulting in a tighter interaction between negatively charged DNA and positively charged lysine and a closed, repressive chromatin configuration (Jones & Baylin, *Nature Rev. Genet.* 3:415-428, 2002; Ballestar & Esteller, *Carcinogenesis* 23:1102-1109, 2002). How repressive chromatin structures assemble onto DNA is not clear, but changes in methylation status of CpG islands in gene promoters presumably play a central role (Jones & Baylin, supra).

While DMH (differential methylation hybridization), as described above, is useful for screening CpG methylation and identifying loci susceptible to epigenetic modifications in various cancers, additional information is needed to characterize and elucidate the functional relationship between DNA methylation and histone acetylation in gene silencing.

There is a pronounced need in the art for a genomic microarray system for efficiently detecting changes in gene expression, DNA methylation and histone acetylation, and for distinguishing primary from secondary effects. There is a need in the art for such a genomic microarray system that is efficient therefore by virtue of that fact that all three of said parameters (gene expression, DNA methylation and histone acetylation) are assessed in parallel using a single microarray, or by using a plurality of the same microarray.

SUMMARY OF THE INVENTION

Particular embodiments of the present invention provide novel methods involving the use of arrayed expressed CpG island sequence tags ("ECISTs") for high-throughput dual analysis of CpG hypermethylation and gene expression (e.g., silencing) in cancer cells. According to such embodiments, GC-rich fragments of ECISTs are useful to screen aberrantly methylated CpG sites in cancer cells, while the exon-containing portions thereof are employed to measure levels of gene expression. ECIST array panels are thus used to simultaneously identify hypermethylated loci, and measure expression levels thereof to confirm methylation-associated gene silencing in breast cancer cell lines. This result shows that ECISTs are effective markers for identifying novel genes whose expression is silenced via CpG island hypermethylation.

In additional embodiments, ECIST microarrays are useful to study the efficacy, optimal doses, and types of demethylating agents in cancer treatment. In yet further embodiments, ECIST microarrays are also useful to reveal the sequence of events following demethylation treatments, and provide tools for elucidating the mechanisms of aberrant DNA methylation in the tumor genome. This inventive novel generation of microarray is useful to dissect the complex relationship between DNA methylation and gene expression in cancer. The inventive ECIST microarray is also useful to discover methylation-controlled genes during normal development, as well as novel imprinted genes responsible for certain genetic diseases.

In further embodiments, ECIST microarrays are useful in a novel integrated 'triple analysis' microarray system to assess gene expression, DNA methylation, and histone acetylation in parallel, and to dissect the complex hierarchy of epigenetic changes in cancer with respect to primary and secondary responses.

In a preferred embodiment, an integrated microarray panel comprising 1,507 short CpG island tags (ECISTs) located at the 5'-end gene regions (including the first exons) is used to assess effects of epigenetic treatments on cells, including for example, a human epithelial ovarian cancer cell line. The ECIST microarrays are useful used to analyze expression (e.g., up-regulation) of particular genes in response to treatment with either methylation (DAC) or deacetylation (TSA) inhibitors. Alternately, the ECIST microarrays are useful to assess the presence of absence of synergistic reactivation of more genes in response to combined DAC and TSA treatment versus either treatment alone. The ECIST microarrays are useful to assess the presence of either primary or secondary responses to the treatments, and thus identify/characterize genes either as methylation-dependent or -independent. According to the present invention, synergistic reactivation of the methylation-dependent genes by DAC plus TSA establishes the existence of a functional interaction between methylated promoters and deacetylated histones. Increased expression of some methylation-independent genes is associated with enhanced histone acetylation, whereas up-regulation of most identified genes, as characterized by the inventive triple analysis system, is due to events downstream of the epigenetic cascade. The inventive triple microarray system is useful in analyzing the dynamic relationship between transcription factors and promoter targets in cancer genomes.

The present invention provides a high-throughput method for assessing genomic CpG methylation and expression of genomic sequences of a tissue sample, comprising use of a single microarray, or replicates thereof, having a plurality of affixed CpG-rich genomic probe fragments each comprising an exon sequence or portion thereof of an expressible gene, to hybridize with CpG-rich genomic DNA-derived target sequences of a tissue sample and to mRNA-derived target sequences of the tissue sample, wherein the DNA-derived target sequences and the mRNA-derived target sequences are detectibly labeled, wherein the extent of said target hybridizations with each such represented expressible gene probe is reflective of the presence of methylated genomic CpG sequences and genomic expression, respectively, in the tissue sample, and whereby both genomic CpG methylation and genomic expression of particular expressible genes represented on the microarray, or replicates thereof, are, at least in part, assessed.

Preferably, the method further comprises hybridization of the single microarray, or replicates thereof, to CpG-rich genomic DNA-derived target sequences of a second tissue sample and to mRNA-derived target sequences of the second tissue sample, wherein the DNA-derived target sequences of the first and second tissue samples are distinguishably labeled and co-hybridized to the single microarray or replicates thereof, and wherein the mRNA-derived target sequences of the first and second tissue samples are distinguishably labeled and co-hybridized to the single microarray or replicates thereof, and whereby differences, between the tissue samples, in both genomic CpG methylation and genomic expression of particular expressible genes represented on the microarray, or replicates thereof, are, at least in part, assessed.

In preferred embodiments, the first and second tissue samples are different, and correspond to test and control tissue samples. Preferably, the test and control tissue samples correspond to cancer and normal tissue, respectively, and may correspond to the same tissue type.

In additional embodiments, the first and second tissue samples are identical, and the method further comprises treating of one of the tissue samples with a demethylating agent prior to preparing CpG-rich genomic DNA-derived target sequences and mRNA-derived target sequences from the treated tissue sample, whereby the effects of the agent on at least one of genomic CpG methylation or genomic expression of particular expressible genes represented on the microarray, or replicates thereof, is, at least in part, assessed, and whereby assessment of gene silencing is afforded. Preferably, the demethylating agent is or comprises 5-aza-2'-deoxycytidine.

Preferably, each of the plurality of affixed CpG-rich genomic probe fragments comprises part of a promoter and first exon of a gene. Preferably, each of the plurality of affixed CpG-rich genomic probe fragments comprises a CpG island sequence, or portion thereof. Preferably, each of the plurality of affixed CpG-rich genomic probe fragments comprises an expressed CpG island sequence tag (ECIST). Preferably, the plurality of affixed CpG-rich genomic probe fragments is derived from a CpG dinucleotide rich genomic library.

Preferably, the hybridizable CpG-rich genomic DNA-derived target sequences are prepared by a method comprising amplification of CpG-rich DNA fragments corresponding to genomic DNA sequences having one or more methylated CpG sequences. Preferably, hybridizable CpG-rich genomic DNA-derived target sequences are prepared by a method comprising use of a methylation-sensitive restriction enzyme. In preferred embodiments, preparation of the CpG-rich genomic DNA-derived target sequences and hybridization thereof to the microarray, or to replicates thereof, is performed according to the method of differential methylation hybridization (DMH), comprising the generation of target amplicons corresponding to methylated CpG island loci.

Preferably, preparation of the mRNA-derived target sequences comprises at least one of RNA ligase-mediated cDNA synthesis (RLCS), and RT-PCR. Preferably, microarray hybridization to the CpG-rich genomic DNA-derived target sequences and to the mRNA-derived target sequences is sequential, using a single microarray or replicates thereof. Alternately, microarray hybridization to the CpG-rich genomic DNA-derived target sequences and to the mRNA-derived target sequences is performed in parallel, using replicate microarrays.

In additional embodiments, the present invention provides a high-throughput method for assessing both genomic CpG methylation and expression of genomic sequences of a tissue sample, comprising:

obtaining, from a tissue sample, genomic DNA and preparing therefrom hybridizable CpG-rich genomic DNA-derived target sequences having a detectable label; obtaining, from the tissue sample, mRNA and preparing therefrom hybridizable mRNA-derived target sequences having a detectable label; hybridizing both the labeled DNA-derived target sequences and the labeled mRNA-derived target sequences to a single microarray, or replicates thereof, having a plurality of affixed CpG-rich genomic probe fragments each comprising an exon sequence or portion thereof of an expressible gene, and wherein the extent of said hybridizations with each such represented expressible gene probe is reflective of the presence of methylated genomic CpG sequences and genomic expression, respectively, in the tissue sample; and assessing, based at least in part on said hybridizations, both genomic CpG methylation and genomic expression of particular expressible genes represented on the microarray or replicates thereof.

In yet further embodiments, the present invention provides a method as described above, further comprising hybridization of the single microarray, or replicates thereof, to target sequences derived from acetylated histone-associated DNA of the target tissue, wherein the extent of said histone-associated target sequence hybridization with each represented expressible gene probe is reflective of the presence of gene-associated acetylated histones, and whereby at least one of genomic CpG methylation, genomic expression, or gene-associated acetylated histones of particular expressible genes represented on the microarray, or replicates thereof, is, at least in part, assessed.

Preferably, the method further comprises hybridization of the single microarray, or replicates thereof, to CpG-rich genomic DNA-derived target sequences of a second tissue sample, to mRNA-derived target sequences of the second tissue sample, and to target sequences derived from acetylated histone-associated DNA of the second target tissue, wherein the respective target sequences of the first and second tissue samples are distinguishably labeled and, in each case, co-hybridized to the single microarray or replicates thereof, and whereby differences, between the tissue samples, in at least one of genomic CpG methylation, genomic expression, or gene-associated histone acetylation of particular expressible genes represented on the microarray, or replicates thereof, is, at least in part, assessed.

In particularly preferred embodiments, the first and second tissue samples are identical, and the method further comprises treating of one of the tissue samples with at least one of a demethylating agent or an inhibitor of histone deacetylases prior to preparing mRNA-derived target sequences and target sequences derived from acetylated histone-associated DNA from the treated tissue sample, whereby the effects of the agents, alone or in combination, on at least one of genomic CpG methylation, genomic expression, or gene-associated histone acetylation of particular expressible genes represented on the microarray, or replicates thereof, is, at least in part, assessed, and whereby assessment of relationships between epigenetic events is afforded.

Preferably, the demethylating agent is or comprises 5-aza-2'-deoxycytidine, and the inhibitor of histone deacetylases is or comprises trichostatin A.

The present invention provides a microarray having a plurality of affixed CpG-rich genomic probe fragments each comprising an exon sequence or portion thereof of an expressible gene. Preferably, the plurality of affixed CpG-rich genomic probe fragments comprises part of a promoter and first exon of a gene. Preferably, the plurality of affixed CpG-rich genomic probe fragments comprises a CpG island sequence, or portion thereof. Preferably, the plurality of affixed CpG-rich genomic probe fragments comprises an expressed CpG island sequence tag (ECIST). Preferably, the plurality of affixed CpG-rich genomic probe fragments is derived from a CpG dinucleotide rich genomic library.

BRIEF DESCRIPTION OF THE DRAWINGS

FIG. 9A shows the initial screening, whereas FIG. 9B is the corresponding subarray of some of the hypermethylated clones (indicated on the initial array with reference X- and Y-coordinates of the subarray). PCR products of CpG island tags were dotted onto membranes hybridized first with radiolabeled normal amplicons. The same membranes, or duplicate membranes, were later hybridized with tumor amplicons. Each CpG island tag is represented with two parallel dots in order to differentiate specific hybridization signals from non-specific background signals, which generally appear as scattered single dots. Five to six sets of positive controls were dotted on the four corners of the arrays to serve as orientation markers and for comparison of hybridization signal intensities.

DETAILED DESCRIPTION OF THE INVENTION

Abbreviations and Definitions

Figure 1:
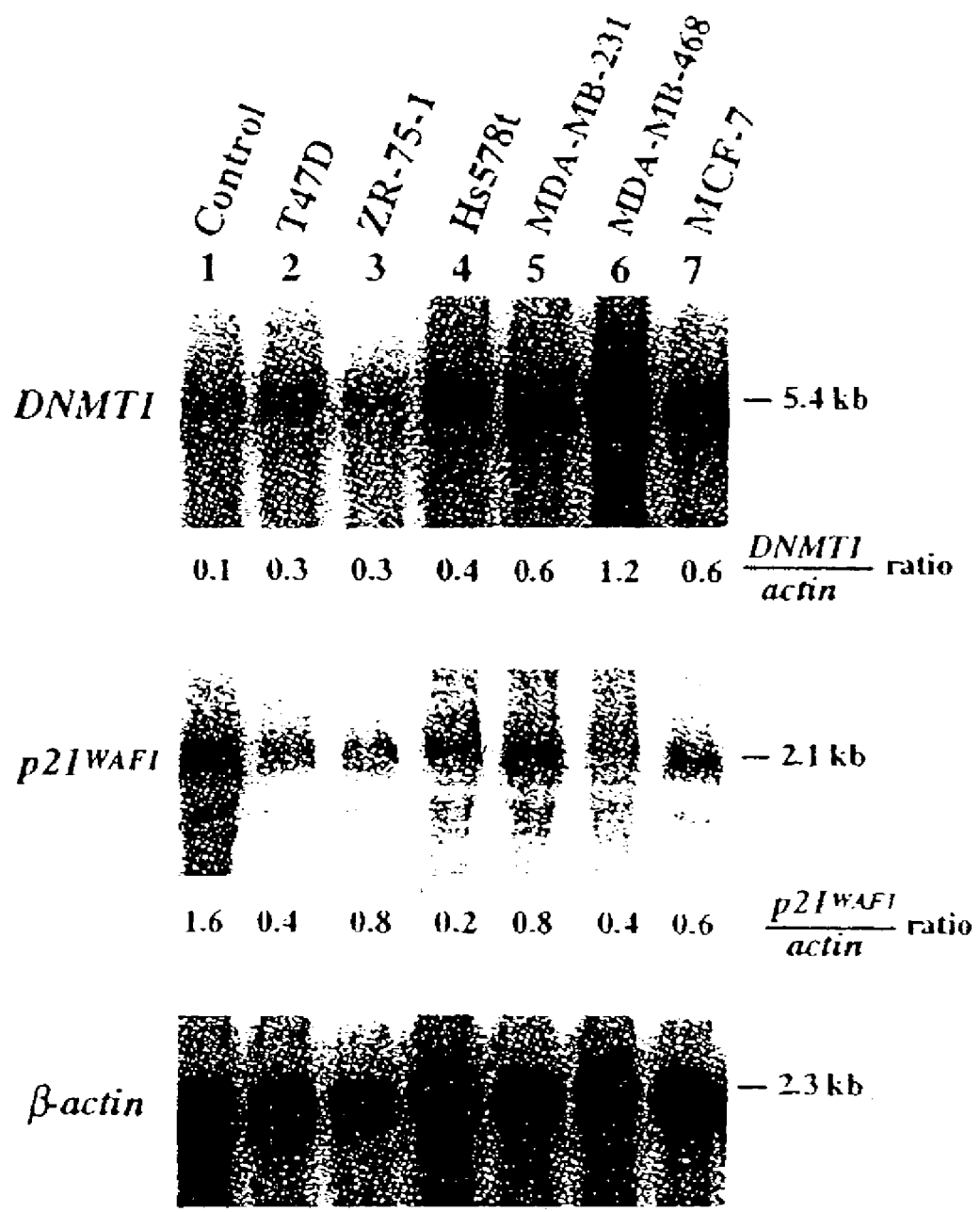
FIG. 1 is a Northern hybridization analysis of DNMT1 and p21WAF1 gene expression in breast cancer cell lines. Total RNA (20 Fg) isolated from normal fibroblast (lane 1) and breast cancer cell lines—T47D (lane 2), ZR-75-1 (lane 3), Hs578t (lane 4), MDA-MB-231 (lane 5), MDA-MB-468 (lane 6), and MCF-7 (lane 7) was subjected to Northern analysis. The membrane was probed with DNMT1 (top panel), p21WAF1 (middle panel), and β-actin (bottom panel), respectively. The predicted sizes (kb) of the indicated transcripts were calculated using the RNA MW I ladder (Boehringer Mannheim) as a standard. Band intensities were quantified with ImageQuant™ Software (Molecular Dynamics) and the relative levels of DNMT1 and p21WAF1 mRNAs were normalized with the expression level of β-actin in each sample lane.

"DMH" is the abbreviation for the high-throughput method of differential methylation hybridization (Huang, T. H.-M. et al., *Hum. Mol. Genet.*, 8:459-470, 1999; see also applicant's U.S. Ser. No. 09/497,855, filed 4 Feb. 2000, Notice of Allowance received 7 Mar. 2003, and incorporated by reference herein in its entirety).

"ECISTs" is the abbreviation for expressed CpG island sequence tags.

"DAC" or "DeoxyC" are abbreviations for 5-aza-2'-deoxycytidine.

"aa-dUTP" is the abbreviation for amino-allyl dUTP.

"SAM" is the abbreviation for significant analysis of microarray, or in particular contexts, S-adenosylmethionine.

"RACE" is the abbreviation for the art-recognized method of rapid amplification of cDNA ends.

The term "MBD" refers to methyl-CpG binding domain.

The term "HDAC" refers to histone deacetylase.

The term "TSA" refers to trichostatin A.

The term "RLCS" refers to RNA ligase-mediated cDNA synthesis.

The term "ChIP" refers to chromatin immunoprecipitation.

The term "COBRA" refers to combined bisulfite restriction analysis (Xiong & Laird, *Nucleic Acids Res.* 25:2532-2534, 1997).

The term "DNMT1" refers to DNA methyltransferase.

"Amplicons" are amplified nucleic acid sequences, corresponding to cells or tissues, that are used as hybridization targets for microarrays (e.g., immobilized ECIST probes), such as those described herein.

The phrase "CpG-rich genomic probe," or "CpG-rich genomic probe fragment" refers to a nucleic acid sequence corresponding to a genomic DNA sequence having a "GC content" $\geq 0.5$ (i.e., guanine plus cytosine equal to or greater than 50%). Such probes include those affixed to a solid support, such as in particular microarray embodiments described and taught herein. Such probes also include "CpG islands," defined below.

The phrase "CpG-rich genomic DNA" refers to a genomic DNA sequence having a "GC content" $\geq 0.5$ (i.e., guanine plus cytosine equal to or greater than 50%).

The phrase "CpG-rich genomic DNA-derived target sequences" refers to hybridization target sequences corresponding to "CpG-rich genomic DNA." Such target sequences, for example, include those target sequences prepared by amplification of genomic DNA or genomic DNA fragments.

The phrase "mRNA-derived target sequences" refers to hybridization target sequences corresponding to expressed genomic sequences (i.e., to mRNA). Such target sequences, for example, include those target sequences prepared by the art-recognized method of RNA ligase-mediated cDNA synthesis (RLCS). Preferably, the method used to prepare mRNA-derived target sequences, preserves the 5'-end sequence of the mRNA, including the first exon.

The phrase "target sequences derived from acetylated histone-associated DNA of the target tissue" refers to hybridization target sequences corresponding to genomic sequences that are associated with (complexed with) acetylated histones. Preferably, said associations or complexes are with acetylated histone H3 or H4. Preferably, said acetylated histones are associated or complexed with a CpG-rich promoter region of a gene, with an exon of a gene, or both. Preferably, said acetylated histones are associated or complexed with a CpG-island or portion thereof corresponding to a gene promoter region. Such target sequences are prepared, for example, by using the method of Weinmann et al., *Genes Dev.* 16:235-244, 2002, but using anti-acetylated histone antibodies for immunoprecipitation of acetylated histone:DNA complexes, instead of using anti-E2F1 antibodies. In particularly preferred inventive embodiments, such target sequences are prepared both before and after treating a test tissue sample with at least one of a demethylating agent (e.g., 5-aza-2'-deoxycytidine) or an inhibitor of histone deacetylases (e.g., trichostatin A), and used in comparative hybridizations with inventive ECIST microarrays.

The term "Observed/Expected Ratio" ("O/E Ratio") refers to the frequency of CpG dinucleotides within a particular DNA sequence, and corresponds to the [number of CpG sites/(number of C bases×number of G bases)]×band length for each fragment.

The term "CpG island" refers to a contiguous region of genomic DNA that satisfies the criteria of (1) having a frequency of CpG dinucleotides corresponding to an "Observed/Expected Ratio" >0.6, and (2) having a "GC Content" $\geq 0.5$. CpG islands are typically, but not always, between about 0.2 to about 1 kb in length, from about 0.2 to about 2 kb in length, or from about 0.2 to about 3 kb in length.

The term "methylation state" or "methylation status" refers to the presence or absence of 5-methylcytosine ("5-mCyt") at one or a plurality of CpG dinucleotides within a DNA sequence. Methylation states at one or more particular palindromic CpG methylation sites (each having two CpG CpG dinucleotide sequences) within a DNA sequence include "unmethylated," "fully-methylated" and "hemi-methylated."

The term "hemi-methylation" or "hemimethylation" refers to the methylation state of a palindromic CpG methylation site, where only a single cytosine in one of the two CpG dinucleotide sequences of the palindromic CpG methylation site is methylated (e.g., 5'-CC$^M$GG-3' (top strand): 3'-GGCC-5' (bottom strand)).

The term "hypermethylation" refers to the methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "de novo methylation" refers to the conversion of unmethylated post-synthesis CpG dinucleotide sequences (within a palindromic CpG methylation site) to fully methylated CpG sequences.

The term "maintenance methylation" refers to the conversion of post-synthesis hemi-methylated CpG dinucleotide sequences (within a palindromic CpG methylation site) to fully methylated CpG sequences.

The term "microarray" refers broadly to both 'DNA microarrays,' and 'DNA chip(s),' as recognized in the art, encompasses all art-recognized solid supports, and encompasses all methods for affixing nucleic acid molecules thereto or synthesis of nucleic acids thereon.

The procedures disclosed herein that involve the molecular manipulation of nucleic acids are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press as incorporated by reference herein.

ECIST Microarrays for Dual Screening of DNA Hypermethylation and Gene Silencing; The Screening Array:

The screening array of the present invention comprises multiple CpG dinucleotide rich fragments affixed to a solid support. These CpG dinucleotide rich fragments affixed to the solid support of the screening array are employed, inter alia, to identify the presence or absence of methylated sites in cells (genomic DNA). Further, these CpG dinucleotide fragments may be any nucleic acid fragment in which CpG dinucleotides comprise at least 50% of the nucleic sequence and which have a length of between about 0.2 to about 1 kb in length.

In preferred embodiments, the affixed CpG dinucleotide rich fragments comprise expressed CpG island sequence tags (ECISTs), described herein below, and are used, according to the present invention, for high-throughput dual analysis of genomic DNA methylation and gene expression.

In preferred embodiments, the CpG dinucleotide fragments affixed to the solid support of the screening array are selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46.

Preferably, the CpG dinucleotide fragments are derived from DNA clones selected from a genomic library, and more preferably from a genomic library in which the concentration of CpG dinucleotides has been enriched. Examples of such CpG dinucleotide rich genomic libraries are the CGI library, the avian CGI library and the mouse CGI library, each of which is available from the United Kingdom Human Genome Center. In preferred embodiments, the nucleic acid fragments are derived from DNA clones of the CGI library and are, themselves, CpG island, or portions thereof. In preferred embodiments, these CpG island containing fragments are ECISTs.

If the nucleic acid fragments are derived from DNA clones of a pre-existing library such as the CGI library, the library is preferably pre-screened with an enzyme to eliminate repetitive sequences. Repetitive sequences are short stretches of DNA dispersed throughout the genome in thousands of copies with no apparent known function which could potentially interfere with the hybridization process. A preferred method utilizes the Cot-1 approach, which hybridizes with repetitive sequences such as AluI and KpnI families. DNA clones negative or weakly positive for the Cot-1 hybridization signals are then selected for amplification (i.e., clones positive for Cot-1 DNA are not selected).

The selected CpG dinucleotide nucleic acid fragments are amplified using art-recognized methods of amplification. Any nucleic acid specimen is utilized as the starting nucleic acid template, provided that it contains the specific nucleic acid sequence containing or corresponding to the target DNA sequence (e.g., a CpG island, or portion thereof). Thus, the amplification process may employ DNA or RNA, wherein DNA or RNA may be double or single stranded. In the event that RNA is to be used as a template, enzymes, and/or conditions optimal for reverse transcribing the template to DNA known to those in the art are utilized.

Suitable in vitro amplification techniques include but are not limited to, the polymerase chain reaction (PCR) method, transcription-based amplification system (TAS), self-sustained sequence replication system (3SR), ligation amplification reaction (LAR), QB RNA replication system and run-off transcription. A preferred method of amplification is PCR amplification, which involves an enzymatic chain reaction in which exponential quantities of the target locus (e.g., a CpG island, or portion thereof) are produced relative to the number of reaction steps performed. PCR amplification techniques and many variations of PCR are known and well documented (see e.g., Saiki et al., Science 239:487-491, 1988; and see U.S. Pat. Nos. 4,682,195, 4,683,202 and 4,800,159, which are incorporated herein by reference.

Typically, the selected DNA clone is denatured, thus forming single strands which are used as templates. One oligonucleotide primer is substantially complementary to the negative (−) strand and another primer is substantially complementary to the positive (+) strand. DNA primers are DNA sequences capable of initiating synthesis of a primer extension product. Primers "substantially complementary" to each strand of the target nucleic acid sequence will hybridize to their respective nucleic acid strands under favorable conditions known to one skilled in the art (e.g., under art-recognized pH, salt, cation, and temperature conditions). As known in the art, such conditions reflect, for example, the size and GC content of the primer sequence. In a preferred embodiment, the primers used in the amplification step are HGMP 3558: 5' CGG CGG CCT GCA GGT CTG ACC TTA A (SEQ ID NO:47) and HGMP 3559: 5' AAC GCG TTG GGA GCT CTC CCT TAA (SEQ ID NO:48).

Annealing the primers to the denatured DNA templates is followed by extension with an enzyme to result in newly synthesized + and − strands containing the target DNA sequence containing the CpG islands. This annealing process consists of the hybridization of the primer to complementary nucleotides of the DNA sequence template in a buffered aqueous solution. The buffer mixture containing the DNA templates and the primers is then heated to a temperature sufficient to separate the two complementary strands of DNA. In a preferred embodiment, the mixture containing the DNA templates and the primers is heated to about 90 to 100° C. from about 1 to 10 minutes, even more preferably from 1 to 4 minutes to allow the DNA templates to denature and form single strands. The mix is next cooled to a temperature sufficient to allow the primers to specifically anneal to sequences flanking the gene or sequence of interest. Preferably, the mixture is cooled to 50 to 60° C., for approximately 1 to 5 minutes. It is understood that the nucleotide sequence of the primer need not be completely complementary to the portion of the DNA template in order to effectively anneal to the DNA template.

A primer extension enzyme is then added to initiate the primer extension reaction to produce newly-synthesized DNA strands. Heat stable enzymes such as pwo (from the hyperthermophilic archaebacterium *Pyrococcus woesei*), *Thermus aquaticus* or *Thermococcus litoralis* DNA polymerases, which eliminate the need to add enzyme after each denaturation cycle are preferably used as the primer extension enzyme. Other preferred amplification enzymes which may be used include, but are not limited to, *Escherichia coli* DNA polymerase I, Klenow fragment of *E. coli* DNA polymerase I, T4 DNA polymerase, T7 DNA polymerase *Thermus aquaticus* (Taq) DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or QB replicase. The temperature of the reaction mixture is then set to the optimum for the DNA polymerase to allow DNA extension to proceed.

These newly synthesized strands are used as templates in repeated cycles of amplification. Thus, PCR consists of multiple cycles of DNA melting, annealing and extension resulting in an exponential production of the target DNA sequence containing the target CpG islands.

After amplification, methylation-sensitive sites of the amplified products are preferably identified by digestion with a methylation-sensitive restriction enzyme. Examples of such methylation-sensitive enzymes are BstU I, SmaI, SacII, EagI, MspI, HpaII, HhaI and BssHII which digest non-methylated CpG dinucleotide regions. In a preferred embodiment, BstU I is used. Positive CpG dinucleotide nucleic acid fragments containing the methylation-sensitive sites are used for differential methylation hybridization (DMH) for a high-throughput analysis of DNA methylation.

The amplified CpG dinucleotide rich fragments are denatured, transferred to a solid support and immobilized thereon using art-recognized methods. Such methods that may be used to crosslink the CpG dinucleotide rich fragments to the solid support include but are not limited to UV light, poly-L-lysine treatment and heat. In a preferred embodiment, the amplified CpG dinucleotide rich fragments are denatured, transferred and immobilized using an UV light to crosslink the CpG dinucleotide rich fragments to the solid support. Depending upon the assay, at least about 20, preferably at least about 100, more preferably at least about 500, or even most preferably at least about 1,000 amplified CpG dinucleotide rich fragments are transferred to and immobilized on the solid support.

In a preferred embodiment of the invention, the CpG dinucleotide rich fragments affixed to the solid support of the screening array are CpG islands containing expressed sequences. CpG island fragments which contain expressed sequences are referred to herein as Expressed CpG Island Sequence Tags (ECIST). In a preferred embodiment, ECIST fragments contain part of the promoter and the first exon of a gene. Typically, the length of each ECIST fragment is at least about 0.3 kb, preferably about 0.4 to 0.5 kb, and most preferably about 0.4 kb. In a preferred embodiment, the ECIST fragments affixed to the solid support of the screening array are CpG island fragments selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, 10 SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46.

ECIST fragments may be identified after the DNA clone is selected from a genomic library and amplified as described above. ECIST fragments are identified by transferring the amplified CpG dinucleotide rich fragments to membranes and screening the CpG dinucleotide rich fragments with a nucleic acid probe to detect the CpG dinucleotide rich fragments which contain sequences expressed in the ample to be evaluated. The nucleic acid probe used for detection of ECIST fragments may be from any source including breast, colon, ovarian, lung and prostate tissue and may be extracted using a variety of methods known in the art. Further, the nucleic acid probe may be DNA, cDNA, or RNA of the gene, or a fragment of the gene, having at least one of the target sequences described above, or an RNA fragment corresponding to such a cDNA fragment. In a preferred embodiment, the nucleic acid probe used to screen for ECIST fragments is a cDNA probe. A positive hybridization signal of the nucleic acid probe to the amplified CpG dinucleotide rich fragment is indicative of a ECIST fragment.

After screening to identify ECIST fragments, methylation-sensitive sites of the amplified products are preferably identified by digestion with a methylation-sensitive restriction enzyme. Examples of such methylation-sensitive enzymes are BstUI, SmaI, SacII, EagI, MspI, HpaII, HhaI and BssHII which digest non-methylated CpG dinucleotide regions. In a preferred embodiment, BstU I is used. Positive CpG dinucleotide nucleic acid fragments containing the methylation-sensitive sites are ECIST fragments which are used for DMH analysis. Where the CpG dinucleotide fragments are ECIST fragments, the undigested nucleic acid fragment contains part of the promoter and first exon of the expressed genes.

The ECIST fragments are denatured, transferred to a solid support and immobilized on the solid support using methods known in the art. Such methods that may be used to crosslink the ECIST fragments to the solid support include but are not limited to UV light, poly-L-lysine treatment and heat. In a preferred embodiment, the ECIST fragments are denatured, transferred and immobilized using an UV light to crosslink the ECIST fragments to the solid support. Depending upon the assay, at least about 20, preferably at least about 100, more preferably at least a bout 500, or even most preferably at least about 1,000 amplified ECIST fragments are transferred to and immobilized on the solid support.

The ECIST fragments affixed to the solid support are, like other affixed CpG dinucleotide rich sequences described herein, used to identify the presence or absence of methylated CpG dinucleotide sites in a cell sample (genomic DNA sample). Further, according to the present invention, the exon-containing portions of ECIST sequences may be used for measuring levels of the corresponding gene expression in the cell sample being tested.

Alternatively, as will be recognized by those skilled in the art, a generic array containing both ECIST and non-ECIST fragments may be prescreened, as described herein above, to identify ECISTS, followed by use of the mixed array for dual methylation and expression analysis.

Accordingly, the present invention is directed to a process for generating a screening array containing expressed gene sequences including: contacting a nucleic acid sequence with an enzyme which digests the nucleic acid sequence into fragments in which CpG islands are preserved; amplifying the fragments to form a plurality of CpG island fragments; screening the plurality of CpG island fragments with a nucleic acid probe to identify CpG island fragments which contain expressed sequences; and affixing the CpG island fragments which contain expressed sequences onto a solid support of the screening array.

In addition to the CpG dinucleotide fragments, other known DNA sequences may be placed on the solid support to serve as orientation marks and for normalization of hybridization signal intensities. For example, CpG dinucleotide fragments for ER, WT1, Rb and p16 may be used.

Any solid support to which the CpG dinucleotide rich fragments may be attached may be employed in the present invention. Examples of suitable solid support materials include, but are not limited to, silicates such as glass and silica gel, cellulose and nitrocellulose papers, and nylon membranes. The solid support material may be used in a wide variety of shapes including, but not limited to slides and membranes. Slides provide several functional advantages and thus are a preferred form of solid support. Due to their flat surface, probe and hybridization reagents can be minimized using glass slides. Slides also enable the targeted application of reagents, are easy to keep at a constant temperature, are easy to wash and facilitate the direct visualization of RNA and/or DNA immobilized on the solid support.

A universal or generic DNA array containing these CpG dinucleotide rich fragments can be developed to use as a hybridization template for methylation screening of various types of cancer. Such cancers include but are not limited to breast, prostate, colon, lung, liver and ovarian cancer. However, those skilled in the art will be able to develop screening arrays containing CpG dinucleotide rich fragments specific for particular cancer types.

Preparation of Amplicons

Amplicons are amplified nucleic acid sequences, corresponding to cells or tissues, that are used as hybridization targets for the microarrays (e.g., immobilized ECIST probes) described herein.

The amplicons of the present invention are amplified nucleic acid fragments derived from a cell sample which are used to probe the CpG dinucleotide rich fragments of the screening array. Generally, amplicons are single or double-stranded amplification products which contain a copy of the target nucleic acid sequence.

Preparation of Amplicons for Differential Methylation Hybridization (DMH) Analysis. For purposes of differential methylation hybridization (DMH), amplicons are prepared by isolating and purifying a nucleotide sequence, preferably DNA, from a sample and digesting the isolated and purified nucleotide sequence with a restriction endonuclease which cuts the sequence into fragments, but leaves CpG dinucleotide rich regions, e.g., CpG islands intact.

The sample of genomic DNA may be obtained from normal (control) cells, an individual's primary tumors, or from clinical specimens containing tumor cells. Cancerous cell types which may be used to prepare the amplicons include but are not limited to breast cancer, ovarian cancer, colon cancer, leukemia, kidney cell cancer, liver cell cancer and lung cancer. Genomic DNA samples can be obtained from any mammalian body fluid, secretion, cell-type or tissue, as well as any cultured cell or tissue. In a preferred embodiment, two sets of amplicons containing methylated CpG dinucleotide sequences are prepared. One set of amplicons is prepared from DNA from non-tumor (control) cells to be used as a reference and a second set of amplicons is prepared from tumor cells.

It is preferred that the restriction enzyme used is an enzyme which has a recognition sequence in regions other than the CpG dinucleotide rich regions of the nucleotide sequence. In a preferred embodiment, the restriction enzyme digests the portions of the nucleotide sequence not containing CpG dinucleotides into fragments having a length of less than about 200 base pairs, which are then discarded. Examples of appropriate restriction enzymes include but are not limited to MseI, Tsp509I, NlaIII and BfaI. In a more preferred embodiment, the restriction enzyme MseI, whose TTAA recognition sequence rarely occurs in CpG dinucleotide sites, is used to digest the nucleic acid sequence. Preferably, the endonuclease-restricted, intact CpG islands are nucleotide fragments in which CpG dinucleotides comprise at least 50% of the nucleic acids and are typically between about 200 to about 2,000 base pairs in length.

The cleaved ends of the endonuclease-restricted, intact CpG islands are ligated to linker primers and amplified. The endonuclease-restricted CpG islands are preferably amplified according to the procedure outlined herein above. In a preferred embodiment, unphosphorylated linker primers such as H24 5' AGG CAA CTG TGC TAT CCG AGG GAT (SEQ ID NO:49) and H12 5'TAA TCC CTC GGA (SEQ ID NO:50) are employed in the extension step of PCR amplification.

Because repetitive DNA sequences in the amplified CpG islands may later interfere with the hybridization process, such sequences may optionally be depleted from the ligated DNA using a subtractive hybridization approach. Examples of repetitive sequences are the Alu I and Kpn I families. Various subtractive hybridization techniques are known and well documented in the art (see e.g., Akopyants et al., *Proc. Natl. Acad. Sci. USA* 95:13108-13, 1998; Lee J. H. and Welch D. R., *Int. J. Cancer* 71:1035-44, 1997; and U.S. Pat. Nos. 5,591,575 and 5,589,339). In a preferred embodiment, a subtractive hybridization approach is carried out using Cot-1 in which human Cot-1 DNA containing enriched repetitive sequences is preferably nick translated, biotin-labeled and added to the treated genomic DNA (see Craig et al., *Hum. Genet.*, 100:472-476, 1997, as incorporated herein by reference). The resulting DNA mixture is then purified and denatured, and the biotin labeled repetitive sequences are allowed to hybridize to the complementary repetitive sequences, on the genomic DNA. Biotin has a high affinity for avidin, and the repetitive sequence hybrids will attach to the magnetic particles via biotin-streptavidin interaction when streptavidin-magnetic particles are added to the DNA mixture. The repetitive sequence hybrids are separated from the CpG islands using a magnetic particle separator. The supernatant containing the CpG islands is removed and purified using methods known in the art.

The resulting amplicons containing methylated and unmethylated CpG islands are purified and digested with appropriate methylation-sensitive restriction enzymes. The methylation-sensitive restriction enzymes will cut their DNA recognition sites when those sites are not methylated but do not cut the corresponding DNA site if it is methylated. Thus, unmethylated CpG islands are degraded and the corresponding methylated CpG islands survive the endonuclease treatment. Examples of such methylation-sensitive enzymes are BstU I, SmaI, SacII, EagI, MspI, HpaII, HhaI and BssHII. In a preferred embodiment, BstU I, whose CGCG recognition sequence occurs frequently within CpG islands is used. This methylation-sensitive enzyme is particularly preferred if the CpG dinucleotide fragments immobilized on the screening array are derived from DNA clones selected from the CGI genomic library, because approximately 800 of the CGI inserts contain BstU I sites (Cross et al., *Nature Genet.*, 6:236-244, 1994).

In a preferred embodiment, only a fraction of the methylated and unmethylated CpG islands are digested with a methylation-sensitive restriction enzyme. The remaining fraction is not digested with a methylation-sensitive enzyme. As a result, two sets of amplicons are generated to probe the CpG dinucleotide rich screening array: one set of amplicons containing methylated and unmethylated amplicons (e.g., amplicons treated with Mse I, but not BstU I) and a second set of amplicons containing methylated amplicons (e.g., amplicons treated with Mse I and BstU I). The set of amplicons containing methylated and unmethylated CpG islands is preferably used as a control in hybridization to determine whether the CpG dinucleotide rich nucleic fragments of the screening array are representative of the repertoire of CpG dinucleotide fragments. The second set of amplicons, containing methylated CpG islands, is then used to identify methylated CpG island sequences in the cell sample by DMH.

The endonuclease-restricted amplicons are then amplified, preferably using PCR as is generally described above in connection with the preparation of CpG dinucleotide rich fragments. A relatively low number of amplification cycles is preferably used to prevent the overabundance of remaining repetitive sequences generated by PCR. In a particularly preferred embodiment, the amplicons are subjected to least fifteen and no more than about thirty amplification cycles. In a more preferred embodiment, the amplicons are subjected to approximately fifteen amplification cycles.

The amplicons are then preferably purified and labeled. The term "labeled" is herein used to indicate that there is some method to visualize the CpG dinucleotide fragments hybridized to the amplicons. There are many different labels and methods of labeling known to those of ordinary skill in the art, including but not limited to radiolabels, fluorescent labels, phosphorescent labels, enzymic labels, mass labels detectable in a mass spectrometer, and combinations thereof. Moreover, a wide variety of direct and/or indirect means are available to enable visualization of the subject nucleic sequences that have hybridized to the prepared DNA array. Suitable visualizing means include radioisotope labels and non-radioisotope labels such as fluorescence-based detection technologies. Examples of radioisotope labels that can be used include $^{32}P$ and $^{33}P$-dCTP, and examples of non-radioisotope labels that can be used include Cy3-dUTP and Cy5-dUTP. Further, any labeling techniques known to those in the art could be useful to label the subject nucleic acid sequence in of this invention. Several factors may govern the choice of labeling means, including the effect of the label on the rate of hybridization and binding of the methylated amplicons to the CpG dinucleotide rich screening array, the nature and intensity of the signal generated by the label and the expense and ease in which the label is applied.

In particular, the present invention provides a process for isolating a set of amplicons to identify methylation patterns from a cell sample which includes: contacting nucleic acid sequences with an enzyme which digests the nucleic acid sequences into fragments in which CpG islands are preserved; attaching the cleaved ends of the fragments to linker primers to form linker primer products; contacting the linker primer product with a methylation-sensitive enzyme which digests the linker primer products having unmethylated CpG dinucleotide sequences but not methylated CpG dinucleotide sequences to form a digestion product comprising methylated CpG island loci; and amplifying the digestion product to form amplicons.

It will be obvious to those skilled in the art that various modifications of the disclosed embodiments are useful to practice the present invention, and yet are encompassed by the present invention. For example, a larger panel of ECISTs is employed. More ECISTs are identified, for example, by screening GC-rich DNA fragments derived from a CpG island library, CGI (Cross, S. H. et al., *Nat. Genet.*, 6:236-244, 1994).

Finally, not all DNA segments of important methylation-associated genes are present in the CGI library. Such ECISTs are individually prepared by PCR using primers designed to flank the promoter and first exon of these genes. Thus, by modifying the inventive protocol, a new type of DNA chip is generated, containing high-density ECISTs arrayed on solid supports (e.g., nylon membrane or glass slide) for genome-wide screening of DNA methylation and gene expression.

Preparation of Amplicons for Expression Analysis. Amplicons for expression analysis are made using art-recognized methods for generating and amplifying cDNAs. Preferably, full length cDNAs are generated and amplified. Preferably, the method is biased toward generation of cDNA from initially capped mRNA, rather than uncapped ribosomal RNA, tRNA or fragmented RNA. Preferably the method involves separation of capped from uncapped or fragemented RNA, for example using a combination of calf intestinal phosphatase followed by purification with Qiagen RNEASY™ column. Preferably, the method of cDNA production involves removal of RNA cap structures (e.g., by treatment with tobacco acid pyrophosphates), and ligation of adapters to the 5' monophosphate ends of the de-capped mRNA population in the presence of T4 RNA ligase. Preferably, full-length cDNA is generated from such ligated mRNAs by reverse transcription with polyT primers. Preferably, long-PCR reactions (TAQPLUS™ Long PCR System, Stratagene) are performed using 5'- and 3'-adapter primers, using low amplification cycles (e.g., about 18 cycles) to preserve the linearity of PCR.

Preferably, the amplified products (or amplicons) are purified for labeling. Preferably, the labeling is fluorescence labeling, for example, involving incorporation of amino-allyl dUTP (aa-dUTP) into amplicons and coupling fluorescence dyes (e.g., Cy5 and Cy3) to aa-dUTP-labeled test and reference amplicons, respectively.

Preferably, the labeled amplicons are co-hybridized to CpG island microarray panels, and the hybridization results analyzed with appropriate art-recognized software (e.g., GenePix Pro3.0) so that In particular, the present invention provides a process for isolating a set of amplicons to determine expression or expression patterns of one or more genes from a cell sample which includes: obtaining isolated mRNA from a cell or tissue sample; obtaining capped mRNA from the isolated mRNA; decapping the capped mRNA; production of full-length cDNA from the decapped rRNA; amplification of the full-length cDNA to produce amplicons; and labeling of the amplicons, whereby hybridization of the labeled amplicons to arrayed ECISTs can be followed.

It will be obvious to those skilled in the art that various modifications of the disclosed amplicon preparation embodiments are useful to practice the present invention, and yet are encompassed by the present invention. For example, thermostable reverse transcriptases are used to synthesize full-length cDNA templates at higher reaction temperatures. This enhances target preparation by opening up of highly GC-rich regions, particularly at the 5'-end of some mRNA species, for reverse transcription.

The full-length cDNAs prepared using the present protocols are all 5'- and 3'-RACE ready and are suitable for cloning novel genes of interest.

Additionally, the T7 sequence is attached to the original RNA adapter ligated to the 5'-end of decapped mRNAs to ensure that most ECISTs contain the first exon. Accordingly, double-stranded full-length cDNAs are synthesized and used as templates from which the 5'-end cRNAs are synthesized in a single direction by T7 RNA polymerase. These cRNAs are then used as targets for screening ECISTs from, for example, the CGI genomic library. This approach is routinely used to prepare the 5'-end cRNAs from test samples without PCR. The linearity of the target population is therefore preserved, allowing for quantitative determination of the microarray outcomes.

Screening

The labeled amplicons are used to screen the CpG dinucleotide fragments of the screening array produced using the above methods. Labeled amplicons having a complementary sequence to that of a CpG dinucleotide fragment affixed on the solid support of the screening array will result in a positive hybridization signal. Preferably, the CpG dinucleotide fragments affixed to the screening array are ECIST fragments. If amplicons are used to probe ECIST fragments, positive hybridization signals will also indicate the presence of DNA sequences which are expressed in the cell sample.

In a preferred embodiment, methylated (e.g., MseI/BstUI-pretreated amplicons) amplicons are used to screen the CpG dinucleotide rich fragments of the screening array. Positive hybridization signals indicate the presence of methylated DNA in the cell sample.

In particular, the present invention is directed to a process for determining the presence or absence of methylation, of a CpG dinucleotide rich region of a nucleic acid sequence within a genome, the process comprising: contacting the nucleic acid sequence with an enzyme which digests the nucleic acid sequences into fragments in which CpG islands are preserved; attaching the fragments to linker primers to form linker primer products; contacting the linker primer products with a methylation-sensitive enzyme which digests the linker primer products having unmethylated CpG dinucleotide sequences but not methylated CpG dinucleotide sequences to form a digestion product comprising methylated, CpG island loci; amplifying the digestion product to form amplicons; labeling the amplicons; contacting the labeled amplicons with a screening array comprising a plurality of nucleic acid fragments affixed to a solid support; and determining the presence or absence of labeled amplicons bound to the plurality of nucleic acid fragments of the screening array.

In a preferred embodiment, the CpG dinucleotide fragments of the screening array are screened using two sets of endonuclease treated amplicons: one set of amplicons which contain methylated and unmethylated CpG islands (e.g., amplicons treated with Mse I, but not BstU I) and a second set of amplicons which contain methylated CpG islands (e.g., amplicons treated with MseI and BstUI). This first set of amplicons containing methylated and unmethylated CpG islands is preferably used as a control in hybridization to determine whether the amplified products are representative of the repertoire of CpG dinucleotide rich fragments. Preferably, the first set of amplicons containing methylated and unmethylated amplicons are amplicons treated with Mse I. The first set of amplicons is completely removed and the screening array is then rehybridized using the second set of amplicons containing methylated CpG islands. Alternatively, the second set of amplicons containing methylated CpG islands is used to screen a second screening array containing CpG dinucleotide fragments which are identical to the CpG dinucleotide fragments of the screening array probed with the first set of amplicons. In a preferred embodiment, the second set of amplicons contains Mse I/BstU I-pretreated amplicons. Positive hybridization signals resulting from the second hybridization using amplicons containing methylated CpG islands indicate the presence of methylated CpG island sequences in the cell sample being tested. Further, positive hybridization signals using both sets of amplicons (e.g., Mse I-treated amplicons and Mse I/BstU I amplicons) indicate the presence of aberrantly methylated DNA in the cell sample.

Accordingly, the present invention provides a process for determining the presence or absence of aberrantly methylated DNA in a cell sample, said process comprising:

a) preparing a first set of amplicons comprising (i) contacting a nucleic acid sequence with an enzyme which digests the nucleic acid sequences fragments in which CpG islands are preserved to form a digestion product comprising methylated and unmethylated CpG island loci; (ii) attaching the digestion product to linker primers to form linker primer products; (iii) amplifying the linker primer products to form amplicons; (iv) labeling the amplicons;

b) preparing a second set of amplicons comprising (i) contacting nucleic acid sequences with an enzyme which digests the nucleic acid sequences into fragments in which CpG islands are preserved; (ii) attaching the fragments to linker primers to form linker primer products; (iii) contacting the linker primer products with a methylation-sensitive enzyme which digests the linker primer products having unmethylated CpG dinucleotide sequences but not methylated CpG dinucleotide sequences to form a second digestion products comprising methylated CpG island loci; (iv) amplifying the second digestion product to form amplicons; (v) labeling the amplicons;

c) contacting the first set of amplicons with a first screening array comprising a plurality of nucleic acid fragments affixed to a solid support and determining the presence or absence of labeled amplicons bound to the plurality of nucleic acid fragments of the first screening array;

d) contacting the second set of amplicons with a second screening array which comprises a plurality of nucleic acid fragments affixed to a solid support where in the plurality of nucleic acid fragments of the second screening array are identical to the plurality of nucleic acid fragments of the first screening array and determining the presence or absence of labeled amplicons bound to the plurality of nucleic acid fragments of the second screening array; and e) observing whether the presence or absence of the first set of amplicons bound to the nucleic acid fragments of the first screening array is the same as the presence or absence of the second set of amplicons bound to the nucleic acid fragments of the second screening array.

In another preferred embodiment, the screening array is probed using two sets of methylated amplicons. The first set of methylated amplicons is prepared from a non-cancer (control) cell to be used as a reference and the second set of methylated amplicons is prepared from a cancer cell. The CpG dinucleotide fragments of the screening array are first screened using amplicons containing methylated CpG islands prepared from a non-cancer cell. Preferably, Mse I/BstU I-treated amplicons from a non-cancer cell will be used in this first hybridization. The first set of methylated amplicons is completely removed and the screening array is then rehybridized using the second set of amplicons containing methylated CpG islands prepared from a cancer cell. Preferably, Mse I/BstU I treated amplicons from a tumor cell will be employed in this second screening. Alternatively, the second set of amplicons are used to screen a second screening array containing CpG dinucleotide fragments which are identical to the CpG dinucleotide fragments of the screening array screened with the first set of methylated amplicons prepared from non-tumor cells. The difference in the hybridization signal intensities using the second set of methylated amplicons from a cancer cell as compared to the intensities of the hybridization signals obtained using the first set of methylated amplicons from a non-cancer (control) cell reflects the aberrant methylation patterns of the corresponding sequences in the cancer cell DNA.

In particular, the present invention is directed to a process for identifying methylation patterns in DNA from a cancer cell including:

a) isolating a first set of amplicons comprising (i) contacting nucleic acid sequences derived from a cancer cell with an enzyme which digests the nucleic acid sequences into fragments in which CpG islands are preserved; (ii) attaching the fragments to linker primers to form linker primer products; (iii) contacting the fragments with a methylation-sensitive enzyme which digests the fragments having unmethylated CpG dinucleotide sequences but not methylated CpG dinucleotide sequences to form a digestion product comprising methylated CpG island loci; (iv) amplifying the digestion product to form amplicons; and (v) labeling the amplicons;

b) isolating a second set of amplicons comprising repeating (i) through (v) of step (a) wherein the nucleic acid sequences of (i) are nucleic acid sequences derived from a non-cancer cell;

c) contacting the first set of amplicons with a first screening array comprising a plurality of nucleic acid fragments affixed to a solid support and determining the presence or absence of labeled amplicons bound to the plurality of nucleic acid fragments of the screening array;

d) contacting the second set of amplicons with a second screening array comprising a plurality of nucleic acid fragments affixed to a solid support wherein said plurality of nucleic acid fragments of the second screening array are identical to the plurality of nucleic acid fragments of the first screening array and determining the presence or absence of labeled amplicons bound to the plurality of nucleic acid fragments of the second screening array; and e) observing whether the presence or absence of the first set of amplicons bound to the plurality of nucleic acid fragments of the first screening array is the same as the presence or absence of the second set of amplicons bound to the plurality of the nucleic acid fragments of the second screening array.

In particularly preferred embodiments, the screening arrays used for identifying methylation patterns in DNA are arrays comprising ECISTs, whereby gene silencing associated with DNA methylation of the corresponding genomic loci can be determined by rescreening the same ECIST screening array with cDNA-derived amplicons (as described herein above) corresponding to, for example, reference and cancer samples according to the present invention.

Label intensities are obtained for each hybridized spot in such arrays. In preferred embodiments, as described herein, Cy3 and Cy5 (e.g., reference and test samples, respectively) fluorescence intensities are obtained for each spot and analyzed using art-recognized software. Array spots with fluorescence signals close to the background signal, reflecting PCR or printing failures, are excluded from the data analysis. Preferably, because labeling efficiencies (e.g., Cy5 and Cy3 labeling efficiencies) may vary among samples, Cy5/Cy3 ratios from each image are normalized according to their global Cy5/Cy3 ratio, as well as internal controls (with normalized ratios expected to be 1). Preferably, internal control panels include different fragments of control genes (e.g., different β-actin cDNA fragments (exons 1 and 3), and 2 different GAPDH cDNA fragments (exons 1 and 8)), spotted at several concentrations on each array. The adjusted Cy5/Cy3 ratio for each ECIST locus is then calculated, and data exported in a spreadsheet format for analysis. In preferred embodiments, additional control microarray experiments are performed, wherein the dye-coupling of test (Cy3) and reference (Cy5) amplicons are reversed. The acquired microarray data are then used to compare data derived from the complementary experiment. Preferably, quality control, self-hybridization studies are conducted, wherein 2 equal portions of a test DNA sample are labeled with Cy5 and Cy3, respectively, and co-hybridized to a microarray slide.

Preferably, statistical analysis of gene expression data is accomplished by using art-recognized image analysis software (e.g., SAM; Tusher, V. G., et al., *Proc. Natl. Acad. Sci. USA*, 98:5116-5121, 2001). Preferably, the 3 hybridization experiments (e.g., repeated and self-hybridization) are used as inputs for analysis. Preferably, the derived expression data are transformed to cube root to obtain a normal distribution before performing the analysis.

Experimental results utilizing the present dual DMH/expression methods indicate that alteration of genomic methylation and expression patterns is related to tumor growth in cancer development. Specifically, the present dual methods have been used to identify hypermethylated CpG island sites as effective markers for whether or not a patient has cancer. These marker sites were identified using tumor cells from breast cancer patients. Alteration of CpG dinucleotide methylation patterns is likely a key, and a common event in the development of neoplasia. Aside from the effect of DNA-MTase on methylation, the present experiments suggest that additional factors such as pre-existing methylation of CpG dinucleotides may account for de novo methylation in cancer cell lines.

Without being bound by any theory, progressive accumulation of methylated CpG islands occurs during tumor development. Therefore, pre-existing methylation within a CpG island locus may promote subsequent de novo methylation in cancer cells. As a result of CpG island hypermethylation, critical tumor suppressor genes become silenced, leading to some cells with growth advantage. The results of the experiments discussed in the following examples offer an alternative explanation for the underlying mechanisms in direct contrast to the random nature of the de novo DNA methylase activities previously proposed in transformed cells.

Furthermore, differential methylation and expression patterns in various clinical specimens are associated with different stages or types of cancer. Thus, a determination of the methylation and/or gene expression patterns in tumor cells allows for the identification of gene markers indicative of cancer. Hence, the present DMH and gene expression measuring methods have broad utility for identifying differentially methylated CpG island sites in a genome; for mapping hypermethylated DNA sites which are related to disease development; for determining methylation-associated gene silencing, and for understanding the role of DNA methylation in normal cell genomic DNA imprinting, differentiation, and development; for understanding the role of DNA methylation in tumorigenesis; and for diagnosing and monitoring the prognosis of disease.

The following examples illustrate the invention, but are not to be taken as limiting the various aspects of the invention so illustrated.

EXAMPLE 1

Materials and Methods for Examples 2-6

Cell culture and tissue sample preparations. The T47D, ZR-75-1, Hs578t, and MDA-MB-468 breast cancer cell lines were acquired from the American Type Culture Collection (Rockville, Md.). The MDA-MB-231 and MCF-7 cell lines were obtained from Dr. Wade V. Welshons at the University of Missouri School of Veterinary Medicine (Columbia, Mo.). T47D and ZR-75-1 were maintained in RPMI 1640 media with 10% fetal bovine serum, while the remaining cell lines were maintained in Earle's Modified Eagle's Medium with 10% fetal bovine serum. Breast tumor and adjacent, non-neoplastic tissue (used as a normal control) were obtained from patients undergoing mastectomies at the Ellis Fischel Cancer Center (Columbia, Mo.). Total RNA and genomic DNA from samples were isolated using the RNeasy Total RNA Kit™ (Qiagen) and QIAamp Tissue Kit™, respectively.

Northern hybridization. Twenty mg of total RNA from breast cancer cell lines and a normal control fibroblast sample were electrophoresed on a 1.4% agarose gel in the presence of 2.2 mM formaldehyde and transferred to a nylon membrane. cDNA probes were prepared from cells known to express DNMT1 and p21$^{WAF1}$ by reverse transcription-PCR. A 192-bp product was generated for DNMT1 using primers 5' ATC TAG CTG CCA AAC GGA G (SEQ ID NO:51) (sense strand) and 5' CAC TGA ATG CAC TTG GGA GG (SEQ ID NO:52) (antisense strand). A 206-by product was generated for p21 using primers 5' AAC TAG GCG GTT GAA TGA GAG GTT (SEQ ID NO:53) (sense strand) and 5' GTG ACA GCG ATG GGA AGG AG (SEQ ID NO:54) (antisense strand). The resulting PCR products were isolated and $^{32}$P-labeled using the Multiprime DNA labeling system (Amersham). The Northern membrane was hybridized with radiolabeled DNMT1 and p21$^{WAF1}$ cDNA probes, respectively. Hybridization was performed in 8 ml Hybrisol I (Oncor) at 42° C. overnight. Washing was performed once for 20 min in 0.1% SDS-0.5×SSC (1×SSC is 0.15 M NaCl plus 0.015 M sodium citrate, pH 7.0) and twice for 20 min each in 0.1% SDS-0.2× SSC at 65° C. The same membrane was also hybridized with a $^{32}$P-labeled b-actin cDNA (1.1-kb) probe to determine the a mount of RNA loaded. The hybridized membrane was subjected to phosphorimage analysis with a Molecular Dynamics PhosphorImager, and band intensities were quantified with ImageQuant Software (Molecular Dynamics). The levels of DNMT1 and p21$^{WAF1}$ mRNAs were normalized with the level of beta-actin mRNA in the respective sample lanes.

Amplicon generation. Approximately 2 mg of genomic DNA from breast cancer cell lines or normal breast tissue were restricted to completion with 10 units of Mse I per mg DNA following the conditions recommended by the supplier (New England Biolabs). The digests were purified, and mixed with 0.5 nmol of unphosphorylated linkers H-24 and H-12 in a DNA lipase buffer (New England Biolabs). The oligonucleotide sequences were as follows: H-24: 5' AGG CAA CTG TGC TAT CCG AGG GAT (SEQ ID NO:49) and H-12: 5' TAA TCC CTC GGA (SEQ ID NO:50). Oligonucleotides were annealed by cooling the mixture gradually from 50° to 25° C. and then ligated to the cleaved ends of the DNA fragments by incubation with 400 units of T4 DNA ligase (New England Biolabs) at 16° C. Repetitive DNA sequences were depleted from the ligated DNA using a subtraction hybridization protocol described by Craig et al. Briefly, human Cot-1 DNA (20 mg; Gibco/BRL) containing enriched repetitive sequences was biotin-labeled using the Nick Translation Kit (Gibco/BRL) and added to the treated genomic DNA. The DNA mixture was purified and dried under vacuum. The dried mixture was redissolved in 10 ml of 6×SSC and 0.1% SDS, denatured by boiling for 10 min, and hybridized at 65° C. overnight. One hundred ml (1 mg) of streptavidin-magnetic particles were added to the hybridization mixture and incubated at room temperature for 30 min. Streptavidin-magnetic particles were prepared according to the manufacturer's instructions (Boehringer Mannheim). Tubes were applied to a magnetic particle separator (Boehringer Mannheim) and the supernatant was aspirated. This supernatant was incubated again at room temperature for 30 min with freshly prepared streptavidin-magnetic particle solution. After the incubation, the second supernatant was removed and DNA was purified using a QIAquick kit (Qiagen). Half of the resulting DNA was digested with the methylation-sensitive endonuclease BstU I (New England Biolabs) following the conditions recommended by the supplier. PCR reactions were performed with the pretreated DNAs (Mse I or Mse I/BstU I) (500 ng) in a 100 ml volume, containing 0.4 mM T-24 primer, 2 units Deep Vent (exo-) DNA polymerase (New England Biolabs), 5% (v/v) dimethyl sulfoxide, and 200 mM dNTPs in a buffer provided by the supplier. The tubes were incubated for 3 min at 72° C. to fill in 5' protruding ends of ligated linkers and subjected to 15 cycles of amplification consisting of 1 min denaturation at 95° C. and 3 min annealing and extension at 72° C. in a PTC-100 thermocycler (MJ Research). The final extension was lengthened to 10 min. The use of low amplification cycles is essential to prevent overabundance of leftover repetitive sequences generated by PCR. The amplified products, designated as "Mse I-pretreated amplicons" or "Mse I/BstUI-pretreated amplicons," were purified using the QIAquick kit, and 50 ng of the DNA were $^{32}$P-labeled using the random primer labeling system as described above.

Differential methylation hybridization. Approximately 3,000 clones derived from the CGI genomic library were prescreened with $^{32}$P-labeled Cot-1 DNA. Clones negative or weakly positive for the Cot-1 hybridization signals were picked and placed into 96-well PCR microplates. A fraction of each colony was transferred to a well of separate 96-well culture chambers for later use. Insert from each clone was amplified in a total volume of 20 ml per tube following the conditions described earlier. Thirty cycles of amplification were performed with denaturing for 1 min at 94° C., annealing for 1 min at 55° C., and extension for 3 min at 72° C. The primers used for amplification were HGMP 3558: 5' CGG CCG CCT GCA GGT CTG ACC TTAA (SEQ ID NO:47) and HGMP 3559: 5' AAC–GCG TTG GGA GCT CTC CCT TAA (SEQ ID NO:48). After PCR, 1 ml of the amplified products was digested with the methylation-sensitive BstU I, and the digests were size fractionated on 1% agarose gels. Inserts (0.2 to 1.5-kb) of the tested CGI clones containing multiple BstU I sites (based on the digestion patterns) were selected for further analysis. The remaining DNA was denatured at 95° C. for 5 min, 2 ml of tracking dye (bromophenol blue) was added to each tube and the DNA was transferred to nylon membranes using a 96-pin MULTI-PRINT™ replicator (V & P Scientific). Each PCR sample was dotted in duplicate, and the position of each dot in the array was marked by the tracking dye. Each pin transfers an approximately 0.4 ml-hanging drop (about 40 ng DNA) onto a membrane. An alignment device (LIBRARY COPIER™; V&P Scientific) was used in conjunction with the replicator to convert three 96-well PCR samples in duplicate into one recipient of 276 dots on a 10×12-cm nylon membrane. Additionally, 3 positive controls were dotted in quadruplicate on the corners (the top and bottom three rows of the first and last columns) of array to serve as orientation marks and for normalization of hybridization signal intensities of dotted genomic fragments. Membranes were first hybridized with $^{32}$P-labeled Mse I-pretreated amplicons overnight at 65° C. in 10 ml of High Efficiency Hybridization solution (Molecular Research, Inc.). Washing was performed once for 20 min in 0.1% SDS-0.5×SSC (1×SSC is 0.15 M NaCl plus 0.015 M sodium citrate, pH 7.0) and twice for 20 min each in 0.1% SDS-0.2×SSC at 65° to 75° C. Autoradiography and analysis were completed using the Molecular Dynamics PhosphorImager and the ImageQuant Software as described earlier. Probes were completely stripped, and the same membranes were rehybridized with $^{32}$P-labeled Mse I/BstU I-pretreated amplicons. Each hybridization experiment was independently performed twice using duplicate membranes.

DNA Sequencing. Plasmid DNA was prepared from positive CGI clones and sequenced using the DyeDeoxy Terminator Cycle Sequencing kit and the automated ABI PRISM 377 sequencer. The nucleotide sequence data were compared to GenBank using the BLAST program.

Methylation Analysis by Southern Hybridization. Genomic DNA (10 µg) from breast cancer cell lines or breast specimens was digested to completion with Mse I or Mse I/BstU I. The restriction products were separated on 1.0% agarose gels and transferred to nylon membranes. Portions of CGI clone inserts were PCR-amplified as probes for Southern hybridization. Amplified products were designed to be ~200 to 300-bp in length and contain no BstU I sites. Hybridization was conducted in 8 to 10 ml of High Efficiency Hybridization solution for overnight at 65-70° C. Post-hybridization washing was carried out as described above. Southern blots were subjected to phosphorimage analysis, and band intensities were quantified with the ImageQuant software.

EXAMPLE 2

Expression of DNMT1 and p21$^{WAP1}$ in Breast Cancer Cells

Human cancer cells have increased DNA-MTase activities known to promote CpG island hypermethylation during tumor progression. See Vertino et al., *Mol. Cell Biol.*, 16:45554565 (1996); Wu et al., *Cancer Res.*, 56: 616-622 (1996); Belinsky et al., *Proc. Natl. Acad. Sci. USA*, 93: 4045-4050 (1996). Since DNMT1 is primarily responsible for DNA-Mtase synthesis, its mRNA levels were determined in breast cancer cell lines T47D, ZR-75-1, Hs578t, MDA-MB-231, MDA-MB-468, and MCF-7.

RNA from breast cancer cell lines T47D, ZR-75-1, Hs578t, MDA-MB-231, MDA-MB-468, and MCF-7 were isolated and prepared for Northern analysis using the methods and materials provided in Example 1. cDNA probes for DNMT1 and p21$^{WAP1}$ were also prepared using the methods and materials described in Example 1. Northern analysis showed 3- to 12-fold higher levels of the 5.4-kb DNMT1 mRNA in these cell lines compared with a normal control sample (FIG. 1, upper panel). These results are consistent with a previous study that showed both increases of DNMTI mRNA levels and the resulting elevation of DNA-MTase enzyme activities in the same cell lines.

It has also been recently shown that the p21 protein negatively regulates targeting of DNA-MTase to the replication-associated protein PCNA. It has been proposed that the presence of p21 prevents DNA-MTase access to replicating DNA, thereby impeding hypermethylation in normal cells, while loss or decreased expression of p21 in tumor cells may facilitate aberrant methylation. Therefore, the expression of the 2.1-kb p21$^{WAP1}$ transcript, the gene encoding p21 in these breast cancer cells, was detected in the cell lines with levels 2- to 8-fold lower than the normal control sample (FIG. 1, middle panel). This result, together with the DNMT1 finding, suggests that these breast cancer cell lines possess an increased capacity to aberrantly methylate their genomes.

EXAMPLE 3

Methylation Profiling of CpG Islands in Human Breast Cancer Cells by Differential Methylation Hybridization (DMH)

Figure 2:
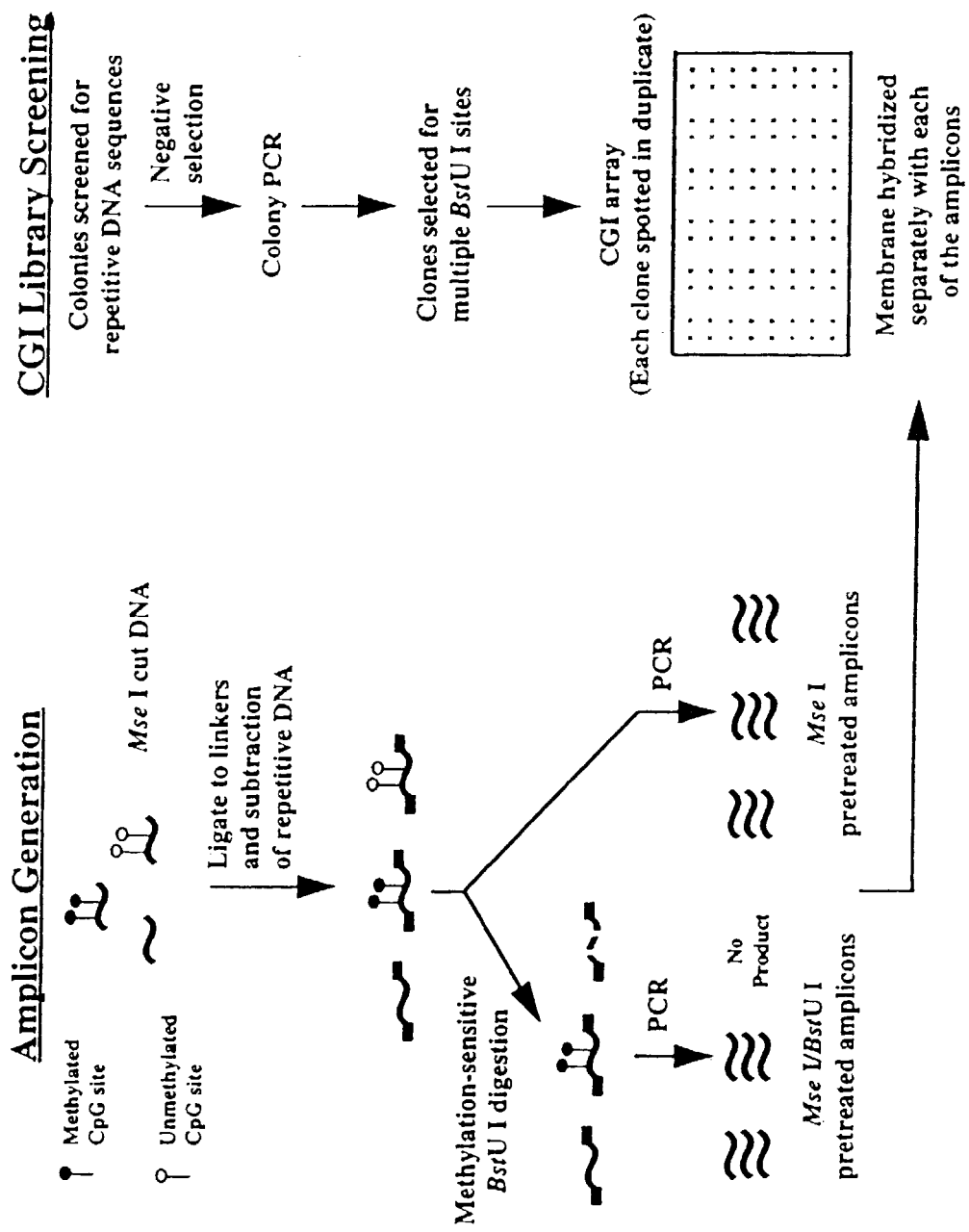
FIG. 2 is a schematic flowchart for differential methylation hybridization. The diagram illustrates the preparation of amplicons used as hybridization probes and selection of CpG island genomic clones gridded on high-density arrays.

DMH was utilized to determine the extent of CpG island sequences undergoing de novo methylation in the 6 cancer cell lines described above in Example 2 (FIG. 2). Genomic DNA from breast cancer cells (T47D, ZR-75-1, Hs578t and MDA-MB-468) was used to prepare amplicons as described above in the Materials and Methods provided in Example 1. DNA from normal breast tissue was similarly digested and used as a control. The cleaved ends of the CpG dinucleotide rich fragments were ligated to linkers and repetitive sequences such as the Alu I and Kpn I families were removed from the digests using a Cot-1 subtractive hybridization approach (see Materials and Methods).

Figure 3:
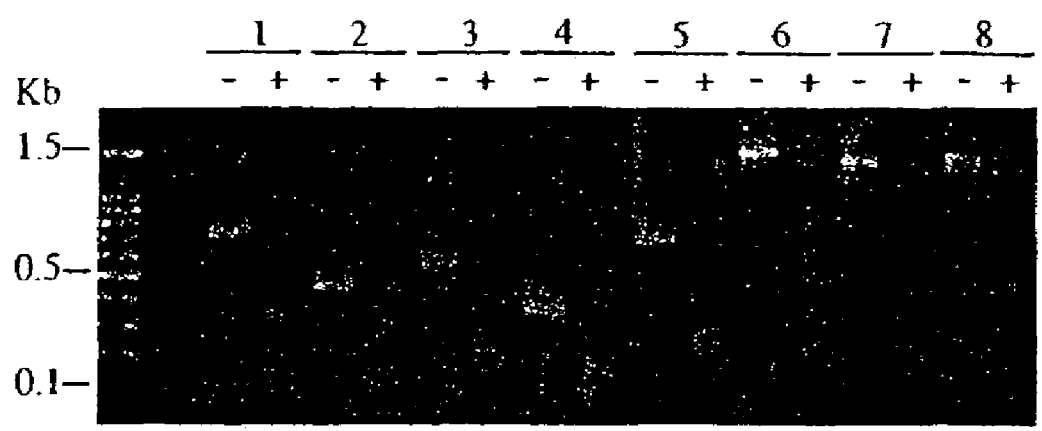
FIG. 3 is BstU I analysis of CpG island clones. Inserts from each clone was amplified by colony PCR and digested with BstU I. The digested (+) and undigested (-) insert DNA samples were separated on 1.5% agarose gels and stained with ethidium bromide. Based on the sizes of the digested fragments, clones containing more than or equal to two BstU I sites were further selected for analysis by differential methylation hybridization. Molecular weight markers (100-bp ladder; Promega) are shown at left.

Half of the subtracted DNA was further treated with methylation-sensitive endonuclease BstU I and both BstU I-digested and undigested, control DNAs were used as templates for linker-PCR (see Material and Methods). Genomic fragments containing unmethylated BstU I sites were cut and could not be amplified in the treated samples, whereas the same fragments were amplified in the BstU I-undigested, control samples. Some fragments containing methylated BstU I sites in the cells were protected from the digestion and were amplified by linker-PCR. The PCR products designated as "Mse I-pretreated amplicons" or "Mse I/BstU I-pretreated amplicons" were used as probes for screening hypermethylated sequences. CpG island clones were pre-selected from the CGI library to contain multiple BstU I sites (FIG. 3), and their amplified insert DNA (0.2 to 1.5-kb) was gridded on high-density arrays as described in the Materials and Methods of Example 1.

Figure 4:
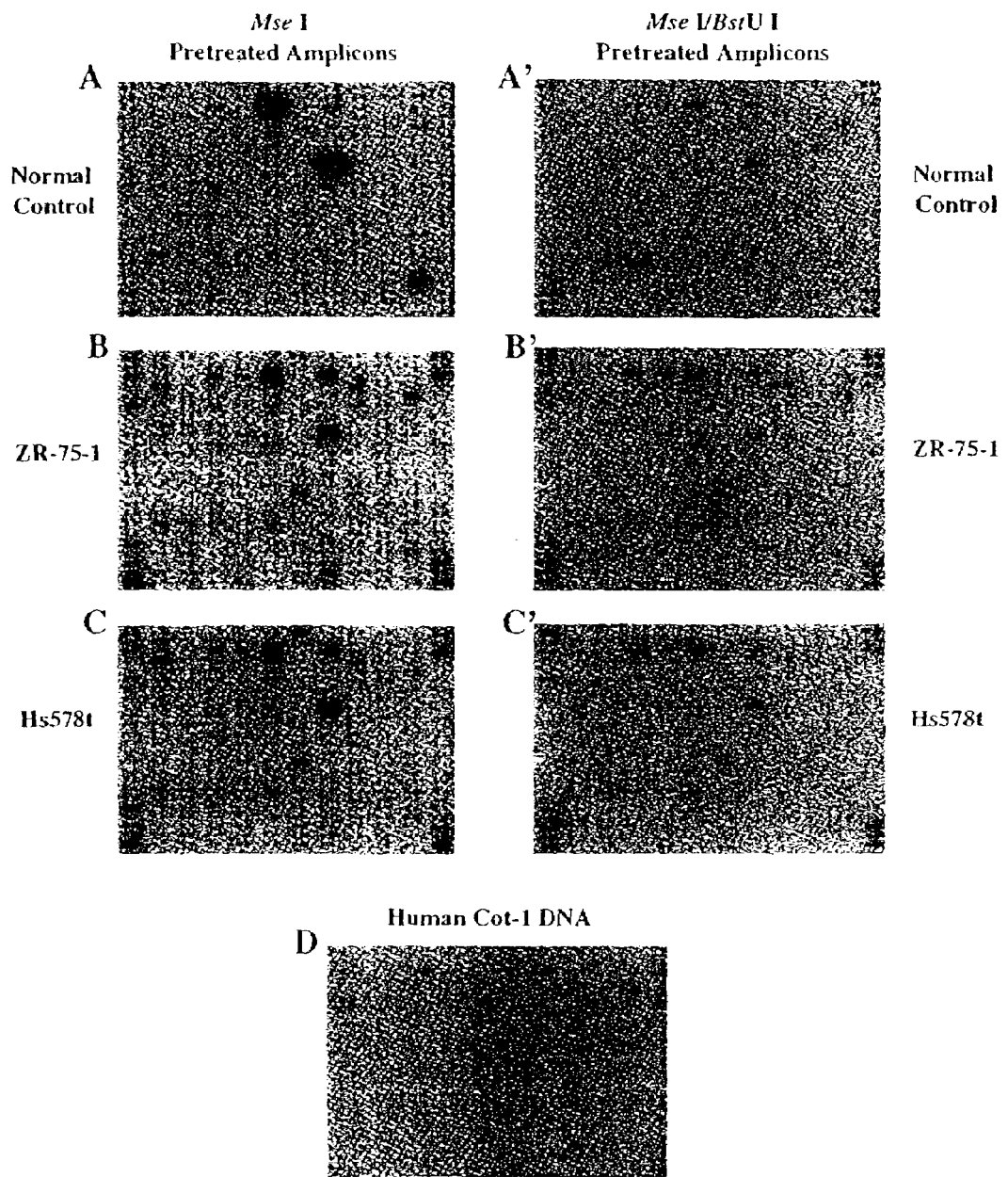
FIG. 4 shows representative results of differential methylation hybridization. PCR products of CpG island clones were dotted onto membranes in duplicate and hybridized first with $^{32}$P-labeled Mse I-pretreated amplicons as shown here for a normal breast sample (control), ZR-75-1, and Hs578t breast cancer cell lines (panels A, B, and C). The same membranes were later hybridized with $^{32}$P-labeled Mse I/BstU I-pretreated amplicons (panels A', B' and C'). Panel D: the membrane was hybridized with a repetitive DNA probe, human Cot-1 DNA (Gibco/BRL). Three positive control DNA samples were dotted in quadruplicate on the four corners of array to serve as orientation marks and for comparison of hybridization signal intensities.

Results of DMH analysis. FIG. 4 shows the representative results of 276 CpG island loci analyzed by DMH. Various degrees of hybridization signals observed could be attributed to different sizes of amplified products. Mse I-pretreated amplicons were expected to hybridize the matching Mse I-restricted CpG island sequences on the membranes; the hybridization signals, however, were detected in approximately 86% of these island loci (panels A, B, and C). The unhybridized loci could be derived from the Y chromosome due to the fact that this CGI library was originally constructed using male DNA, whereas the amplicons were prepared from female cells. Excluding the unhybridized loci (panel A) and the 14 Cot-1 positive loci (panel D), the Mse I/BstU I-pretreated amplicons derived from a normal breast tissue sample detected positive hybridization signals in 9.7% (23 of 237 loci) of the tested CpG island sequences (panel A'). The positive signals represent methylated BstU I sites located within these CpG island loci, some of which could be derived from the transcriptionally inactivated X chromosome or "imprinted genes." This low percentage is consistent with the notion that the majority of CpG islands are unmethylated in normal cells. A few prominent hybridization signals were observed on the filter hybridized with Mse I-pretreated amplicons (panel A); the intensity of these signals, however, was decreased on the filter hybridized with Mse I/BstU I-pretreated amplicons (panel A'). This may be attributed to the presence of some abundant sequences (e.g., ribosomal DNA or Cot-1 related sequences) known to be methylated in the normal genome.

Figure 5:
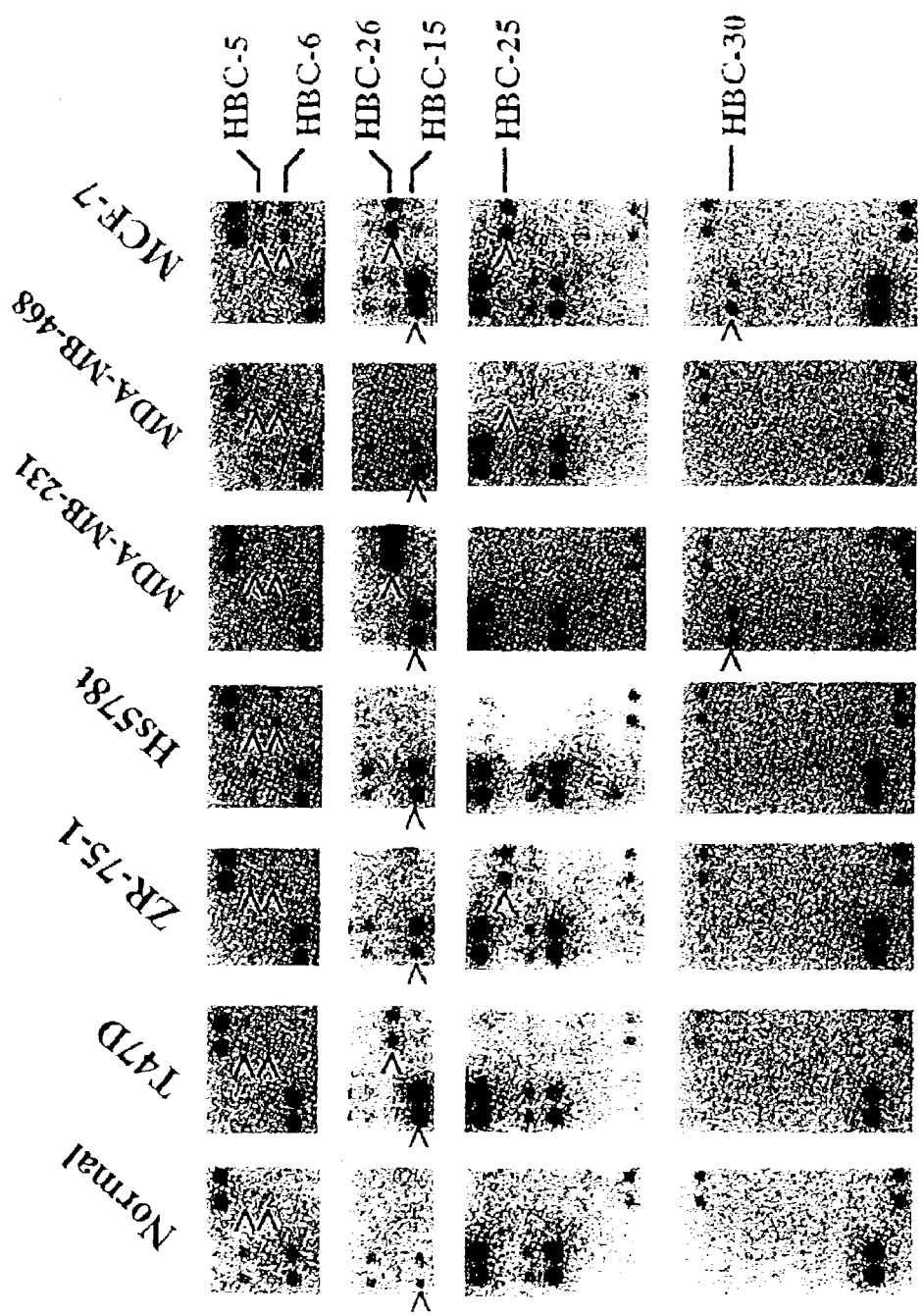
FIG. 5 represents identification of hypermethylated CpG island loci by differential methylation hybridization. PCR products of CpG island clones were dotted onto membranes in duplicate and probed with the Mse I/BstU I-pretreated amplicons for the normal control and breast cancer cell lines as indicated. Probes were prepared as described in the text. Clones shown at right (also marked by >) containing hypermethylated BstU I sites were identified on the autoradiogram showing greater hybridization signal intensities of dots hybridized with probes prepared from the breast cancer cell lines than the same dots probed with the normal breast control.

An increased number of hybridization signals were detected in the CpG island arrays hybridized with the Mse I/BstU I amplicons derived from the 6 breast cancer cell lines. Representative results were shown for cell lines ZR-75-1 and Hs578t (panels B, B', C, and C'). Methylated BstU I sites were observed in 15.0% of these tested loci in Hs578t, 15.6% in T47D, 18.0% in MDA-MB-468, 19.4% in ZR-75-1, 22.7% in MDA-MB-231, and 23.6% in MCF-7 cells, respectively. Although hypermethylation was extensive relative to the normal breast sample, the overall levels varied among these cell lines. Methylation pattern analysis led to the identification of hypermethylated CpG island loci present in these cell lines relative to the normal control; some loci appeared to be methylated in all 6 cell lines, whereas others were sporadically methylated in only a few cell lines (FIG. 5).

Nucleotide sequencing of hypermethylated CpG island loci. Thirty-four positive CpG island loci selected from the 276 CpG island array and from other DMH screenings were further characterized by nucleotide sequencing. Inserts of these CGI clones were sequenced and internal BstU I sites were verified. The sequence data were used to search for known sequences in the GenBank database. Thirty of these loci are listed in Table II. (Four other loci not listed here were false-positive findings; their hypermethylation status in breast cancer cells was not confirmed by subsequent Southern analysis.). Nine of the 30 clones contained sequences identical to the known expressed sequences of HPK1, DCIS1, potassium channel protein, PAX2, PAX7, GALNR2, EST03867, ESTAA827755, and EST88248. Six clones matched existing CpG island sequence tags.

TABLE 1

A list of positive CpG Island clones isolated by differential methylation hybridization

| CpG Island Clone | Insert Size (kb) | GenBank Match | ATCC Accession Number | SEQ ID NO |
|---|---|---|---|---|
| HBC-3 | 0.25 | | | 1 |
| HBC-4 | 0.90 | | | 2 |
| HBC-5 | 0.40 | DCISI | L27636 | 3 |
| HBC-6 | 0.80 | CGI Clone 28fl1 | Z60565 | 4 |
| HBC-7 | 0.60 | CGI Clone 178c6 | Z59859 | 5 |
| HBC-8 | 0.38 | CGI Clone 200b9 | Z55140 | 6 |
| HBC-9 | 0.44 | HPK1 | U66464 | 7 |
| HBC-10 | 0.75 | K + Channel Protein | Z93016 | 8 |
| HBC-11 | 0.70 | | | 9 |
| HBC-12 | 0.50 | CGI Clone 86e9 | Z63556 | 10 |
| HBC-13 | 1.00 | CGI Clone 31g5 | Z60696 | 11 |
| HBC-14 | 0.70 | | | 12 |
| HBC-15 | 1.50 | CGI Clone 7c5 | Z66179 | 13 |
| HBC-16 | 1.00 | EST AA827755 | ESTAA827 | 14 |
| HBC-17 | 0.75 | | | 15 |
| HBC-18 | 1.30 | PAX2 | M89470 | 16 |
| HBC-19 | 0.90 | PAX7 | AL021528 | 17 |
| HBC-20 | 0.45 | CGI clone 67g9 | Z62363 | 18 |
| HBC-21 | 0.90 | | | 19 |
| HBC-22 | 0.45 | | | 20 |
| HBC-23 | 0.90 | | | 21 |
| HBC-24 | 1.10 | IMAGE:2518953 5'mRNA | AI928953 | 22 |
| HBC-25 | 0.70 | | | 23 |
| HBC-26 | 0.70 | GALNR2 | AF058762 | 24 |
| HBC-27 | 0.70 | | | 25 |
| HBC-28 | 0.60 | | | 26 |
| HBC-29 | 0.70 | | | 27 |
| HBC-30 | 0.80 | | | 28 |
| HBC-31 | 0.50 | EST 03867 | T05978 | 29 |
| HBC-32 | 0.60 | EST88248 | T35610 | 30 |
| HBC-34 | 0.95 | IMAGE:1113203 3'mRNA | AA604922 | 31 |
| HBC-37 | 1.00 | PAC 163M9 | AL021920 | 32 |
| HBC-38 | 0.50 | CGI 40c10 | Z58446 | 33 |
| HBC-39 | 0.60 | EST185442 | AA313564 | 34 |
| HBC-41 | 0.60 | CGI 29h6 | Z58110 | 35 |
| HBC-42 | 0.50 | CGI 13f7 | Z56764 | 36 |
| HBC-43 | 0.80 | Genomic Clone NH0444B04 | AC007392 | 37 |
| HBC-45 | 0.50 | PAC 29K1 | Z98745 | 38 |
| HBC-46 | 0.65 | IMAGE:2177671 3'mRNA | AI500696 | 39 |
| HBC-48 | 1.50 | BAC CLONE RG300E22 | AC004774 | 40 |
| HBC-49 | 0.50 | CGI 40c10 | Z58447 | 41 |
| HBC-51 | 0.70 | COL9A1 (alt exon1) | M32133 | 42 |
| HBC-52 | 0.60 | IMAGE:2092259 3'mRNA | AI381934 | 43 |
| HBC-53 | 0.80 | Genomic Clone NH0444B04 | AC007392 | 44 |
| HBC-55 | 0.80 | CAVEOLIN-1 (exon2) | AF095592 | 45 |
| HBC-57 | 0.90 | GATA-3 (exon1) | X55122 | 46 |

EXAMPLE 4

Figure 6:
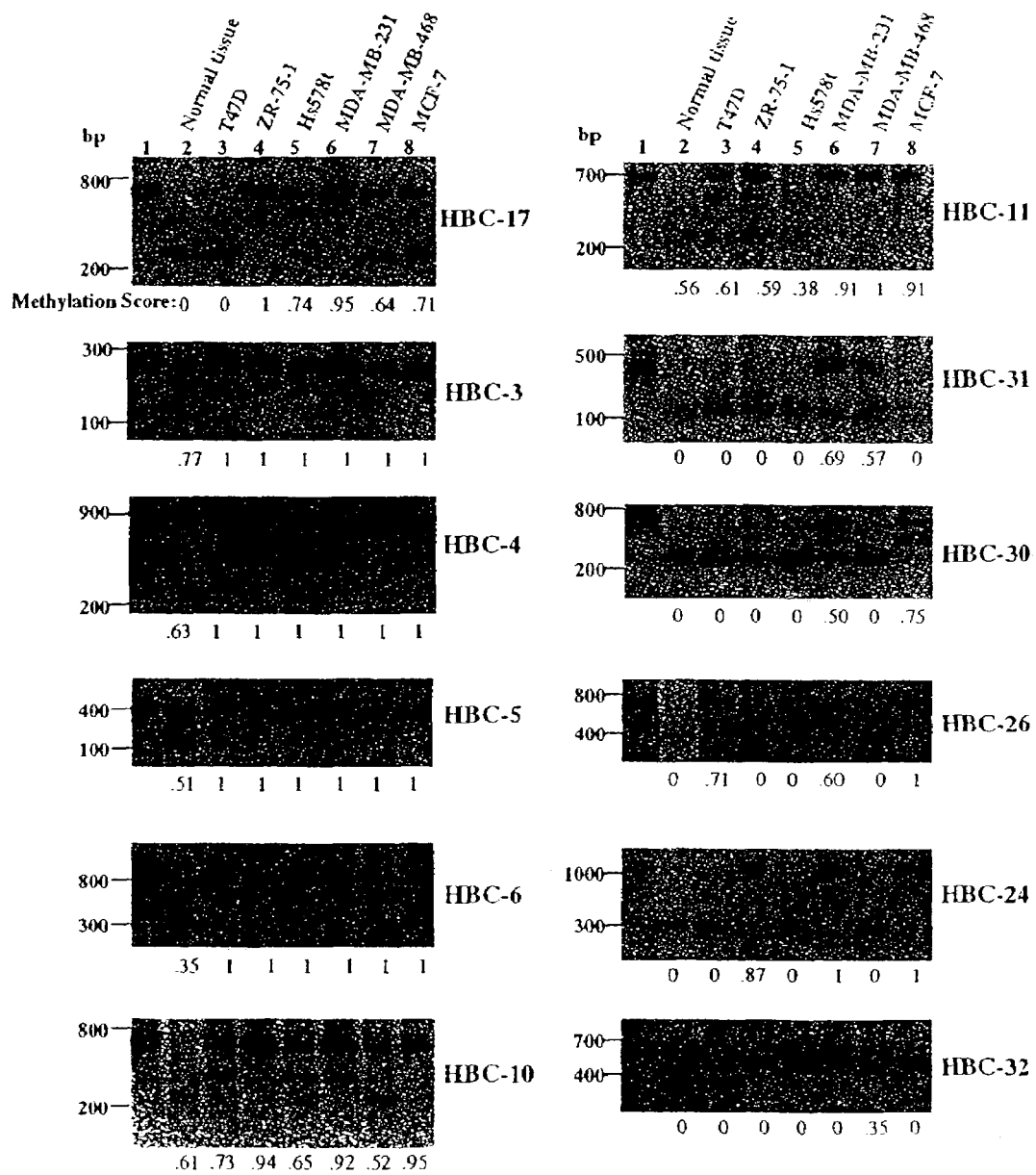
FIG. 6 shows representative results of methylation analysis by Southern hybridization. Genomic DNA (10 mg) from a normal breast tissue sample (lane 2) and breast cancer cell lines—T46D (lane 3), ZR-75-1 (lane 4), Hs578t (lane 5), MDA-MB231 (lane 6), MDA-MB-468 (lane 7), and MCF-7 (lane 8) were treated consecutively with Mse I and methylation sensitive BstU I, and subjected to Southern hybridization. Lane 1 contains control DNA digested with Mse I only. The digests were hybridized with genomic fragments (200-300-bp) derived from CpG island clones shown at right. Molecular weight markers (100-bp ladder; Promega) are shown at left. Percent of methylation was calculated as the intensity of the methylation band relative to the combined intensities of all bands. Percent of incomplete methylation was similarly calculated. The methylation score shown at the bottom of each lane was the sum total of the percent of complete methylation multiplied by 0.5.

Profiling Methylation Patterns of CpG Island Loci in Breast Cancer Cells by Southern Hybridization The methylation status of CpG island loci detected in the cancer cell lines was independently confirmed by Southern analysis (FIG. 6). Hybridization probes were generated from the cloned inserts by PCR. Amplified products were designed to be ~200 to 300-bp in length and contain no BstU I sites. For example, the probe for HBC ("hypermethylation in breast cancer") –17 (SEQ ID NO:15) detected a 750-bp fragment in the Mse I-digested, control DNA lane (top left panel, lane 1). The same or similar-sized fragments were detected in the Mse I/BstU I double-digested DNA samples of ZR-75-1, Hs578t, MDA-MB-231, MDA-MB-468, and MCF-7 (lanes 4-8). The presence of this fragment was a result of all the BstU I sites within HBC-17 (SEQ ID NO:15) being insensitive to restriction and, therefore, methylated in these cells. A 300-bp fragment was present in the T47D DNA 20 sample (lane 3). This band was shown in the digested normal, control DNA (lane 2), suggesting all the tested sites were unmethylated in the cells and digested by BstU I to give a 300-bp fragment. The unmethylated fragment was also present in MDA-MB-468 and MCF-7 cells (lanes 7 and 8). Partially methylated fragments (400 and 600-bp) were identified in Hs578t or MDA-MB-231 cells, which can be attributed to a portion of the tested BstU I sites being methylated in HBC-17 (SEQ ID NO:15).

Because it was not possible to measure the degrees of methylation at each tested site based on this Southern analysis, a semiquantitative approach was developed for these samples. First, percent of complete methylation was calculated as the densitometric intensity of the 750-bp fragment relative to the combined intensities of all fragments from each lane. Percent of incomplete methylation (i.e., the 400 and 600-bp fragments) and unmethylation (i.e., the 300-bp fragment) was similarly calculated. Each fraction was further assigned a value, with complete methylation being 1, incomplete methylation 0.5, and unmethylation 0. The methylation score for each sample was the sum total of the percent of complete methylation multiplied by 1 plus the percent of incomplete methylation multiplied by 0.5. The scores derived using this method were in agreement with the results based on a visual comparison of band intensities for each sample lane.

This approach was applied for the rest of the CpG island loci. Additional examples of Southern hybridization and the resulting methylation scores are shown in FIG. 6. To ensure a complete methylation-sensitive restriction of the cell line DNA samples, membranes were rehybridized with a negative control probe, 7-120, whose corresponding BstU I sites were known to be unmethylated in the cell line DNA as well as in a few normal breast DNA samples.

Figure 7:
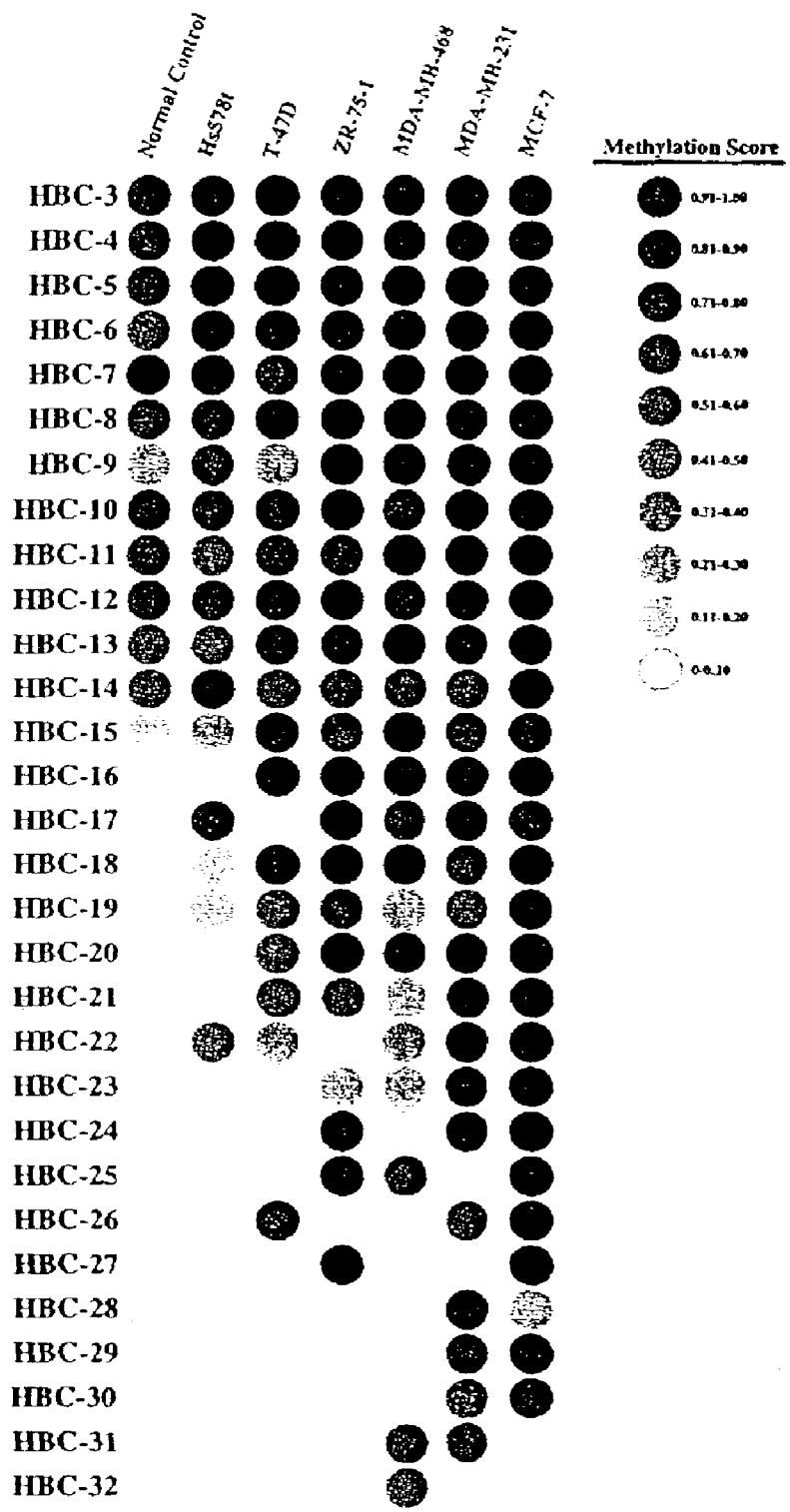
FIG. 7 is the methylation pattern analysis of 30 CpG island loci in breast cancer cell lines. Gray scales shown at right represent methylation scores of the 30 CpG island loci analyzed by Southern analysis (see examples in FIG. 5). The breast cancer cell lines indicated were arranged from left to right according to their increased methylation abilities (i.e., % of hypermethylated loci). The normal control was shown at the far left. Thirty CpG island loci (HBC-3 to -32 (SEQ ID NO:1 through SEQ ID NO:30); Huang, T. H.-M. et al., *Hum. Mol. Genet.*, 8:459-470, 1999; and applicant's U.S. Ser. No. 09/497,855, filed 4 Feb. 2000, Notice of Allowance received 7 Mar. 2003, and incorporated by reference herein in its entirety) were listed from top to bottom according to their increased methylation scores (ranges: 0-0.10, 0.11-0.20, 0.21-0.30, 0.31-0.40, 0.41-0.50, 0.51-0.60, 0.61-0.70, 0.71-0.80, 0.81-0.90, and 0.91-1.00 as indicated in the right column of the figure) derived from these cell lines.

Methylation scores of the 30 CpG island loci analyzed in the breast cancer cell lines and 1 normal control sample are summarized in FIG. 7. These cell lines are arranged from left to right according to their increased methylation abilities (i.e., % of hypermethylated loci), and the CpG island loci are listed from top to bottom according to their increased methylation scores derived from these cell lines. Methylation pattern analysis indicated that CpG islands might differ in their susceptibility to hypermethylation in these breast cancer cells. In loci HBC-3 to -15 (SEQ ID NO:1 to SEQ ID NO:13), various degrees of methylation at the tested BstU I sites were seen in the normal control sample. This pre-existing methylation condition was also observed in additional normal breast samples tested (data not shown). Hypermethylation of these loci appeared to be present and extensive in all the 6 cell lines examined. In contrast, hypermethylation in other loci, HBC-16 to -32 (SEQ ID NO:14 to SEQ ID NO:30), not displaying detectable pre-existing methylation in the normal control appeared to be less frequent in these cell lines. In some cases (e.g., HBC-23 to -32 (SEQ ID NO:21 through SEQ ID NO:30)), hypermethylation was observed only in a few cell lines. This observation suggests that a trend exists in which CpG island loci associated with the pre-existing condition are inclined to de novo methylation in cancer cells. Pattern analysis also revealed that the overall methylation frequencies were varied among these cell lines. Methylation (methylation score greater than 0.1) was observed in 57% of these 30 loci in Hs578t, 67% in T47D, 77% in ZR-75-1, 80% in MDA-MB-468, 90% in MDA-MB-231, and 93% in MCF-7 cells, respectively. These differences were more obvious by comparing methylation patterns among the loci HBC-16 to 32 (SEQ ID NO:14 to SEQ ID NO:30), not exhibiting the detectable pre-existing condition. In the two extreme cases, for example, only 4 of these 17 loci showed detectable methylation in Hs578t cells, whereas 15 of these loci had extensive methylation in MCF-7 cells. The results suggest that these cell lines differ in their intrinsic abilities to methylate CpG island sequences.

EXAMPLE 5

Methylation Analysis of Primary Breast Tumors by Southern Hybridization

Figure 8:
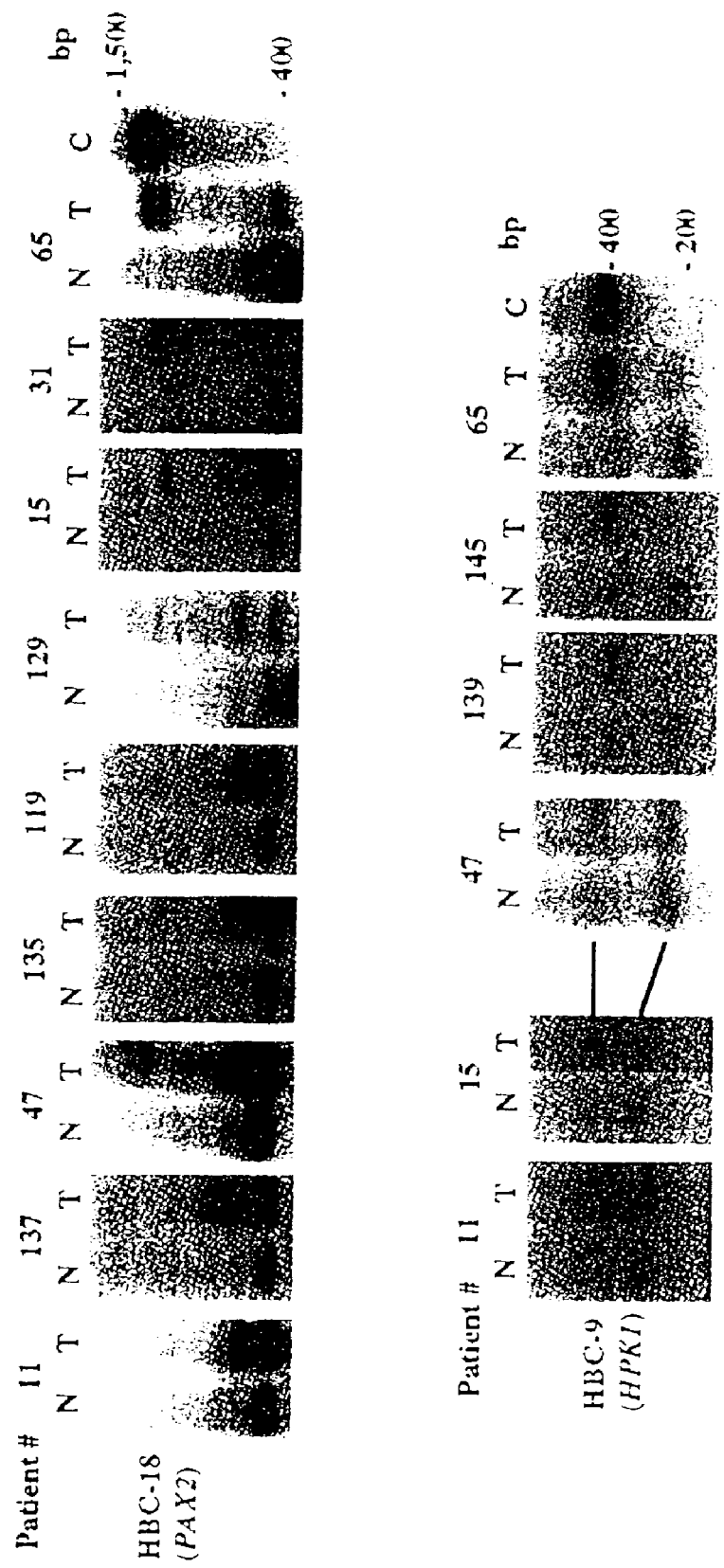
FIG. 8 is the methylation analysis of HBC-18 (SEQ ID NO:16) and -9 (SEQ ID NO:7) by Southern blot hybridization. Genomic DNA (10 μg) of breast tumor and the matching normal tissue was treated consecutively with Mse I and methylation-sensitive BstU I and subjected to Southern hybridization using the cloned genomic fragments as probes. These CpG island clones (HBC-18 (SEQ ID NO:16) and -9 (SEQ ID NO:7)) contained sequences identical to the 5' end of PAX2 (paired box-containing gene 2) and the promoter and exon 1 of HPK1 (hematopoietic progenitor kinase gene 1), respectively. "C" indicates control DNA digested with Mse I only, "T" refers to breast tumor, and "N" refers to normal breast tissue. Patient numbers are shown at the top of lanes. Molecular weight markers (100 bp ladder; Promega) are shown at right. Corresponding reference characters indicate corresponding parts throughout the several views of the drawings.

It has been demonstrated that CpG islands associated with nonessential genes might become methylated over time in immortalized cells that have been in culture for many years. See Antequera et al., *Cell* 62: 503-514 (1990). The question of whether the in vitro findings could represent bona-fide de novo methylation in primary breast tumors was investigated. The methylation status of 9 CpG island loci: HBC-6 (SEQ ID NO:4); HBC-8 (SEQ ID NO:6); HBC-9 (SEQ ID NO:7); HBC-12 (SEQ ID NO:10); HBC-15 (SEQ ID NO:13); HBC-18 (SEQ ID NO:16); HBC-20 (SEQ ID NO:18); HBC-22 (SEQ ID NO:20); and HBC-23 (SEQ ID NO:21) were validated in primary breast tumors by Southern hybridization. As shown in FIG. 8, upper panel, HBC-18 (SEQ ID NO:16), was hypermethylated in the tumor DNA samples of patients 47, 135, 119, 129, 15, 31, and 65 relative to their paired normal breast tissue. Incomplete methylation of HBC-18 (SEQ ID NO:16) loci was detected in tumors of patients 11 and 137. In FIG. 8, lower panel, pre-existing methylation of HBC-9 (SEQ ID NO:7) was observed in the normal breast tissue of these patients consistent with the previous observation (FIG. 7). Hypermethylation of HBC-9 (SEQ ID NO:7) was observed in the tumor lanes of patients 47, 139, 145, and 65, showing increased band intensity of the 440-bp fragment relative to that of the same band in normal lanes. On preliminary observation, de novo methylation of two loci, HBC-16 (SEQ ID NO:14) and HBC-26 (SEQ ID NO:24) was not present in 2 primary breast tumors.

Comparisons of methylation patterns among the cell lines and a normal control indicate that the 30 CpG island loci might differ in their propensity for de novo methylation. This inherent condition may be at least in part influenced by a pre-existing methylation condition in local genomic sequences. As described in EXAMPLE 4, loci HBC-3 to -15 (SEQ ID NO:1 to SEQ ID NO:15) seemed to be more susceptible to de novo methylation as compared to other loci (FIG. 7). Normal breast samples had detectable methylation in this group of CpG islands; methylation of these loci appeared to be extensive to complete in the cancer cell lines examined. In contrast, other loci without this pre-existing condition were less inclined to de novo methylation in breast cancer cells. This observation suggests that pre-existing methylation within a CpG island locus may promote subsequent de novo methylation in cancer cells.

This observation is further supported by several previous in vitro findings, showing that the activity of DNA-MTase could be positively influenced by a partial pre-methylation condition (see Christman et al., *Proc. Natl. Acad. Sci. USA*, 92: 7347-7351 (1995); Carotti et al., *Biochem. J.*, 37: 1101-1108 (1998)). These studies found that single- or double-stranded synthetic polymers were poor substrates of the eukaryotic DNA-MTase, yet were efficiently methylated by the enzyme following the introduction of a small number of 5-methylcytosines by a prokaryotic methylase. Carotti et al. showed that the presence of 5-methylcytosines in double-stranded DNA substrates, either of natural or synthetic origins, stimulated in vitro methylation of neighboring CpG dinucleotides by DNA-MTase (Carotti et al., supra). The extent of stimulation depended both on the number and the distributions of the 5-methylcytosine residues, which could not be spaced too closely to exert the effect. This phenomenon has also been observed in human fibroblast cells transfected with a DNA-MTase cDNA (see Vertino et al., *Mol. Cell Biol.*, 16:4555-4565 (1996)). CpG island loci that were subject to de novo methylation in the transfected clones overexpressing DNA-MTase had low, but detectable levels of methylation in the parental lines. In contrast, CpG island loci found to be resistant to methylation in these transfected clones were devoid of methylation in the parental line.

This methylation-spreading phenomenon can account for the extensive methylation in CpG island loci with the pre-existing condition. It has been suggested that during tumorigenesis, pre-existing methylated repetitive elements may act as de novo methylation centers (i.e., cis-acting signals) from which methylation spreads into adjacent CpG island sequences. The results of these experiments indicate that methylation spread may actually occur from within a CpG island sequence in tumor cells. The existing 5-methylcytosine residues in the sequence may stimulate the de novo methylation function of DNA-MTase. Although DNA-MTase prefers hemimethylated substrates for its maintenance activity in normal cells, the enzyme may have a second regulatory domain "sensing" the presence of 5-methylcytosines within CpG island sequences, allowing for de novo methylation. The "sensing" function could become more operative due to aberrantly high DNA-MTase levels in tumor cells. This may in turn lead to de novo methylation of cytosines located near sequences already containing methylated CpG dinucleotides. The newly methylated sites may acquire the ability to stimulate the subsequent methylation of adjacent sequences via DNA-MTase. This "domino" effect of methylation could progress with time to include the entire CpG island region, leading to the associated transcriptional silencing.

Differential methylation abilities in breast cancer cell lines. A second characteristic of our findings was that these breast cancer cell lines exhibited differential methylation potentials. In the two extreme cases, Hs578t and MCF-7 cells, the former showed a lack of ability to methylate the CpG island group HBC-16 to -32 (SEQ ID NO:14 to SEQ ID NO:30) without the pre-existing condition described above whereas the latter was proficient in methylating these CpG island loci. This suggests that the observed differences among these cell lines could not be solely due to the aberrant DNA-MTase action. The degrees of methylation appeared not to be correlated with the increased levels of DNMT1 expression or with the decreased levels of $p21^{WAP1}$ expression observed in these cells (FIGS. 1 and 7).

Thus, these results indicate that additional cellular factors may govern CpG island hypermethylation. One possibility may be an as yet unidentified or uncharacterized gene encoding a de novo methylase. Another possibility is that the various degrees of de novo methylation observed in these cancer cells might simply result from fixation of a hypermethylator phenotype that affords a greater proliferation potential. Finally, differential methylation abilities could be related to deficiencies in DNA repair in these cell lines.

EXAMPLE 6

DMH was Use to Screen and Analyze Breast Cancer Tumors

The likelihood of potential mechanisms governing methylation in breast cancer cells by pattern analysis was demonstrated. DMH was then applied to determine whether patterns of specific epigenetic alterations correlate with pathological parameters in the patients analyzed.

Isolation of Amplicons from Breast Tumor DNA. DHM was used to analyze breast tumor specimens obtained from 28 female patients undergoing mastectomies at the Ellis Fischel Cancer Center (Columbia, Mo.) between 1992 and 1998. Adjacent, normal parenchyma was obtained from the same patient to serve as a normal control. All tumors used in this study were classified as infiltrating ductal carcinomas and were graded based on the Nottingham modified criteria of Bloom and Richardson (see Bloom, H. J. G. and Richardson, W. W., *Br. J. Cancer* 9: 359-377 (1957)). This tumor-grading method was based on histological features of tubule formation, nuclear pleomorphism, and mitotic activity, and points were assigned for each category accordingly. The overall tumor grade was the sum total of scores between 3-9. Tumors with poorly differentiated phenotypes (8-9 points) are likely to have less or no tubular structures, irregular and large nuclei, and high mitotic counts. Tumors with moderately (6-7 points) or well differentiated (3-5 points) phenotypes may have definite tubule formation, moderate outlines of epithelial cell shapes and uniformity of nuclear chromatin, and low mitotic indexes. High-molecular-weight DNA was isolated from these specimens using QIAamp™ Tissue KitJ (Qiagen).

DMH was performed as provided in the materials and methods of EXAMPLE 1. Genomic DNA (0.5-1 μg) from breast tumor or normal samples was utilized to prepare the amplicons as described in Example 1. The amplified products, labeled as normal or tumor amplicons, were purified and $^{32}$P-labeled for array hybridization. BstUI-positive, Cot-I-negative or -weakly positive CpG island clones were prepared from the CGI genomic library and used for 96-well format PCR as described in EXAMPLE 1. Membranes were first hybridized with normal amplicons, and autoradiography was conducted using the Molecular Dynamics PhosphorImager. Probes were stripped and the same membranes, or duplicate membranes, were hybridized with tumor amplicons and scanned with the PhosphorImager.

Data Analysis. Dot intensities for positive CpG island tags were measured using the volume review protocol of ImageQuant™ software (Molecular Dynamics). The raw volume data from tumor and normal samples were normalized prior to comparison. This was achieved by ratio determination of the internal control tags. Briefly, two internal control tags with close volume ratios were selected to estimate hybridization differences between paired amplicons. One of these two control tags from each amplicon was further used to calculate a factor for normalization:

$$\text{Normalization factor} = \frac{\text{Normal internal control tag volume}}{\text{Tumor internal control tag volume}}$$

This factor was applied to normalize tumor tag volumes. For tags with preexisting methylation in normal tissue, the normal tag volume was subtracted from the normalized tumor volume. For tags without preexisting methylation in the normal tags, the normalized tumor volume was used directly. Statistical analyses were performed using the SigmaStat software (version 2.0). The hypermethylation differences among different groups of tumor grades were determined by the unpaired t-test and by the Mann-Whitney rank sum test when the data failed the normality test. The difference was considered significant when the P value was less than 0.05.

Figure 9:
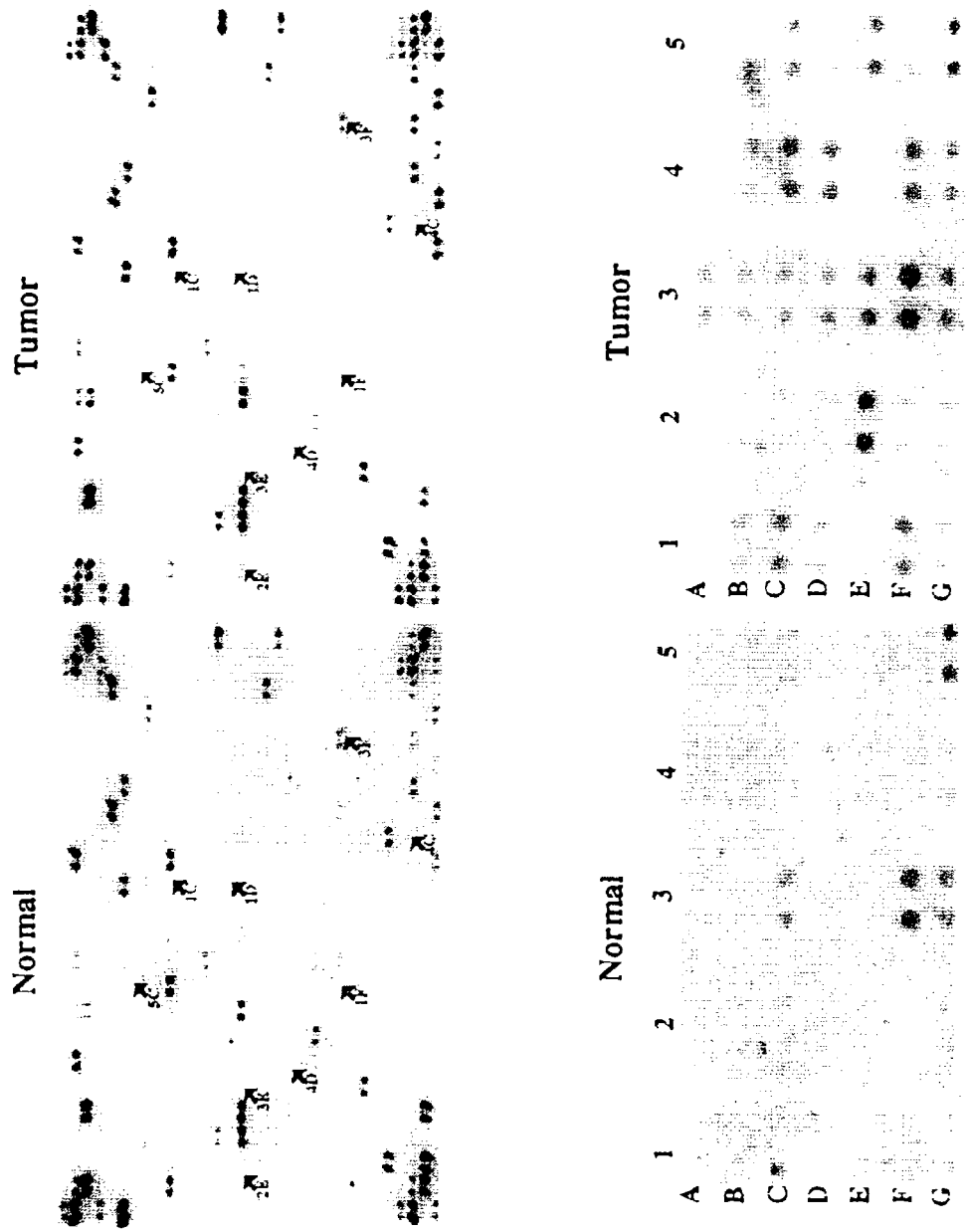
FIGS. 9A and 9B show representative results of DMH (differential methylation hybridization) from one breast cancer patient.

Results and Discussion. DMH was initially applied to 28 paired breast tumor and normal samples using an array panel containing more than 1,000 CpG island tags. FIG. 9A shows representative results of DMH screening in paired normal and tumor samples of patient 103. Based on visual inspection, hypermethylated sequences were identified in breast tumors, showing detectable hybridization signals in CpG island tags probed with tumor amplicons, but not in the same tags probed with normal amplicons (see examples indicated by arrows). This is because methylated BstUI sites in tumor DNA were protected from restriction within CpG island sequences, which were then amplified by linker-PCR and hybridized to the corresponding tags. The same sites, however, were unmethylated or partially methylated in normal DNA and were restricted by BstUI; therefore, no hybridization signals were detected in the arrays. Some of these hypermethylated CGI island tags were confirmed in the subsequent secondary screening (FIG. 9B).

A few CpG island tags were detected by normal amplicons (i.e., preexisting methylation) but showed greater signal intensities when probed with tumor amplicons (e.g., CpG island tags on the lower right hand corner in FIG. 9A). These sequences usually exhibited more prominent hybridization signals among all of the tags, likely representing abundant copies of CpG dinucleotide rich ribosomal DNA as previously described in the cell line study. Methylation of ribosomal DNA has previously been observed in normal cells, but shown to increase to a greater extent in breast tumors. Another possibility is the increased copy numbers of normally methylated CpG island loci in tumors due to aneuploidy. Excluding this preexisting condition, the extent of hypermethylation in unmethylated CpG islands was quite variable among patients in this group; close to 9% of the tested BstUI sites exhibited complete methylation in some breast tumors examined while others had little or no detectable change in the tested sites.

Sequence Characterization of CpG Island Tags. Thirty CpG island tags positive for hypermethylation in the primary screening were selected for further characterization. DNA sequencing results showed that 9 of these tags contained sequences identical to known cDNAs, PAX7 (5' end), Caveolin-1 (exon2), GATA-3 (exon 1), and COL9A1 (exon 1), and 5 ESTs (AI928953, AA604922, AA313564, AI500696, and A1381934) as shown in Table 1.

This finding is consistent with that of Lisanti and coworkers where they also observed CpG island methylation in the Caveolin-1 gene in breast cancer cell lines. Five CpG island tags: HBC-17 (SEQ ID NO:15); HBC-19 (SEQ ID NO:17); HBC-24 (SEQ ID NO:22); HBC-25 (SEQ ID NO:23); and HBC-27 (SEQ ID NO:25), found to be hypermethylated in breast cancer cell lines as discussed in EXAMPLE 5 were also identified in this study. The remainder twenty-five tags were numerically assigned as HBC-33 to -57 (SEQ ID NO:31 to SEQ ID NO:46).

Secondary Screening of DMH in Breast Tumors. As shown earlier in FIG. 9B, the 30 CpG island tags were re-arrayed for secondary DMH screening in the patient group to confirm their hypermethylation status (see representative results in FIG. 10). Five additional tags—coordinates on the x- and y-axes are 3C, 3F, 3G, 4G, and 5G-showing no hybridization intensity differences among a few of the breast tumors tested in the primary screening were chosen as internal controls. Again, most normal controls showed few or no detectable hybridization signals at the tested loci, whereas the corresponding breast tumors exhibited various degrees of hybridization intensities, reflecting the differences in CpG island hypermethylation.

Figure 10:
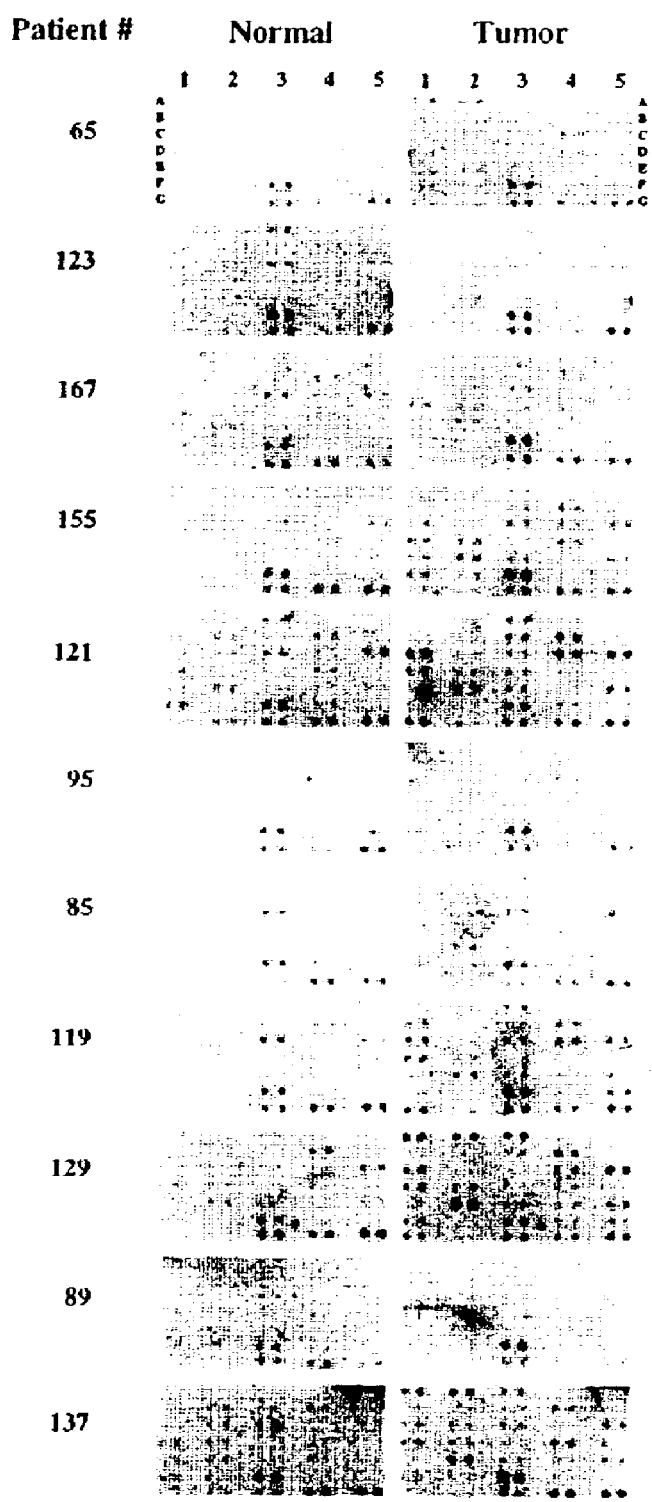
FIG. 10 shows identification of hypermethylated CpG island loci by DMH. The 30 CpG island tags shown in this subarray panel were selected from an initial DMH screening of >1,000 tags. Five additional tags having coordinates on the X- and Y-axes of 3C, 3F, 3G, 4G and 5G, were included as internal controls. CpG island tags were dotted onto membranes in duplicate and probed with radiolabeled amplicons corresponding to normal and breast tumors as indicated. DMH screening from 11 of 28 patients is represented, and experiments were performed independently at least twice.

To semiquantify the methylation differences, hybridization signal intensity for each CpG island tag was measured using the volume review protocol of ImageQuant™ software as described in "Materials and Methods" From FIG. 10, it is clear that dot intensities of the internal controls sometimes varied among patients or between a patient's paired tumor and normal samples, likely due to tissue heterogeneity or tumor aneuploidy. Therefore, internal control volume ratios were tested and two with close volume ratios were selected for normalization. The adjusted tumor volumes were used for clinical correlation in this patient group.

Figure 11:
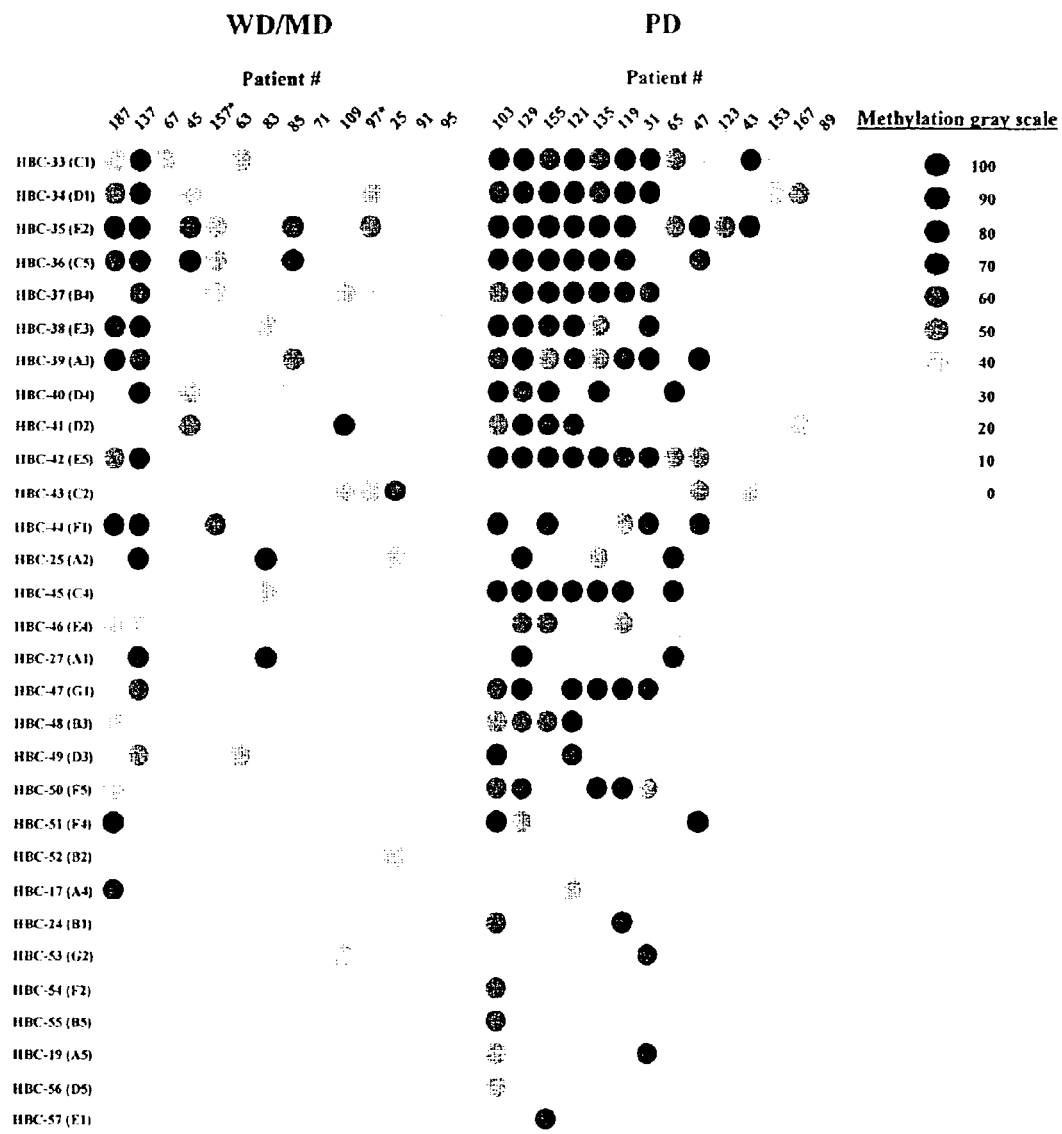
FIG. 11 shows the hypermethylation pattern analysis of 30 CpG island loci in 28 primary breast tumors. The reference methylation gray scale (0-100, in increments of 10) is shown at the right, and represents volume percentile generated by ranking hybridization signal intensities of these tested loci. Data from primary tumors were presented according to their tumor grades: well-/moderately differentiated (WD/MD), and poorly differentiated (PD). Within each group, patients were arranged from left to right according to their increased methylation propensities. Thirty CpG island loci (on the left of the panel with their secondary screening coordinates shown in parenthesis) were listed from top to bottom according to their increased methylation scales derived from the primary tumors. Additionally, five CpG island loci: HBC-17 (SEQ ID NO:15); HBC-19 (SEQ ID NO:17); HBC-24 (SEQ ID NO:22); HBC-25 (SEQ ID NO:23); and HBC-27 (SEQ ID NO:25) were found to be hypermethylated in breast cancer cell lines.

CpG Island Hypermethylation and Tumor Grades. Statistical analysis revealed that CpG island hypermethylation was associated with histological grades of breast tumors (P-0.041). To aid in visualizing differences in CpG island hypermethylation among different tumor grades, a gray scale was devised by categorizing tumor methylation volumes into percentiles as depicted in FIG. 11. The PD (poorly differentiated) group exhibited more frequent and extensive hypermethylation at the loci tested than their MD/WD (well-/moderately differentiated) counterparts did; half of the 14 PD tumors showed extensive hypermethylation at multiple loci (>10), while only two of the 14 MD/WD tumors showed hypermethylation at these loci. Moreover, the greatest degrees of differences were seen at loci HBC-42 (SEQ ID NO:36), HBC-45 (SEQ ID NO:38), and HBC-47 that were frequently hypermethylated in PD tumors, but not in MD/WD. This result suggests that patients with more advanced disease status are prone to methylation alterations. It should be noted that some of the patients showed little or no changes of methylation at the loci tested. This indicates that progression of some tumors may be independent of this epigenetic event or the alteration could occur in later stages of tumor development in such patients. No association of hypermethylation with other clinical parameters was found in this study.

The results of these experiments indicate that differential methylation patterns observed in various clinical specimens may reflect different stages or types of cancer. In this case, the most common methylation of CpG island loci (e.g., HBC-33, -34 (SEQ ID NO:31), HBC-35, and HBC-36) observed among different tumor grades likely occurs early during tumor development, while methylation groups (e.g., HBC-42 (SEQ ID NO:36), HBC-45 (SEQ ID NO:38), and HBC-47) observed preferentially in PD, but not in WD/MD groups, occur in later stages.

In view of the above, it will be seen that the several objects of the invention are achieved. Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

EXAMPLE 7

Materials and Methods for Examples 7-12

Sample Preparation. The breast cancer cell line MDA-MB-231 was maintained as previously described (Laux, D. E., et al., Breast Cancer Res. Treat., 56:35-43, 1999) and was treated with 0.75 µM 5-aza-2'-deoxycytidine ("deoxyC") at an initial density of $2\times10^4$ cells/cm$^2$ for 4 days before harvesting. Control cultures were maintained in the absence of deoxyC. Breast tumor and tumor-free specimens were obtained from patients undergoing mastectomies or biopsies at Ellis Fischel Cancer Center, Columbia, Mo. (Institutional Review Board approval #7935). Genomic DNA and total RNA were isolated using the QIAAMP™ Tissue and RNEASY™ kits (Qiagen), respectively.

Preparation of CpG Island Microarrays. PCR products (on average 500-bp) of a microarray panel containing 7,776 CpG island clones were prepared as previously described (Yan, P. S., et al., Cancer Res. 61:8375-8380, 2001). Briefly, the resource material for preparing the microarray panel was derived from a CpG island library, CGI (Cross, S. H., et al., Nat. Genet., 6:236-244, 1994). CGI was previously prepared using male genomic DNA restricted with MseI, a four-base cutter known to restrict DNA into small fragments, but retain CpG island fragments largely intact (Id). The GC-rich MseI fragments were isolated through an affinity column containing methyl-binding MeCP2 protein and cloned into vector for library construction. A total of 7,776 CGI clones were individually organized in 96-well culture chambers as master plates. This included 10 pre-selected MseI-tags that act as positive controls because they are known to lack the test methylation-sensitive sites. A fraction (~1 µl) of each clone was transferred to a well of separate 96-well PCR tubes using the MULTI-PRINT™ replicator (V&P Scientific). CpG island inserts (0.2 to 2-kb) from these clones were amplified by PCR as described (Huang, T. H.-M. et al., Hum. Mol. Genet., 8:459-470, 1999). The primers immediately flanking the inserts are HGMP 3558: 5'-CGGCCGCCTGCAGGTCT-GACCATAA (SEQ ID NO:47) and HGMP 3559: 5'-AACGCGTTGGGAGCTCTCCCATAA (SEQ ID NO:48) (CGI) (Cross, S. H., et al., 1994, supra). To ensure the reproducibility of each PCR and to prevent cross-contamination among bacterial clones in microplates, amplified inserts were individually verified using a 96-well format gel electrophoresis system (Cascade Biologics). Preferably, the arrayer is the Affymetrix/GMS 417 Arrayer, and permits the dotting of unpurified PCR products, because its ring-and-pin system is much less susceptible to clogging than the quill-type pen and ink-jet type printing head. Unpurified PCR products (~0.02 µl per dot, 0.1 µg/µl), in the presence of 20% DMSO, were printed as microdots (150 µm diameter spaced at 300 µm) on poly-L-lysine-coated microscope slides as described in the website of DeRisi et al. (www.microarrays.org). Spotted DNA was denatured before use.

Preparation of Amplicons for Expression Analysis. One hundred µg total RNA was subjected to a treatment of calf intestinal phosphatase (New England Biolabs) followed by purification with Qiagen RNEASY™ column. This treatment removed 5' free phosphates from uncapped ribosomal RNAs, tRNAs, or fragmented mRNAs, and contaminating genomic DNAs, but retained the intact 5'-ends of capped mRNA. The cap structure of mRNAs was then removed by a subsequent treatment of tobacco acid pyrophosphatase, leaving a 5' monophosphate that still attached to mRNAs (Maruyama & Sugano, S., Gene, 138:171-174, 1994). A synthetic RNA adapter (0.5 nmol, 5'-ACCGGAGCGGCACGGGAAAUA-GAGCAACAGGAAA) (SEQ ID NO:55) was ligated to the 5'-ends of the mRNA population in the presence of T4 RNA ligase (Epicentre). This adapter, however, could not ligate to the dephosphorylated ribosomal RNA, tRNA, or fragmented mRNAs because they lack the 5' monophosphate necessary for ligation. Full-length cDNA was generated from ligated mRNAs by reverse transcription (SUPERSCRIPT II™ reverse transcriptase, Life Technologies) with a primer containing 17-nt polyT (5'-GGCCGACTCACTGCGCGTCT-TCTGTCCCGCCT$_{17}$) (SEQ ID NO:56) at 45° C. Long-PCR reactions (TAQPLUS™ Long PCR System, Stratagene) were performed using the 5'- and 3'-adapter primers: 5NEST: 5'-GCACGGGAAATAGAGCAACAG (SEQ ID NO:57) and 3RT: 5'-GGCCGACTCACTGCGCGTCTTCTG (SEQ ID NO:58). Low amplification cycles (18 cycles) were used to preserve the linearity of PCR. The amplified products (or amplicons) were purified for fluorescence labeling. Incorporation of amino-allyl dUTP (aa-dUTP) into amplicons (5 µg) was conducted using the BIOPRIME™ DNA Labeling System (Life Technologies). Cy5 and Cy3 fluorescence dyes were coupled to aa-dUTP-labeled test and reference amplicons, respectively, and co-hybridized to the CpG island microarray panel. Hybridization and the post-hybridization washing protocols were according to DeRisi et al. (http://www.microarrays.org). Hybridized slides were scanned with the GenePix 4000A scanner (Axon) and the acquired images were analyzed with the software GenePix Pro3.0.

Preparation of Amplicons for Methylation Analysis. Amplicon preparation for methylation analysis was followed as previously described (Huang, T. H.-M. et al., Hum. Mol. Genet., 8:459-470, 1999). Briefly, 2 µg genomic DNA was restricted with MseI, a 4-base TTAA endonuclease that restricts bulk DNA into small fragments (<about 200-bp), but retains GC-rich CpG islands. The sticky ends of the digests were ligated with 0.5 mmol PCR linkers H-24/H-12 (H-24: 5'-AGG CAACTGTGCTATCCGAGGGAT (SEQ ID NO:49) and H-12: 5'-TAATCCCTCGGA) (SEQ ID NO:50). Repetitive DNA was then removed from the ligated products using a subtractive hybridization technique (Craig, J. M. et al., Hum. Genet., 100:472-476, 1997). The subtracted DNA was further digested with the methylation-sensitive endonuclease HhaI. Additionally, without the subtraction step, DNA was directly digested with 2 methylation-sensitive endonucleases, HpaII and BstUI. Linker-PCR was performed using the digests as templates as described previously Huang, T. H.-M. et al., 1999, supra). The amplified products from both the single and double methylation-sensitive treatments were purified and used for aa-dUTP incorporation. The steps for fluorescence labeling, microarray hybridization, post-hybridization washing, and slide scanning were as described herein above.

Microarray Data Analysis. The Cy3 and Cy5 fluorescence intensities were obtained for each hybridized spot. Array spots with fluorescence signals close to the background signal, reflecting PCR or printing failures, were excluded from the data analysis. Because Cy5 and Cy3 labeling efficiencies varied among samples, the Cy5/Cy3 ratios from each image were normalized according to their global Cy5/Cy3 ratio as well as the average ratio of 14 internal controls, in which their normalized ratios were expected to be 1. This internal control panel included 2 different β-actin cDNA fragments (exons 1 and 3) and 2 different GAPDH cDNA fragments (exons 1 and 8) spotted at several concentrations on each array. The adjusted Cy5/Cy3 ratio for each ECIST locus was then calculated and data were exported in a spreadsheet format for analysis. A second microarray experiment was also performed by reversing the dye-coupling of test (Cy3) and reference (Cy5) amplicons. The acquired microarray data were then used to compare data derived from the first experiment. A quality control, self-hybridization study was also conducted in which 2 equal portions of a test DNA sample were labeled with Cy5 and Cy3, respectively, and co-hybridized to the microarray slide. For the statistical analysis of the gene expression data, we used a software package called SAM (significant analysis of microarray) (Tusher, V. G., et al., Proc. Natl. Acad. Sci. USA, 98:5116-5121, 2001). The 3 hybridization experiments (2 repeated and 1 self-hybridization) were used as inputs for analysis. The derived expression data were transformed to cube root to obtain a normal distribution before performing the analysis.

Nucleotide Sequencing. Plasmid DNA was prepared from ECIST clones and sequenced using the DyeDeoxy Terminator Cycle Sequencing kit (Applied Biosystems) and the automated ABI PRISM 377 sequencer. The resulting nucleotide sequences were then compared to the GenBank sequences, using the BLAST program (WWW.ncbi.nlm.nih.gov/BLAST).

Northern Hybridization. Premade northern blots (Clontech) containing 1 µg of poly A+ RNA per lane from 12 different human tissues were used to determine the presence of transcripts in ECIST loci. PCR products (Q200 bp) were generated from putative expressed sequences within the ECIST fragments and were $^{32}$P-labeled using the Multiprime DNA Labeling system (Amersham). The radiolabeled probes were used in northern hybridization. Post-hybridization washing was performed as described herein (Huang, T. H.-M., et al., 1999, supra). The hybridized blots were then exposed in a PHOSPHORIMAGER™ (Molecular Dynamics) and the results were analyzed using IMAGEQUANT™ software (Molecular Dynamics).

5'-RACE. This PCR method was used to amplify the 5'-end of a transcript. The RNA ligase-mediated cDNA synthesis described earlier was used to prepare full-length cDNAs as templates. PCR was conducted using a locus-specific primer (3'-end) and the previous 5'-adapter primer, 5NEST. Five locus-specific primers used in 5'-RACE were: GAPDH: 5'-CGC TCC TGG AAG ATG GTG A (SEQ ID NO:59); β-actin: 5'-CGC AGC TCA TTG TAG AAG GTG TGG (SEQ IN NO:60); CpG6B6: 5'-TGT TGC TGG GGT ACA TGT TG (SEQ ID NO:61); PY2F1: 5'-GGA TTG GAC ACC ATT GCA GCC G (SEQ ID NO:62); and SC13D6: 5'-AAC CAT TTG CCA ATA CTT TCA TTT (SEQ ID NO:63). PCR products were electrophoresed through 1% agarose gels.

Southern Hybridization. For confirmation of the methylation status of ECISTs identified by microarray experiments, 10 µg of genomic DNA from MDA-MB-231 cells or patients' specimens were digested to completion with MseI a lone or followed by methylation-sensitive endonucleases BstUI, HhaI, or HpaII (New England Biolabs). The digestions were performed as per the supplier's protocols. The restriction products were electrophoresed on a 1% agarose gel and transferred to a nylon membrane. Membranes were hybridized with probes (200 to 300-bp) prepared from the CpG island clones by PCR. Prehybridization, hybridization, and washing were performed as previously described (Huang, T. H.-M., et al., 1999, supra). Membranes were exposed in a PHOSPHO- RIMAGER™ (Molecular Dynamics) and the results were analyzed using IMAGEQUANT™ software (Molecular Dynamics).

RT-PCR. For each sample, 1-4 µg of total RNA was reversibly transcribed using the SUPERSCRIPT II™ System (Life Technologies). Optimal RT-PCR conditions were adjusted using the FailSafe PCR Enzyme Mix kit (Epicentre). The reaction was conducted in 18-25 amplification cycles, which were expected to be in the linear range of the assay. Primers were: CpG5B6: 5'-TCT GCT TGC TTG GCC CTT CTG (SEQ ID NO:64) (sense strand) and 5'-TCC CTT CTG CCA CAT GGT TCA (SEQ ID NO:65) (antisense strand); SC21G11: 5'-GCA CCG GTA AG G AA AAC AAA A (SEQ ID NO:66) (sense strand) and 5'-GAG CCA GTT GAT CAC CTC CTG (SEQ ID NO:67) (antisense strand); SC77F6: 5'-CAG AAC CAC CGC TAC AAA ATG (SEQ ID NO:68) (sense strand) and 5'-GAC ATG GTG CCG TAG TCC GAG (SEQ ID NO:69) (antisense strand); PY2F1: 5'-CCC CCA TCC CAG AAG ACA AAG (SEQ ID NO:70) (sense strand) and 5'-CTC GCT TTC GGA CAT GG TTC T (SEQ ID NO:71) (antisense strand); SC13D6: 5'-TTG GAG TAA GAC TCC TGC ATC GCG (SEQ ID NO:72) (sense strand) and 5'-CTC GCT TTC GGA CAT GGTTCT (SEQ ID NO:73) (antisense strand); SC70E4: 5'-ACA CCC AGC CCC CAT TAC CTA (SEQ ID NO:74) (sense strand) and 5'-TCA CCC CTT GGT TGT CGA TGG (SEQ ID NO:75) (antisense strand); SC62A4: 5'-TCC CCT CAC TCC CTT GCT GGT (SEQ ID NO:76) (sense strand) and 5'-TGG CCA TAT GGA TGC TCC TTG (SEQ ID NO:77) (antisense strand); CpG12F10: 5'-GAT GTG AGG AGT GTG GGA AGG (SEQ ID NO:78) (sense strand) and 5'-TGT GGA CTC TGC GAT GAG AAT (SEQ ID NO:79) (antisense strand); MP3D7: 5'-TGG AAC AGT TTG GAG GGC TCA (SEQ ID NO:80) (sense strand) and 5'-CAC GGC TGC ACT AGG CGA GTA (SEQ ID NO:81) (antisense strand); MP2A3: 5'-CTT GCA GTG GCT GGA GAT GAA (SEQ ID NO:82) (sense strand) and 5'-CAA GAC ACG TCA GCC TGG CAT (SEQ ID NO:83) (antisense strand); β-actin: 5'-GGA TTC CTA TGT GGG CGA CGA G (SEQ ID NO:84) (sense strand) and 5'-CGC AGC TCA TTG TAG AAG GTG TGG (SEQ ID NO:85) (antisense strand). The levels of amplified cDNAs were compared to that of the β-actin cDNA as previously described (Laux, D. E. et al., *Breast Cancer Res. Treat.*, 56:35-43, 1999).

EXAMPLE 8

ECISTs were Identified in a CpG Island Microarray Panel

This example shows the identification of 1,162 ECIST (expressed CpG island sequence tag) loci, enabled by construction of full-length cDNA molecules and the use thereof to screen microarray panels comprising 7,776 CpG tags for hybridization.

Figures 12A, 12B, 12C:
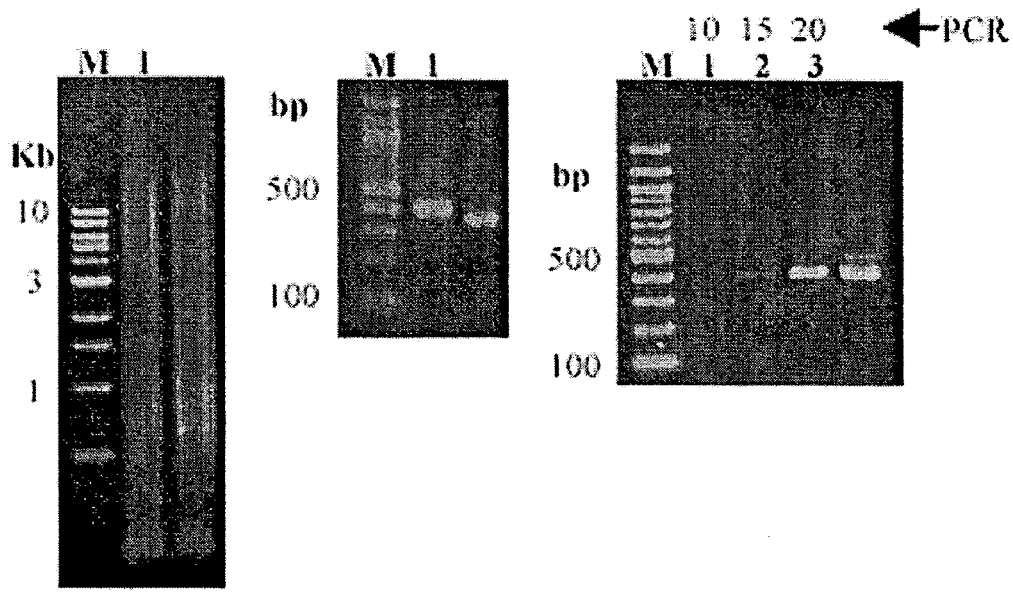
FIG. 12A illustrates an agarose gel electrophoretic analysis of full-length cDNAs generated by long RT-PCR (RNA ligase-mediated cDNA synthesis) from breast epithelial RNAs or reference RNAs. Only full-length, capped mRNAs were amplified by long RT-PCR. cDNAs (30 to 1-kb) were amplified with 5'- and 3'-end adapter primers. The gel lanes are as follows: M, 1-kb molecular markers; lane 1, untreated MDA-MB-231 cells; lane 2, 0.75 μM 5-aza-2'-deoxycytidine-treated MDA-MB-231 cells.
FIG. 12B illustrates an agarose gel electrophoretic analysis, verifying the integrity of the 5'-end of the cDNA generated as in FIG. 12A. PCR was conducted using full-length cDNA amplicons as templates. The 5'-end common adapter primer and a gene-specific primer (3'-end) were used in the amplification reaction. The gel lanes are as follows: M, 100-bp molecular markers; lane 1, the 5'-end fragment of β-actin cDNA; lane 2, the 5'-end fragment of GAPDH cDNA.
FIG. 12C illustrates an agarose gel electrophoretic analysis, showing optimization of the number of PCR cycles such that the amounts of amplification products are within the linear amplification range for optimal semi-quantitation of microarray images. PCR was conducted using the 5'-end adapter primer and a 3'-end primer specific for β-actin cDNA under different cycling conditions (lanes 1-4). The optimized number of amplification cycles used in the experiments discloses herein was 18, which also preserved the relative proportions of mRNA species in the cells.

The method of RNA ligase-mediated cDNA synthesis (Suzuki, Y. et al., *Gene*, 200:149-156, 1997) was used to generate full-length cDNAs from breast epithelial RNAs or the Stratagene Human Universal Reference RNAs. Only cDNAs of full-length, capped mRNAs were amplified by long-PCR (FIG. 12A). Accordingly, the integrity of the 5'-end of cDNAs was preserved (e.g., β-actin and GAPDH cDNAs in FIG. 12B). The cycle number of PCR was further optimized to be within the linear range of amplification for semiquantitation of microarray images (FIG. 12C).

Figures 13A, 13B, 13C:
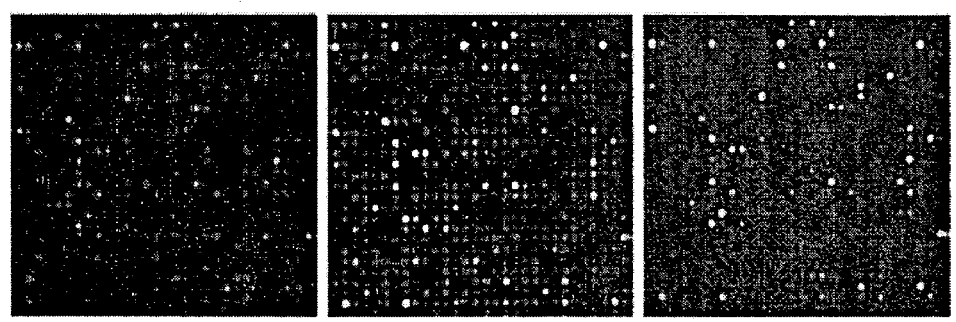
FIG. 13A shows an image of a representative CpG island tag microarray, comprising identified ECISTs. Full-length aa-dUTP-labeled cDNA amplicons were prepared from normal breast epithelial RNA or Human Universal Reference RNAs (STRATAGENE™), fluorescently-labeled with Cy3 (Cyanine 3; green), and hybridized to a microarray panel containing 7,776 CpG island tags. Positive ECISTs showed hybridization intensities 2-times greater than that of background. Only a section of the complete microarray image is shown. Of the 7,776 CpG tags screened, 1,162 tags were positive for ECISTs, defined by hybridization intensities 2-times greater that that of background.
FIG. 13B shows use of the ECIST microarray panel of FIG. 13A for Differential Methylation Hybridization ("DMH") analysis to identify 219 specific hypermethylated ECIST loci. Test (MDA-MB-231 cells) and control DNA amplicons were prepared and labeled with Cy5 and Cy3, respectively. Amplicons representing differential pools of methylated DNA in breast cancer cells relative to a normal control cells were used as targets for microarray hybridization (as described herein below). The same section of the microarray shown in FIG. 13A is shown here. Hypermethylated ECIST loci appear as "red" spots, whereas "yellow" spots represent no methylation changes between the test and control samples. A total of 219 hypermethylated ECIST loci were identified using a 'cut-off' of >1.5 for the normalized Cy5/Cy3 signal ratio. Yellow spots correspond to no methylation differences between test and reference genomes. ECISTs that are devoid of hybridization represent unmethylated loci.
FIG. 13C shows use of the ECIST microarray panel of FIGS. 13A and 13B for demethylation expression analysis to identify methylation-controlled genes. Full-length cDNA amplicons from 0.75 µM 5-aza-2'-deoxycytidine-treated and untreated MDA-MB-231 cells were labeled with Cy5 and Cy3, respectively. Microarray hybridization was conducted as described herein below. The same section of the microarray used in FIGS. 13A and 13B is shown here. ECIST tags appearing as red spots correspond to genes that are up-regulated by the demethylation treatment.

The amplified products were labeled with Cy3 (Cyanine 3) fluorescence dye and hybridized to the microarray panel. Excluding repetitive elements (e.g., Alu and mitochondrial and ribosomal RNA genes), a total of 1,162 loci met the criteria of ECIST from an initial screening of 7,776 CpG island tags. These positive loci were defined by hybridization intensities 2 times greater than that of the background (FIG. 13A, showing a portion of the microarray).

A total of 155 of the 1,162 ECISTs were further characterized by nucleotide sequencing. One hundred thirty-two (132) (85.2%) such loci contain sequences matched to known transcripts or expressed sequences tags. Sequences of twenty-three (23) other loci (14.8%) matched to genomic regions likely comprising as yet uncharacterized expressed sequences. The redundancy with multi-copy genes is ~10% in the ECIST panel, based on the sequence information. For example, small nuclear RNA genes (U1, U2, and U3) and histone genes (H2A and $H_2B$), presented 2-4 times in the ECIST clones sequenced.

Figures 14A, 14B:
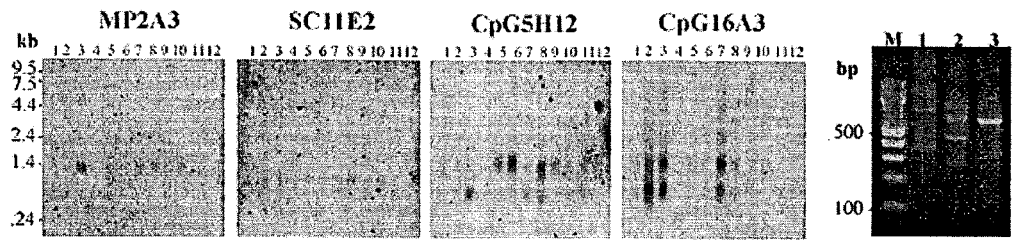
FIG. 14A shows RNA analysis by Northern blot hybridization of ECIST loci whose sequences did not match to known genes. As shown in the multiple tissue blots, MP2A3 and SC11E2 probes identified single transcripts while loci CpG5H12 and CpG16A3 contained transcripts with multiple splice variants. $^{32}$P-labeled probes derived from putative expressed sequences of ECISTs (listed on the top of the panels) were hybridized with the Clontech Multiple Tissue Northern blots. Lane 1, brain; lane 2, heart; lane 3, skeletal muscle; lane 4, colon; lane 5, thymus; lane 6, spleen; lane 7, kidney; lane 8, liver, lane 9, small intestine; lane 10, placenta; lane 11, lung; lane 12, peripheral blood leukocyte
FIG. 14B shows RNA analysis, by 5'-rapid amplification of cDNA ends (RACE), of additional ECIST loci whose sequences did not match to known genes. PCR was conducted using full-length cDNA amplicons as templates. The 5'-end common adapter primer and a gene-specific primer (3'-end) were used in the amplification reaction. M, 100-bp molecular markers; lane 1, the 5'-end fragments of CpG6B6 cDNA; lane 2, the 5'-end fragments of PY2F1 cDNA; lane 3, the 5'-end fragment of SC13D6 cDNA. The CpG6B6, PY2F1, and SC13D6 loci appear to encode rare transcripts based on the relatively sensitive 5'-race assays.

Northern blotting analysis was conducted to verify the presence of novel mRNAs in nine ECIST loci whose sequences did not match to known genes (FIG. 14A). As shown in multiple tissue blots, MP2A3 and SC11E2 probes identified single transcripts while loci CpG5H12 and CpG16A3 contained transcripts with multiple splice variants. No detectable transcripts were observed in the five other ECISTs by northern hybridization. However, three of these loci (CpG6B6, PY2F1, and SC13D6) likely encode rare transcripts based on more sensitive 5'-RACE assays (FIG. 14B).

EXAMPLE 9

Hypermethylated ECIST Loci were Identified

The panel of affixed 1,162 ECISTs of above Example 8 was used in microarray hybridization screens, using the differential methylation hybridization (DMH) method, to identify novel genes that were silenced via CpG island hypermethylation. Specifically, amplicons, representing differential pools of methylated DNA in MDA-MB-231 breast cancer cells relative to normal control cells, were used as targets for microarray hybridization using the DMH screening assay and the affixed 1,162 ECIST loci of Example 8 above.

Linker-ligated genomic DNA samples were digested with methylation-sensitive endonucleases prior to PCR. Genomic DNA fragments derived from MDA-MB-231 cells and that contained hypermethylated sites were protected thereby from the endonuclease digestion and could be subsequently amplified by linker-PCR. By contrast, corresponding normal cell-derived fragments containing the corresponding unmethylated endonuclease sites were cut and thereby rendered non-amplifyable.

Figure 16:
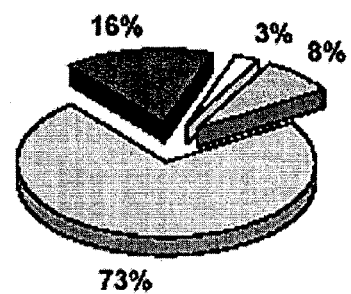
FIG. 16 illustrates the relation between DNA methylation and gene expression. The pie chart shows the percentages of ECISTs whose genes are hypermethylated in MDA-MB-231 cells and/or are up-regulated by a demethylation treatment. For example, according to the present invention, the combined expression and methylation data identify 30 ECIST loci having expression that is down-regulated by DNA hypermethylation, but that is reactivated by demethylation treatment (deoxyC).

The amplicons, representing differential pools of methylated DNA in breast cancer cells relative to a normal control, were used as targets for microarray hybridization. Hypermethylated ECIST loci appeared as "red" spots after microarray hybridization, because greater signal intensities were obtained from the Cy5 (red) test amplicons, but not from those of the Cy3 (green) control amplicons (FIG. 13B). The hybridization experiments were repeated and only those reproducible spots were chosen for analysis. A total of 219 loci were identified, based on setting a positive loci 'cut-off' value of >1.5 for the normalized Cy5/Cy3 ratio (FIG. 16). This cut-off ratio value was previously established by applicants to be effective in identifying differentially hypermethylated CpG islands in breast tumors (Yan, P. S., et al., *Cancer Res.*, 61:8375-8380, 2001).

ECISTs corresponding to loci having no methylation differences between the MDA-MB-231 and normal genomes appeared as "yellow" spots (Cy5/Cy3=1) on the amplicon-hybridized ECIST array. ECISTs whose signal intensities were devoid of hybridization signals represent the unmethylated loci in MDA-MB-231 cells; isolated genomic fragments corresponding to such loci were restricted away by the methylation-sensitive endonuclease treatment prior to linker-PCR.

Occasionally, "green" spots (Cy5/Cy3<0.5), indicating hypomethylation, were seen in MDA-MB-231 cells.

EXAMPLE 10

Methylation-Silenced, Demethylation-Responsive ECIST Loci were Identified

This example shows that particular ECIST loci identified as being hypermethylated in DMH amplicon/microarray screening assays of Example 9 above, comprise loci corresponding to methylation silenced genes, and that in particular instances such silencing was reactivated by treatment of cells with a demethylation agent(s).

Figures 15A, 15B:
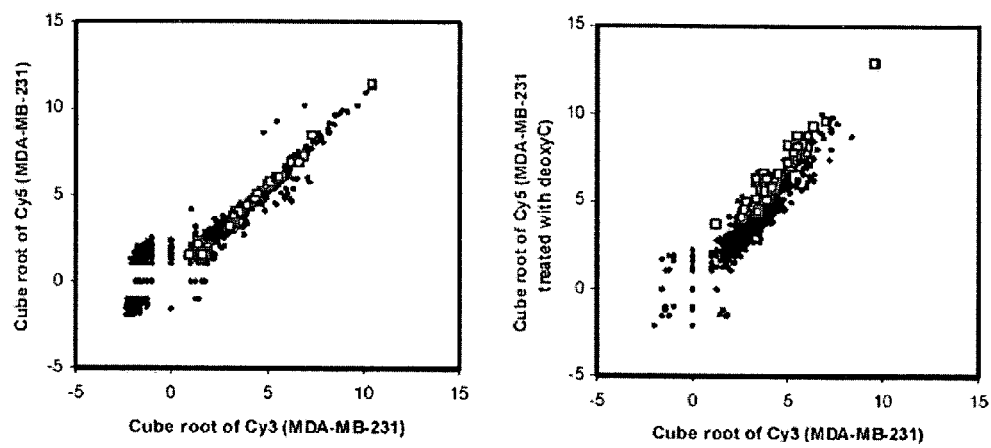
FIG. 15A shows a scatter plot of expression data using the ECIST microarray panel of FIG. 2 to show self- (i.e., untreated vs. untreated) hybridization as an internal control. Two equal portions of cDNA prepared from MDA-MB-231 cells were labeled with Cy3 and Cy5, respectively and hybridized to the ECIST microarrays as in FIG. 2C.
FIG. 15B shows a scatter plot of expression data using the ECIST microarray panel of FIG. 2 to show comparative- (i.e., untreated vs treated) hybridization to identify genes that are up-regulated by the demethylation treatment, based on a Cy5/Cy3 'cut-off' ratio of >2 to define up-regulation. Briefly, 5-aza-2'-deoxycytidine (DeoxyC)-treated and untreated MDA-MB-231 cells were labeled with Cy5 and Cy3, respectively, and hybridized to the ECIST microarrays. Red squares depict the locations of the 30 methylation-silenced genes selected for further study (see FIG. 5 herein). The normalized Cy5/Cy3 ratio for each ECIST locus is presented and the scales of the X and Y axes are logarithmic.

Full-length cDNA amplicon targets were separately prepared from MDA-MB-231 cells treated with or without a demethylating agent, deoxyC. Fluorescently-labeled targets were co-hybridized to the ECIST panel (FIG. 13C) and the data outputs from the duplicated and self-hybridization experiments were analyzed using significant analysis of microarray (SAM) software (FIG. 15). SAM identified ECIST loci with statistically significant changes in expression by assimilating a set of gene-specific t tests. Each ECIST was assigned a score on the basis of its change in gene expression relative to the standard deviation of repeated measurements for that locus. ECISTs with scores greater than a threshold were deemed potentially significant. By contrast, loci identified by a chance event were treated as false-positives. The false-positive rate was calculated by analyzing the permutations of measurements of gene expression derived from microarray experiments (Tusher, V. G., et al., *Proc. Natl. Acad. Sci. USA*, 98:5116-5121, 2001). By choosing a threshold that gave a false-positive rate of 1%, 126 up-regulated loci were determined to be statistically significant among the 1,162 ECISTs analyzed. No down-regulated loci were identified by SAM analysis.

Combining and correlating both the methylation and expression microarray data, we identified 30 ECIST loci whose corresponding transcripts are down-regulated via DNA hypermethylation and can be reactivated by 0.75 μM deoxyC (FIG. 16). Furthermore, 17 out of 19 such ECISTs whose sequences matched to known genes in GenBank were confirmed as being localized to the first exon of their corresponding genes (Table II).

Additionally, 189 ECIST loci were identified that were hypermethylated in MDA-MB-231 cells, but their corresponding transcripts could not be reactivated (or up-regulated) by the treatment of deoxyC. Interestingly, a group of 96 loci was identified, whose transcripts were found to be up-regulated in response to demethylation, but appeared not to be associated with CpG island hypermethylation. No detectable changes of DNA methylation or gene expression were present in the remaining loci by these microarray methods.

TABLE II

EXPRESSED CPG ISLAND SEQUENCE TAGS
A list of 30 methylation-silenced genes in breast cancer cell line MDA-MB-231.

| Clone I.D. | Gene | Accession Number | Promoter (1st exon) CpG island | [4]Cy5/Cy3 Expression | Methylation | Sequence Description |
|---|---|---|---|---|---|---|
| CpG5B6* | CYP27B1 | AF027152; (NM_000785 is cDNA) | [2]+ | 2.7 | 2.0 | 25-hydroxyvitamin D-I-α-hydroxylase (SEQ ID NO:86) |
| CpG6B6 | dJ631M13.5 | AL117333 | + | 2.6 | 1.6 | A novel protein (SEQ ID NO:87) |
| CpG15E2 | [1]ND | NT_010351 | ND | 3.3 | 4.3 | Close to MAP2K5 gene upstream |
| CpG21G11 | ND | AC002424 | ND | 2.9 | 1.6 | Cosmid at chromosome 7q31.3 (SEQ ID NO:88) |
| CpG32H12 | ND | Z60712 | ND | 2.6 | 3.6 | CpG island DNA genomic MseI fragment (SEQ ID NO:89) |
| CpG65A1 | TNS | AF225896 | + | 4.3 | 2.3 | Tensin (SEQ ID NO:90) |
| CpG65C10 | TBX4 | AC005901 | [3]+ | 4.7 | 2.9 | T-box transcription factor (SEQ ID NO:91) |
| DL2F9 | ERCC-1 | X06581 | + | 3.8 | 1.8 | DNA excision repair protein (SEQ ID NO:92) |
| MP1F6 | LOC84661 | XM_029512 | + | 2.1 | 1.8 | Dpy-30 like protein |
| MP2F1 | H4FJ | Z80787 | + | 3.2 | 11.4 | Histone H4 family member J (SEQ ID NO:93) |
| MP2F10 | ND | Z82254 | ND | 3.2 | 1.8 | Cosmids on the X chromosome (SEQ ID NO:94) |
| PY1H8 | PSMB4 | XM_047881 | + | 2.1 | 2.0 | Proteasome subunit β type 4 |
| PY2F1 | FLJ10466 | AK001328 | + | 3.2 | 1.9 | Full-length cDNA FLJ10466 (SEQ ID NO:95) |
| PY3D3 | EST | AI023535 | ND | 2.4 | 1.9 | cDNA5'-end(SEQ ID NO:96) |
| PY3D6 | EST | BI518683 | ND | 2.0 | 2.9 | eDNA 5'-end (SEQ ID NO:97) |
| PY3F2 | HSRN04 | V00587.1 | + | 2.0 | 1.9 | Human gene possibly encoding U1 RNA (SEQ ID NO:98) |
| SC2C3 | EST | BE502068 | ND | 4.9 | 3.2 | IMAGE: 3197059 (SEQ ID NO:90) |
| SC8F2* | RPS16 | XM_046112 | + | 2.0 | 1.6 | Ribosomal protein S16 |
| SC12A2 | SAAS | NM_013271 | + | 2.2 | 2.0 | Granin-like neuroendocrine peptide precursor (SEQ ID NO:100) |
| SC13D6* | EST183864 | AA313068 | ND | 2.1 | 5.9 | Pancreas tumor, subtracted cDNA 5'-end (SEQ ID NO:101) |
| SC15E7 | ND | AL359219 | ND | 4.0 | 1.9 | BAC clone C-2315A10 (SEQ ID NO:102) |
| SC15H6* | H2BFR | XM_011505 | + | 2.6 | 3.4 | Histone 2B family member R |
| SC19F1* | EST | BE838797 | ND | 2.7 | 2.6 | cDNA 5'-end(SEQ ID NO:103) |

TABLE II-continued

EXPRESSED CPG ISLAND SEQUENCE TAGS
A list of 30 methylation-silenced genes in breast cancer cell line MDA-MB-231.

| Clone I.D. | Gene | Accession Number | Promoter (1st exon) CpG island | [4]Cy5/Cy3 Expression | Methylation | Sequence Description |
|---|---|---|---|---|---|---|
| SC20G3 | HOXD3 | Y09980 | + | 2.3 | 1.9 | Homeobox D3, DNA binding protein (SEQ ID NO:104) |
| SC21A8 | U3B2 | AF020535 | + | 3.2 | 1.7 | U3 small nuclear RNA promoter region (SEQ ID NO:105) |
| SC21G11 | HSPA2 | L26336 | − | 5.4 | 8.5 | Heat shock protein 70.2 (SEQ ID NO:106) |
| SC40C8 | H2BFG | NM_00352 | + | 2.7 | 3.8 | Histone 2B family member G (SEQ ID NO:107) |
| SC77F6* | TTF-1 | AF027332 | + | 3.8 | 2.8 | Thyroid-specific transcription factor 1 (SEQ ID NO:108) |
| SC87E7 | EST | AA365852 | ND | 2.4 | 4.5 | Pineal gland II cDNA 5'-end (SEQ ID NO:109) |
| SC89F2 | HAGE | NM_018665 | + | 14.6 | 1.8 | DEAD-box protein (SEQ ID NO: 110) |

[1]ND: not determined or not known.
[2]+: positively match the first exon.
[3]−: negatively match the first exon.
[4]Cy5/Cy3: the average normalized ratio of each ECIST obtained from microarray analysis (see further description in the text).
*Hypermethylation also detected in primary breast tumors.

EXAMPLE 11

ECISTs Responsive to Demethylation were Independently Verified

Figure 17A:
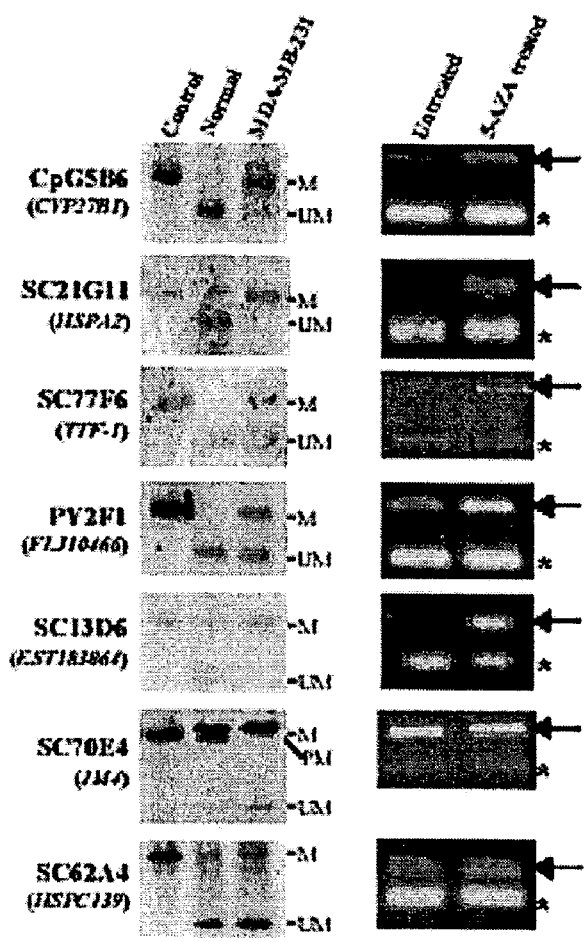
FIG. 17A illustrates a verification of methylation-silenced genes by Southern blotting and RT-PCR analyses. Genomic DNA (10 µg) from breast cancer cell line MDA-MB-231 and a normal breast sample was digested with MseI and one of these methylation-sensitive endonucleases (BstUI, HpaII, or HhaI) as described herein below, and was subject to Southern analysis. Control DNA was digested with MseI only. The nylon membranes were hybridized separately with $^{32}$P-labeled fragments of the ECIST loci shown at left (CYP27B1, HSPA2, TTF-1, FLJ1046, EST183864, JM4 and HSPC139) [Note: gene names or expressed sequence tag numbers appearing in GenBank are shown in parentheses]. M: methylated DNA fragment; PM: partially methylated DNA fragments; UM: unmethylated DNA fragments. Total RNAs from 0.75 µM 5-aza-2'-deoxycytidine-treated and untreated MDA-MB-231 cells were isolated for RT-PCR. Arrows indicate the position of amplified cDNA fragments. The levels of amplified cDNAs were compared to that of the β-actin cDNA.

Among the 30 methylation-silenced loci, we independently confirmed the microarray findings of 3 known genes: CYP27B1 (SEQ ID NO:86); HSPA2 (SEQ ID NO:106); and TTF-1 (SEQ ID NO:108), and 2 novel expressed sequences: FLJ10466 (SEQ ID NO:95); and EST183864 (SEQ ID NO:101), by Southern and RT-PCR analyses. As shown in FIG. 17A, their CpG island fragments appeared to resist the methylation-sensitive restriction in MDA-MB-231 cells (left panels of FIG. 17A). Hypermethylation of the CpG islands was associated with transcriptional silencing of these genes, but their expression could be reactivated by treating MDA-MB-231 cells with deoxyC as shown by RT-PCR analysis (right panels of FIG. 17A). Two additional loci, SC70E4 (JM4) and SC62A4 (HSPC139), could not be confirmed by these assays, potentially representing a false-positive finding by the microarray analyses.

Figure 17B:
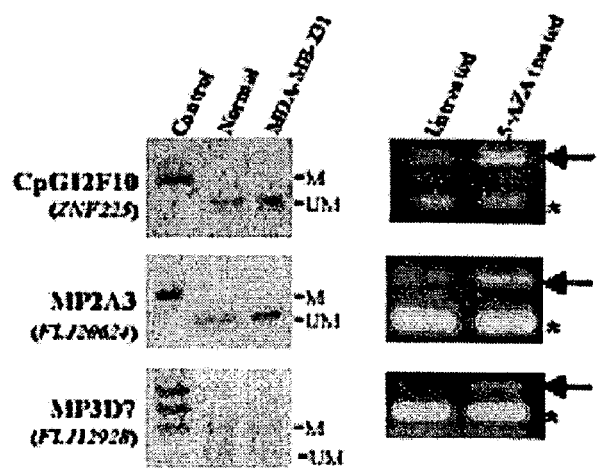
FIG. 17B illustrates a verification of ECIST loci that are indirectly upregulated by demethylation. As indicated, the Southern and RT-PCR assays are described in FIG. 5A. [Note: multiple DNA fragments (the upper 2 bands) were seen in the control, MseI-digested lane of MP3D7, because of non-specific hybridization of the probe.

Southern and RT-PCR analyses were also used to confirm the microarray findings of 3 ECIST loci (CpG12F10, MP2A3, and MP3D7) whose corresponding transcripts were indirectly up-regulated by the demethylation treatment (FIG. 17B). That is, no evidence of CpG hypermethylation in MDA-MB-231 cells was observed in these loci by Southern hybridization, but their expression levels assessed by RT-PCR appeared to be increased in the deoxyC-treated relative to the untreated cells.

EXAMPLE 12

The CYP27B1 Promoter CpG Island was Hypermethylated in Primary Breast Tumors Among the 219 hypermethylated ECISTs identified in MDA-MB-231, only 37 loci (16.9%) corresponded to those that were previously found to be hypermethylated in primary breast tumors (see examples in Table II) (Yan, P. S. et al., Cancer Res., 61:8375-8380, 2001). This finding is consistent with the notion that hypermethylation of some loci can be attributed to an intrinsic property of cultured cells and does not necessarily originate from a malignant process in vivo (Smiraglia, D. J. et al., Hum. Mol. Genet., 13:1413-1419, 2002). Because CYP27B1 has recently been implicated in growth suppression of prostate cancer (Hsu, J. Y. et al., Cancer Res., 61:2852-2856, 2001), the in vitro hypermethylation finding of this gene was extended by an in vivo Southern analysis of 17 primary breast tumors.

Figure 18:
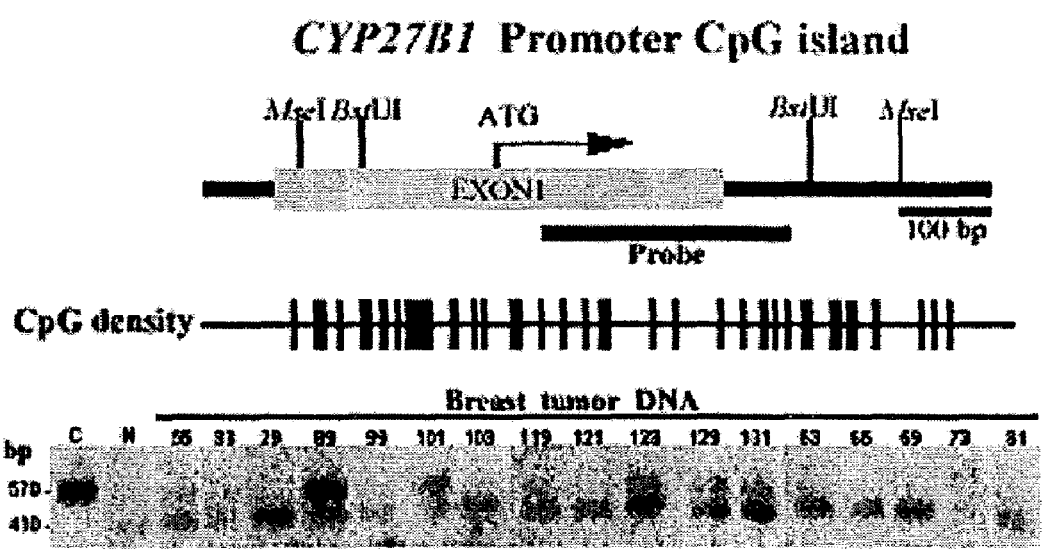
FIG. 18 illustrates a methylation analysis of the CYP27B1 promoter by Southern analysis. The position of MseI and methylation-sensitive BstUI sites, the probe, and the CpG density in the CYP27B1 promoter are indicated. Genomic DNA (10 µg) from breast tumors and a normal control was digested with MseI and BstUI, blotted to nylon membranes, and subject to Southern analysis. C: control DNA digested with MseI only; N: normal DNA digested with MseI and BstUI.

The analysis showed that hypermethylation of the CYP27B1 promoter (SEQ ID NO:86) was detected in 41% of the breast tumors analyzed (FIG. 18). Extrapolating from the in vitro (cell line) finding, we reason that this epigenetic event may lead to the transcriptional inactivation of the CYP27B1 gene in vivo. The CYP27B gene encodes an important enzyme, 1α hydroxylase, for vitamin D metabolism (Takeyama, K. et al., Science (Wash. DC), 277:1827-1830, 1997), and disruption of its enzymatic activity would likely decrease the normal anti-proliferative effects of vitamin D in breast cancer.

Summary of Examples 7-12

Described herein are novel high-throughput array-based techniques that allow for simultaneous analysis of expression and methylation alterations at the genome level. This new generation of microarray is useful to dissect the complex relationship between DNA methylation and gene expression in cancer. The ECIST microarray is also useful to discover methylation-controlled genes during normal development, as well as novel imprinted genes responsible for certain genetic diseases.

Various cDNA microarrays have been applied to determine global profiles of gene expression in demethylated cells (Karpf, A. R., et al., Proc. Natl. Acad. Sci. USA, 96:14007-14012, 1999; Jackson-Grusby, L. et al., Nat. Genet., 27:31-39, 2001). Many genes participating in cell-cycle control, growth factor/receptor signaling, and mobilization of retro-elements appear to be up-regulated[1] in a demethylated state (Jackson-Grusby, L. et al., 2001, supra). Moreover, cDNA microarrays have been shown to be useful in differentiating tumor-specific expression profiles that have implications in patients' diagnosis and prognosis (Golub, T. R. et al., *Science (Wash. DC)*, 286:531-537, 1999; Alizadeh, A. A. et al., *Nature (Lond.)*, 403:503-511, 2000; Perou, C. M. et al., *Nature (Lond.)*, 406:747-752, 2000; and Bittner, M. et al., *Nature (Lond.)*, 406:536-540, 2000).

[1] Interestingly, as further confirmed by the instant examples, down-regulated genes were rarely observed in these previous studies (Karpf, A. R., et al., 1999; Jackson-Grusby, L. et al., 2001, supra).

This type of microarray analysis, however, cannot distinguish direct (primary) epigenetic gene regulation, from indirect (secondary) gene regulation as a downstream event in an epigenetic cascade. Moreover, such microarray approaches are limited in their ability to detect down-regulated genes, particularly in primary tumors contaminated with residual normal stroma. Furthermore, cDNA microarray approaches require targets derived from RNA, which is substantially more labile and difficult to obtain directly from small clinical specimens.

Therefore, the inventive use of ECIST microarrays represents a substantial improvement over cDNA microarrays for molecular profiling of primary tumors. The ECIST microarray uses easily obtainable and relatively stable targets derived from a patients' tumor DNA, for methylation analysis. Accordingly, the inventive dual ECIST DMH/expression assays provide reliable evidence for methylation-mediated gene silencing events, because the direct association of hypermethylation with gene silencing is afforded by the associated ECIST expression analysis.

Expressed CpG island sequence tags (ECISTs) are, according to the present invention, effective markers for the high-throughput identification of methylation-silenced genes in cancer cells. In addition, this novel approach is useful for examining demethylation strategies and therapeutic agents for the treatment of cancer.

Significantly, the inventive use of ECIST microarrays enable distinguishing, in a high-throughput manner, the primary and secondary causes of epigenetic (methylation/demethylation) events. According to the present invention, at least 30 genes were identified that are involved in primary responses to deoxyC treatment in MDA-MB-231 cells. The examples herein indicate that reactivation of these genes is a direct result of erasing DNA methylation in the promoter regions (including the first exons).

Additionally, according to the present invention, 96 genes were identified that were not hypermethylated, but were nonetheless determined to be up-regulated in the deoxyC-treated MDA-MB-231 cells. Without being bound by theory, it is likely that the induction of these genes is indirect (secondary), in one or more epigenetic cascades initiated by one or more loci that are directly (primarily) regulated by methylation/demethylation.

Furthermore, a significant number of genes were identified that were hypermethylated, yet displayed no detectable up-regulation in cells treated with demethylating agents. One explanation is that the low dose (0.75 µM) of deoxyC used in the experiment might be suboptimal to invoke re-expression of these hypermethylated genes in MDA-MB-231 cells. It is also possible that some of these ECIST loci are not located at the 5'-end of the regulatory region of genes (e.g., ECIST clone MP3B12, Caveolin-1 exon 2; CpG79H10, IDI2 exon 2; and PY3E1, hypothetical gene LOC159615 exon 14) and thus hypermethylation bears no consequence on the expression status of these genes.

Nevertheless, according to the present invention, ECIST microarrays are useful to study the efficacy, optimal doses, and types of demethylating agents in cancer treatment. ECIST microarrays are also useful to reveal the sequence of events following demethylation treatments, and provide tools for elucidating the mechanisms of aberrant DNA methylation in the tumor genome.

EXAMPLE 13

ECIST Microarrays were Used in Developing a Novel Genomic Microarray System for Parallel Detection of Changes in Gene Expression, DNA Methylation and Histone Acetylation It has been demonstrated that pharmacological reversal of promoter hypermethylation status results in global and specific changes in gene expression (Suzuki et al., *Nature Genet.* 31:141-149, 200; Jones & Baylin, *Nature Rev. Genet.* 3:415-428, 2002); in addition, inhibiting DNA methylation has both primary (direct) and secondary (indirect) effects on gene expression (Suzuki et al., *Nature Genet.* 31:141-149, 2002; Liang et al., *Cancer Res.*, 62:961-966, 2002; and Karpf et al., *Proc. Natl. Acad. Sci. USA*, 96:14007-14012, 1999).

Currently, however there is no efficient method useful to elucidate the functional relationship between DNA methylation and histone acetylation in gene silencing. ECIST microarrays, such as those described herein above, were thus further used as described below in a novel genomic microarray system for efficiently detecting changes in gene expression, DNA methylation and histone acetylation.

Specifically, an integrated "triple" microarray system was developed to decipher the hierarchies of epigenetic regulation of gene expression in cancer cells. In a preferred embodiment, the microarray panel contained 1,507 ECISTs, short genomic fragments (0.2 to 2-kb) located at the 5'-end regulatory regions of genes (Shi et al., *Cancer Res.* 62:3214-3220, 2002, incorporated by reference herein in its entirety). The GC-rich components of ECISTs were used for screening methylated CpG sites, the exon-containing portions (i.e., the first exons) for measuring levels of the corresponding transcripts, and the promoter sequences within ECISTs for identifying chromatins immunoprecipitated with antibodies against acetylated histones.

The present novel microarray system provides an effective means of segregating, at specific loci, expression changes that occur as a consequence of reversing promoter hypermethylation status by epigenetic treatments.

Materials and Methods

Cell Culture. A human epithelial ovarian cancer cell line CP70 (gift from Dr. Robert Brown, Glasgow, United Kingdom) was cultured in the presence of vehicle (PBS) or DAC (5-aza-2'-deoxycytidine) (0.5 µM; medium changed every 24 h). After 4 days, cells were either harvested, or treated with TSA (trichostatin A) (0.5 µM) for 12 h and then harvested. Some cells were also treated with TSA alone for 12 h before harvest. DNA and RNA were isolated using the QIAamp™ Tissue and RNeasy™ kits (Qiagen), respectively.

Microarray Screening of ECISTs. To identify ECISTs (including the first exons), RLCS (RNA ligase-mediated cDNA synthesis) (Suzuki et al., *Gene* 200:149-156, 1997) was used to prepare targets for screening of CpG island clones derived from a genomic library, CGI (Cross et al., *Nature Genet.* 6:236-244, 1994). Briefly, in the presence of T4 RNA ligase, an RNA adapter (0.5 nmol, 5'-ACC GGA GCG GCA CGG GAA AUA GAG CAA CAG GAA A; SEQ ID NO:111) was ligated to the 5'-ends of decapped mRNAs derived from the Stratagene Human Universal Reference RNAs. After reverse transcription, full-length cDNAs were amplified by long RT-PCR (TaqPlus Long PCR system, Stratagene) with the flanking 5'- and 3'-adapters (5'-GCA CGG GAA ATA GAG CAA CAG (SEQ ID NO:112) and 5'-GGC CGA CTC ACT GCG CGT CTT CTG (SEQ ID NO:113), respectively). A low number of PCR cycles (18-25) was used to preserve the linearity of amplification. Amplified products were labeled with Cy3 fluorescent dyes as previously described (Shi et al., Cancer Res. 62:3214-3220, 2002) and hybridized to the CGI microarray panel. Hybridization and post-hybridization procedures were performed according to DeRisi et al. (http://www.microarrays.org). Hybridized slides were scanned with the GenePix™ 4000A (Axon). The acquired images and data were transferred to Excel spreadsheets for further analysis using GenePix™ Pro 3.0. CGI loci with signal intensities 2-fold greater than local background were scored as positive for containing expressed sequences.

Methylation Microarray Analysis. Preparation of methylation amplicons was carried out essentially as described (Yan et al., Cancer Res. 61:8375-8380, 2001). Briefly, CP70 DNA (~1 μg) was digested with MseI and then ligated to a PCR-linker. The ligated DNA was digested with methylation-sensitive endonucleases BstUI and HpaII, and amplified with a linker primer by PCR. DNA obtained from a normal ovary tissue was prepared similarly. Genomic fragments containing methylated sites were protected from enzymatic restrictions and could be amplified; however, fragments containing unmethylated sites were digested and thus not present in the amplified samples. CP70 amplicons were labeled with Cy5 (red) while the control amplicons were labeled with Cy3 (green). Both samples were co-hybridized onto an ECIST microarray slide and processed as described (Id).

Expression Microarray Analysis. Total RNA (100 μg) was prepared from control (vehicle treated) CP70 cells or cells cultured with TSA and/or DAC. The RLCS method was used to generate full-length cDNAs. For quality control, the RACE (Rapid Amplification of cDNA Ends) method was used to determine the integrity of 5'-ends of a few cDNA sequences (see Shi et al., Cancer Res. 62:3214-3220, 2002). Cy5-labeled cDNAs from treated cells and Cy-3 labeled cDNAs from untreated cells were co-hybridized to the ECIST panel and microarray images obtained were processed accordingly.

CHIP Microarray Analysis. The protocol used to identify immunoprecipitated E2 F1 targets (Weinmann et al., Genes Dev. 16:235-244, 2002) was adapted for this study. To obtain a network of DNA-protein biopolymers, treated or untreated CP70 cells ($2 \times 10^7$ cells per assay) were cross-linked using 1% formaldehyde. Cell nuclei were collected by microcentrifugation and cross-linked chromatin fibers were isolated and fragmented to ~600-bp by sonication. Immunoprecipitation was carried out with 5 μg of anti-acetylated histone H3 or H4 rabbit polyclonal antibody (Upstate) or no-antibody (negative control). DNA was further released by digesting the immunocomplex with proteinase K. Purified chromatin DNA (a total of ~1 μg) was recovered from 10-15 preparations for fluorescent labeling. Microarray hybridization, post-hybridization washing, and slide scanning have been previously described (Id).

Microarray Data Analysis. The Cy3 and Cy5 fluorescence intensities of hybridized ECIST spots were obtained for each experiment. Because Cy5 and Cy3 labeling efficiencies varied among samples, the Cy5/Cy3 ratio of each spot was normalized according to the global ratio in each microarray image. As previously described (Yan et al., Cancer Res. 61:8375-8380, 2001; Wei et al., Clin. Cancer Res. 8:2246-2252, 2002; Shi et al., Cancer Res. 62:3214-3220, 2002), the derived normalization factor was further verified based on 14 internal controls whose adjusted ratios were expected to be 1. Microarray experiments were repeated twice. A self-hybridization study using two equal portions of a test DNA sample was conducted for quality control. These self-hybridizing spots typically had adjusted Cy5:Cy3 ratios approaching 1.

Nucleotide Sequencing. Plasmid DNA was prepared from ECISTs and sequenced using the DyeDeoxy Terminator reaction (Applied Biosystems) and the ABI PRISM™ 377 sequencer. The sequencing results were compared to GenBank for known sequence identities.

COBRA (combined bisulfite restriction analysis). Sodium bisulfite modification of genomic DNA, which converts unmethylated but not methylated cytosine to uracil, was performed using the CpG Genome modification kit (Intergen). COBRA was performed as described (Xiong & Laird, Nucleic Acids Res. 25:2532-2534, 1997). Briefly, ~200 ng of treated DNA was used as the template for PCR with specific bisulfite primers (Table III, below) for a given locus. $^{32}$P-labeled PCR products were digested with BstUI, separated on 8% polyacrylamide gels, and subjected to autoradiography using a PhosphorImager (Amersham-Pharmacia).

Semi-Quantitative RT- and ChIP (chromatin immunoprecipitation)-PCR. cDNA and chromatin DNA were prepared as described herein above. Diplex PCR (for both test and control targets) was performed using the AmpliTaq™ Gold polymerase (Perkin-Elmer). For RT-PCR, primer pairs were used to amplify a region (average 200-bp) from the 3'-end of a test gene, while for CHIP-PCR, primers were designed to amplify a fragment in the promoter or first-exon region (average 200-bp) of the test gene (see Table III for primer information). Following 20-25 cycles of amplification, radiolabeled PCR products were run on 5-8% polyacrylamide gels. A PhosphorImager was used to analyze the dried gels, and densitometric analysis of the observed bands was performed using ImageQuant™ (Molecular Dynamics). The relative levels of gene expression or histone acetylation were normalized with the level of the control run in the same lane.

Results

ECIST Microarray. A library of ~9,000 CGIs (Cross et al., Nature Genet. 6:236-244, 1994) was screened using RLCS (RNA ligase-mediated cDNA synthesis), resulting in recovery of 1,507 ECIST-positive loci. Nucleotide sequencing was performed on 250 of these loci to confirm whether these ECISTs were located at the 5'-ends of genes. Sequencing data showed: (i) that 79% (198/250) contained sequences located in the promoter and first exon of known genes; (ii) that 16% (40/250) matched genomic sequences and may contain as yet uncharacterized expressed sequences; and (iii) that 5% (12/250) contained non-exon 1 expressed sequences. These results support the use of ECIST loci, such as those identified herein, for assessing epigenetic alterations in cancer cells.

Figure 19:
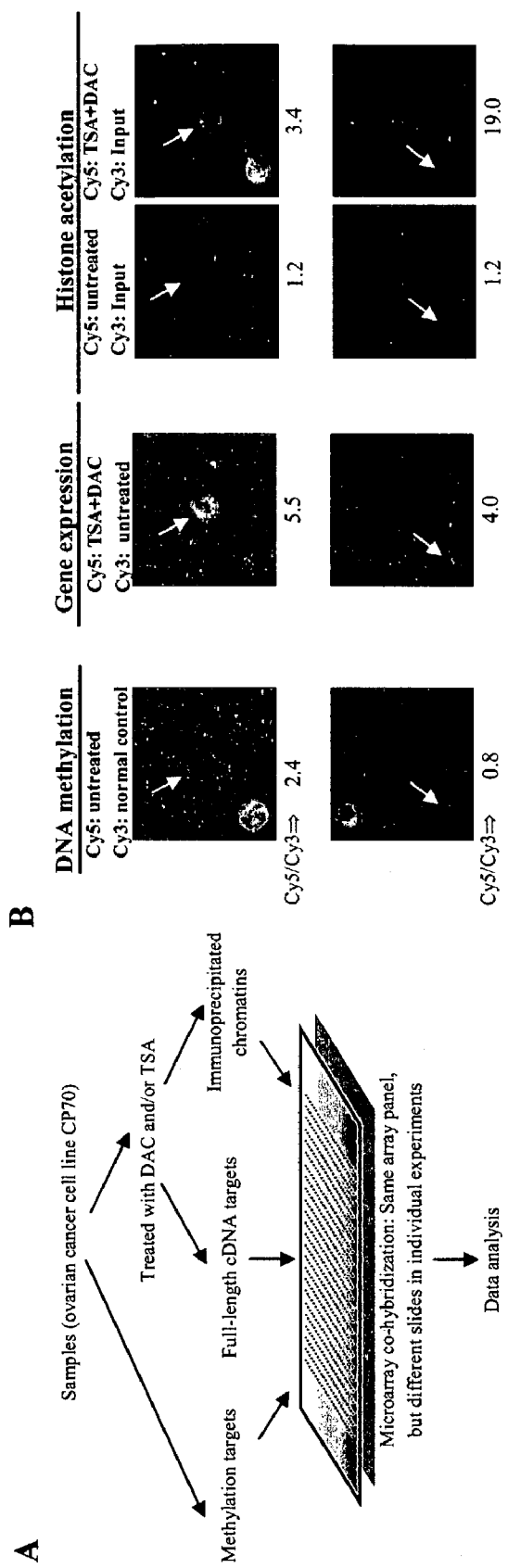
FIG. 19A shows a schematic flowchart for the inventive 'triple' analysis methodology; that is, parallel assessment of gene expression, DNA methylation, and histone acetylation in ovarian cancer cell line CP70.
FIG. 19B shows representative microarray images for the triple analysis. Cy5- and Cy-3 labeled targets were prepared as described herein below, under EXAMPLE 13, and co-hybridized to the ECIST microarray panel. The hybridization images were acquired and signal intensities of ECIST spots (see examples marked by arrows) were calculated. The normalized Cy5:Cy3 ratios are shown at the bottom of each microarray panel image. DAC refers tp 5-aza-2'-deoxycytidine, whereas TSA refers to trichostatin A.

Triple Microarray Screening. To assess gene expression, DNA methylation, and histone acetylation in parallel, CP70 cells were treated with a demethylating agent, DAC (5-aza-2'-deoxycytidine), and/or an inhibitor of histone deacetylases, TSA (trichostatin A), and then subjected to the inventive triple microarray procedures (FIG. 19A). Representative individual gene loci within the microarray are marked by arrows in FIG. 19B. At a hypermethylated locus in untreated CP70 cells (FIG. 19B, upper panels), DAC plus TSA treatments increased expression (normalized Cy5:Cy3=5.5) and histone hyperacetylation (3.4-fold relative to the control) of this gene. The combined treatment of DAC plus TSA also increased expression and

TABLE III

Primer sequences used for triple analysis

| Clone ID | Gene | Strand | COBRA primers (5' →) | ChIP-PCR primers (5' →) | RT PCR primers (5' →) | SEQ ID NOs (Left to right) |
|---|---|---|---|---|---|---|
| SC21G11 | HSPA.2 | Forward | TGTTGATGATGGGGTTGTAAATT | TTCGATGGTGGGTCCCCGGAG | GCACCGGTAAGGAAAACAAAA | 114, 116, 118 |
|  |  | Reverse | AGAAAATCACCATCACCAATAAC | GGGCAAGATTAGCGAGCAGGA | GAGCCAGTTGATCACCTCCTG | 115, 117, 119 |
| CpG5B6 | CYP27B1 | Forward | AGGGGTTGAGATATGATGTTTAGG | TCTGGCCGAACTTTTCTGCAA | TCTGCTTGCTTGGCCCTTCTG | 120, 122, 124 |
|  |  | Reverse | ACCATTTCCCCAACACTCTATC | CCTCAACTCGCCTTTTCCTTA | TCCCTTCTGCCACATGGTTCA | 121, 123, 125 |
| SC87F10 | EIF1A | Forward | TTTATTTTTATTTTGGGTATGG | GCCGTCCATTTCCAACATTTTG | ATGCTAAAATCAATGAAACTG | 126, 128, 130 |
|  |  | Reverse | CCATAAAACCACCCACCACA | TGTCGCCCCTCAGAGCAGCAG | TCTTCTACCCATAAGCTCCAT | 127, 129, 131 |
| SC10H6 | KIAA0560 | Forward | GTATAGAGGAGGTTAAAGTTTTTGG | TGGGCTGTTGTACGGGTTCC | CCTGCATGAACTTCCGGCTAC | 132, 134, 136 |
|  |  | Reverse | CCATAACAACACTCTTCCCTCC | GGTCACGAACTCCGCATTGAT | GGTCACGAACTCCGCATTGAT | 133, 135, 137 |
| DL3D6 | FLJ31663 | Forward | TTTTATTAATGGTGGTGAGAAG | TCTTCCTCCATTGCGTGTC | CCTGGCAGCCTAACCTC | 138, 140, 142 |
|  |  | Reverse | CCAACTTCCTCTTCCTCTTCTC | CCTTTACACTTCCGGTTCACT | CACCTTCTAGTGTCCGGTTGA | 139, 141, 143 |
| SC28C11 | TAF2K | Forward | GGTTGGTTTTTAGTTGGTTATATTA | CCCGAACTCTGTCCGCTGAATTCAC | TGGAGGAGGTGCAGAAGGTGG | 144, 146, 148 |
|  |  | Reverse | CTACTAACTTACCCTCCTATAATCC | AGCCGGCAGGACGCTGTGAGT | TCCTTGGGTCCTTTCGAATCA | 145, 147, 149 |
| SC12E1 | IER-3 | Forward | GTGATTTTTYGTATTTTTAAGAAGAA | CTGGCGACCGAACAGAGACTGC | GCCCCTAACGCGCATCCCTG | 150, 152, 154 |
|  |  | Reverse | AACCTAACCCCAACTAAACTATACC | TTGGGCGGGTCCTTCTAACTC | TCTCTGTGCGCCTCGGTCCG | 151, 153, 155 |
| SC13E11 | TIGA1 | Forward | TTTGGGTTTTTTGGGATG | CAGGGCCTGGAGCATAGTAAG | GCATTGTGGGACGGAAGC | 156, 158, 160 |
|  |  | Reverse | TATCTAAAAACTTCCTAACATAATC | CAGTGAGGGAGGACCGAGGG | AACTCCCTGGCATAGTCGATG | 157, 159, 161 |
| SC13C2 | Predicted | Forward | GATTTTTGTAATTAGGTTTGTATGTGT | GCCTGATCCAGCGCGATTG | GTTTTCGGGTCGTCATGGCTG | 162, 164, 166 |
|  |  | Reverse | AATTTCCACTCYCCTATCATACATAC | GGCTGCCCGAGAAGGTAGGAG | TTTCATCTGGTGGCCCTAGCG | 163, 165, 167 |
| SC10B6 | MDS1 | Forward | ATTTTTTTGGTGTTTTTGATG | ACAAGCTTGTTGGCGATCCTA | ATCCAGACCTTGAAAGTCGCT | 168, 170, 172 |
|  |  | Reverse | CCTACCATAAAAATAAAATCACCA | AGTTTGGACACCTTCGCAC | CAAGTAATCTGGGAACCGAT | 169, 171, 173 |
| SC69A9 | UNG2 | Forward | TGTAAGTTGTTTAGTTGGTTGAT | TCCAGTTTCCATTGCGTTTCT | TCCAGTTTCCATTGCGTTTCT | 174, 176, 178 |
|  |  | Reverse | ATAAATTCTAAAAACCCAACACTA | CAGGCACAGCGACTCGAA | CAGGCACAGCGACTCGAA | 175, 177, 179 |
| Control | GTF2H4 | Forward | TCAATCTCCAGGAGCCAATG | TTTGTAGTTCAGACGCGCTTCA | ATTAAGCGACGGCCCGAGAC | 180, 182, 184 |
|  |  | Reverse | CTATCTCTTAACCCACTTCTACTA | CATTGGCTCCTGGAGATTGA | CCAGAAAGAGCATCCGCATCA | 181, 183, 185 |
| Control | FLJ31996 | Forward | GTATTGAGTAGTTTTATTAYGGAGT | CTCAGGGCGCTCTAGTCAAAT | TTGCGGCTCCGTGGTG | 186, 188, 190 |
|  |  | Reverse | AAAACAACTATCACTAAAACCCCT | GGAGCCGCAAGTAACGACA | GGTTTCGGCCAGTGTTGACAT | 187, 189, 191 |
| Control | β-Actin | Forward | — | — | GGATTCCTATGTGGGCGACGAG | 192 |
|  |  | Reverse |  |  | CGCAGCTCATTGTAGAAGGTGTGG | 193 |

(R = mixture of A and G; Y = mixture of G and T)

histone hyperacetylation of a locus that was not hypermethylated in untreated CP70 cells (FIG. 19B, lower panels).

Figure 20:
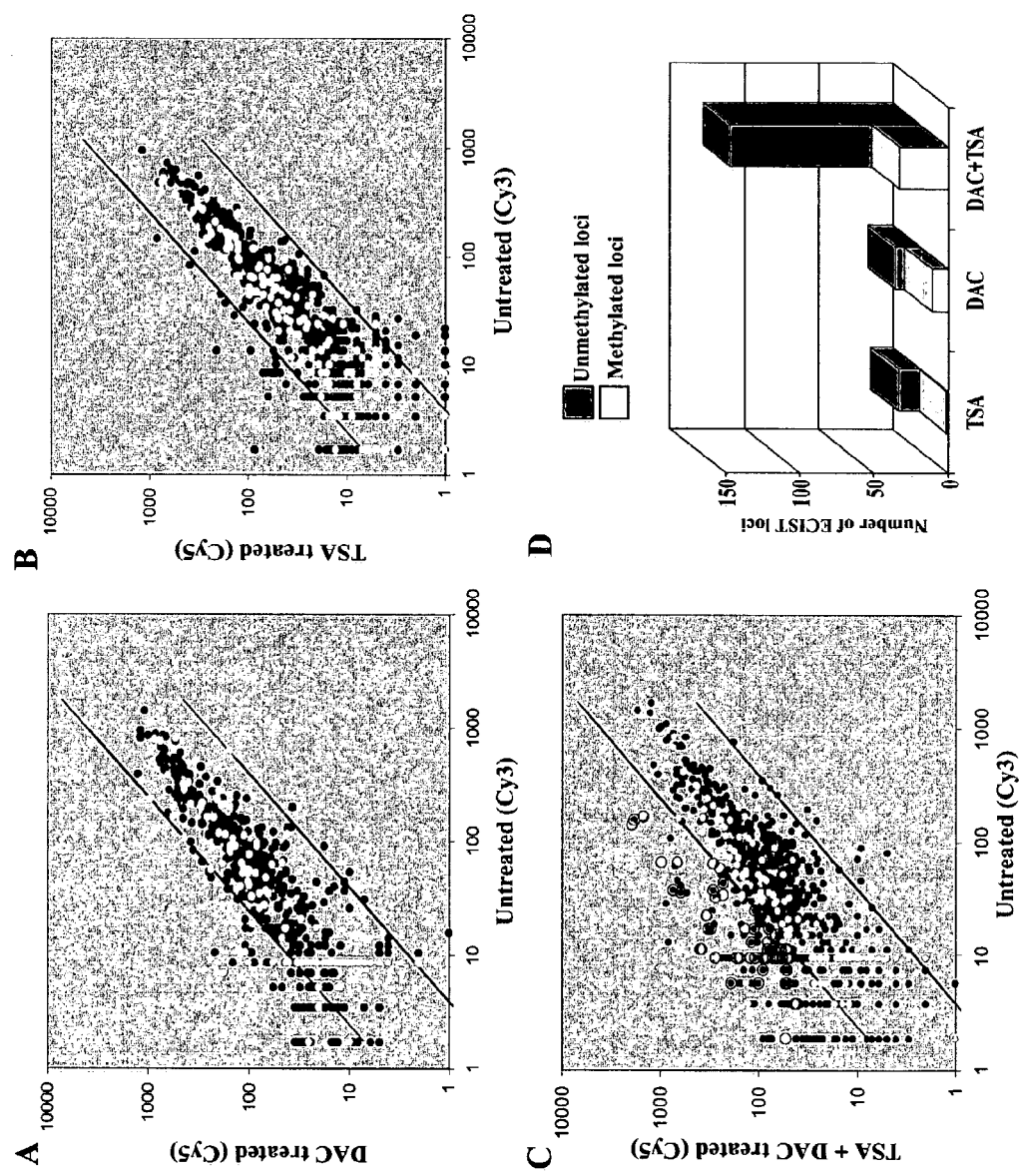
FIGS. 20A, B and C show scatter plots of the inventive triple analysis in CP70 cells using an ECIST microarray panel. Microarray hybridization was conducted as described herein below, under EXAMPLE 13. Cy5:Cy3 ratios of ≧4 (red line) or ≦0.25 (green line) were used to identify up- or down-regulated genes, respectively, in response to epigenetic treatments. Yellow and blue spots depict hypermethylated and unmethylated loci, respectively, in CP70 cells. Red circles indicate hyperacetylated ECIST loci identified by microarray analysis.
FIG. 20D shows the total number of up-regulated ECIST loci in response to various epigenetic treatments.

The total number of ECISTs up-regulated 4-fold or greater by epigenetic treatments was determined. Treatment with DAC or TSA alone resulted in up-regulation of 29 (1.9% of 1507 loci) or 17 (1.1%) loci, respectively. However, a greater number of genes (150 or 10.4%; P<0.001 versus either treatment alone) was up-regulated after the combined treatment (FIGS. 20A, B, and C). The epigenetic treatments also resulted in down-regulation of a few ECIST loci ($\leq 0.25$-fold). Histone hyperacetylation was measured in the combined treatment and scored when a locus showed a normalized Cy5/Cy3 ratio 2-fold greater in the treated cells than that of untreated cells (Weinmann et al., *Genes Dev.* 16:235-244, 2002). Using this cutoff, hyperacetylated loci (red circles in FIG. 20C) were detected in 3.6% (55/1,507) of the ECISTs examined.

To identify hypermethylated ECISTs, a normalized Cy5/Cy3 ratio $\geq 1.5$ relative to the control was used. This cutoff ratio was used previously by applicants to reliably identify hypermethylated CpG islands in various cancers (Yan et al., *Cancer Res.* 61:8375-8380, 2001; Wei et al., *Clin. Cancer Res.* 8:2246-2252, 2002; and Yan et al., *Methods* 27:162-169, 2002. The genes up-regulated by the combined treatment of DAC plus TSA were further divided into two groups (FIG. 20D): hypermethylated (Group 1, yellow spots; and see Table IV) and no detectable methylation (Group 2, blue spots; and see Table V). As shown in FIG. 20C, up-regulation of Group 1 (hypermethylated) loci is more closely associated with histone hyperacetylation than that of Group 2 (not hypermethylated) loci (64%; 22 of 34 loci versus 28%; 33 of 116 loci).

TABLE IV

List of methylation-dependent genes up-regulated by epigenetic treatments

| Clone | Chromosome | Gene Bank | Gene Name | Description | Location |
|---|---|---|---|---|---|
| CpG17E7[a] | 11p15 | NM_013250 | ZNF215 | Novel imprinted zinc finger protein 215 | Promoter & 1st exon |
| CpG18A11[a] | 11q24 | NM_001274 | CHEK1 | CHK1 checkpoint homologue (*S. pombe*) | Promoter & 1st exon |
| CpG18G8[a] | 19p12 | NM_138330 | TIZ | TRAF6-binding zinc finger protein | Promoter & 1st exon |
| CpG21B1[a] | 1q32 | NM_015434 | DKFZP434B168 | DKFZP434B168 protein | Promoter & 1st exon |
| CpG27E8[a] | 19q13 | AK023102 | FLJ13040 | Hypothetical protein FLJ13040 | First exon |
| CpG42E10 | 18p11 | ND[b] | Predicted gene | Twinscan gene predictions | First exon |
| CpG5B6[a] | 12q13 | NM_000785 | CYP27B1 | Cytochrome P450, subfamily XXVIIB | Promoter & 1st exon |
| CpG6B6[a] | 20p12 | AL137678 | vyto | SEL1L homologue | Promoter & 1st exon |
| CpG79F12[a] | 15q25 | AL110434 | EST | Function unknown | ND[b] |
| MP2D2[a] | 2p14 | ND[b] | ND[b] | Genscan gene predictions | ND[b] |
| MP3F2 | 19p13 | X06581 | ERCC-1 | DNA excision repair protein | Promoter |
| SC11E2[a] | 19p13 | ND[b] | ND[b] | No gene identified in this region | ND[b] |
| SC11H10 | 1q22 | NM_032323 | MGC13102 | Hypothetical protein MGC13102 | Exon 3 |
| SC15E7[a] | 14q23 | ND[b] | Predicted gene | Genscan gene predictions | Promoter & 1st exon |
| SCI5H6[a] | 6p21 | NM_021058 | H2BFR | H2B histone family, member R | First exon |
| SC18E9 | 19p13 | X06581 | ERCC-1 | DNA excision repair protein | Promoter |
| SC18F11[a] | 12p13 | ND[b] | Predicted gene | Genscan gene predictions | ND[b] |
| SC18C9 | 3q21 | B1833804 | Seefor | β-1,4 mannosyltransferase homologue | Exon 5 |
| SC19F1[a] | 1q23 | AB029012 | KIAA1089 | Hypothetical protein KIAA1089 | Promoter & 1st exon |
| SC21G11[a] | 14q23 | NM_021979 | HSPA2 | Heat shock 70 kD protein 2 | First exon |
| SC23B1 | 11q13 | B1085096 | Reemay | β-1,4 mannosyltransferase homologue | Exon 3 |
| SC26B7[a] | 8p23 | R18473 | EST | Function unknown | ND[b] |
| SC2A2 | Xq13 | ND[b] | ND[b] | No gene identified in this region | ND[b] |
| SC33C8[a] | 2p23 | NM_024322 | MGC11266 | Hypothetical protein MGC11266 | Promoter & 1st exon |
| SC40C8[a] | 6p22 | NM_003522 | H2BFG | H2B histone family, member G | Promoter & 1st exon |
| SC4H4[a] | 6p21 | NM_002121 | HLA-DPB1 | Major histocompatibility complex, class II, DP | Promoter & 1st exon |
| SC5A4[a] | 8q21 | ND[b] | Sneyly | Acembly gene predictions | First exon |
| SC5D3 | 15q22 | NM_032857 | MRPL56 | β-Lactamase | Promoter & 1st exon |
| SC74D2 | 10q24 | BG208726 | Kloymy | Acembly gene predictions | Promoter & 1st exon |
| SC7B11[a] | 19q13 | BE646494 | Sposee | Acembly gene predictions | Promoter & 1st exon |
| SC87F10[a] | 1p36 | NM_001412 | EIF1A | Eukaryotic translation initiation factor 4C | Promoter & 1st exon |
| SC89F2 | 6q13 | NM_018665 | HAGE | DEAD-box protein | Promoter & 1st exon |
| SC89G2 | 6q13 | NM_018665 | HAGE | DEAD-box protein | Promoter & 1st exon |
| SC8A10 | 19q13 | X06581 | ERCC-1 | DNA excision repair protein | Promoter |

[a]Hyperacetylated histones detected based on microarray analysis (see detail in the text);
[b]Not determined.

TABLE V

List of methylation-independent genes up-regulated by epigenetic treatments

| Clone Name | Chromosome | Gene Bank | Gene Name | Description | Location |
|---|---|---|---|---|---|
| CpG10D4 | 4q34 | ND[b] | ND[b] | No gene identified in this region | ND[b] |
| CpG11D4 | 14q31 | ND[b] | ND[b] | No gene identified in this region | ND[b] |
| CpG11G12 | 19q13 | B1194899 | ND[b] | EST sequence | ND[b] |
| CpG11H5[a] | 11q12 | NM_022830 | FLJ22347 | Hypothetical protein FLJ22347 | Promoter & 1st exon |

TABLE V-continued

List of methylation-independent genes up-regulated by epigenetic treatments

| Clone Name | Chromo-some | Gene Bank | Gene Name | Description | Location |
|---|---|---|---|---|---|
| CpG12E10[a] | 20p13 | X17567 | snRNP B | snRNP B protein | Promoter |
| CpG12F10[a] | 19q13 | NM_013362 | ZNF225 | Zinc finger protein 225 | Promoter & 1st exon |
| CpG13E10 | 16q24 | AK056131.1 | MGC13198 | Hypothetical protein MGC 13198 | Promoter & 1st exon |
| CpG13F10 | 16q22 | NM_014062 | ART-4 | ART-A protein | Promoter & 1st exon |
| CpG14B4 | 6p22.2 | NM_003543 | H4FH | H4 histone family, member H | First exon |
| CpG14F10 | 8q11 | X74794 | MCM4 | Maintenance deficient 4 homologue protein | Promoter & 1st exon |
| CpG15A3 | 18p11 | ND[b] | ND[b] | No gene identified in this region | ND[b] |
| CpG15B4 | 6p22 | NM_003543 | H4FH | H4 histone family, member H | First exon |
| CpG15F10[a] | ND[b] | ND[b] | ND[b] | Sequence not determined | ND[b] |
| CpG18G1 | 10q11 | ND[b] | ND[b] | No gene identified in this region | ND[b] |
| CpG27E3[a] | 19q13 | ND[b] | ND[b] | FGENESH Gene Predictions (C19001774) | Promoter & 1st exon |
| CpG28H8 | ND[b] | ND[b] | ND[b] | No matched sequence | ND[b] |
| CpG32G1 | 1q21 | NM_003528 | H2BFQ | H2B histone family, member Q | Promoter & 1st exon |
| CpG32H5 | 22q12 | ND[b] | ND[b] | FGENESH Gene Predictions (C22000342) | Promoter & 1st exon |
| CpG42B6 | ND[b] | ND[b] | ND[b] | Sequence not determined | ND[b] |
| CpG42B7 | 7q33 | NM_033139 | CALD1 | Caldeson 1 transcript variant 4 | Promoter & 1st exon |
| CpG64A4 | 19q13 | NM_002287 | LAIR1 | Leukocyte-associated Ig-like receptor 1, isoform | Second intron |
| CpG64F10 | 21q21 | AF142099.1 | ADAMTS5 | Disintegrin-like and metalloprotease | Promoter & 1st exon |
| CpG66A4 | 6p22 | NM_003543 | H4FH | H4 histone family, member H | First exon |
| CpG67D1 | 10q25 | ND[b] | ND[b] | No gene identified in this region | ND[b] |
| CpG6E6 | 17p11 | BC020774 | GNG2 | Guanine nucleotide binding protein (G protein) | Promoter & 1st exon |
| CpG71A6 | 3q25 | NM_022736 | FLJ14153 | Hypothetical protein FLJ14153 | ND[b] |
| CpG79B10[a] | 7p22 | ND[b] | ND[b] | No gene identified in this region | ND[b] |
| CpG79H5 | 5q13 | ND[b] | ND[b] | No gene identified in this region | ND[b] |
| CpG7A11 | 2q13 | NM_019014 | Rpol-2 | Similar to DNA-directed RNA polymerase I | Promoter & 1st exon |
| CpG7B6[a] | 2q37 | ND[b] | Predicted gene | Genscan gene predictions | ND[b] |
| DL2C8 | 4q34 | ND[b] | ND[b] | No gene identified in this region | ND[b] |
| DL3D1[a] | 11q12 | AK001301.1 | FLJ10439 | Hypothetical protein FLJ10439 | Promoter |
| DL3D6 | 7q33 | AK056225 | FLJ31663 | cDNA FLJ31663, similar to myotrophin | Promoter & 1st exon |
| DL3G3[a] | 19p13 | NM_021235 | EPS15R | Epidermal growth factor receptor substrate | Promoter & 1st exon |
| MP1A9[a] | 11q23 | NM_000615 | NCAM1 | Neural cell adhesion molecule 1 | Promoter & 1st exon |
| MP1G1[a] | 2q31 | AB046824. | KIAA1604 | Hypothetic protein KIAA1604 | First exon |
| MP2A6[a] | ND[b] | ND[b] | ND[b] | Sequence not determined | ND[b] |
| MP2B9 | 6p21 | NM_021064 | H2AFP | H2A histone family, member P | Promoter & tst exon |
| MP2G7[a] | 20q13 | NM_007019 | UBE2C | Ubiquitin carrier protein E2-C | Promoter & 1st exon |
| MP2G9 | 7q36 | ND[b] | ND[b] | No gene identified in this region | ND[b] |
| MP2H11[a] | 2p14 | ND[b] | Predicted gene | Twinsean gene predictions | ND[b] |
| MP3B9 | 7p22 | ND[b] | ND[b] | No gene identified in this region | ND[b] |
| MP3E5[a] | 3q23 | AB002330 | KIAA0332 | Human mRNA for KIAA0332 gene | Promoter & tst exon |
| PY1B11[a] | 15q15 | BQ417318 | Reepor | Acembly gene predictions | First exon |
| PY1E1[a] | 1q21 | NM_003548 | H4F2 | Histone H4 family 2 | Promoter & 1st exon |
| PY1F6 | 20p12 | AK055700.1 | C20orf30 | Chromosome 20 open reading frame 30 | Promoter & 1st exon |
| SC10B6[a] | 3q26 | NM_004991 | MDS1 | Myelodysplasia syndrome protein 1 | Exon 2 |
| SC10H3[a] | ND[b] | ND[b] | ND[b] | Sequence not determined | ND[b] |
| SC10H6 | 15q14 | AB011132 | KIAA0560 | KIAA0560 protein | Promoter& istexon |
| SC10H9 | 4q34 | ND[b] | ND[b] | No gene identified in this region | ND[b] |
| SC11D12 | ND[b] | ND[b] | ND[b] | Sequence not determined | ND[b] |
| SC12B7 | 7p15 | NM_006547 | KOC1 | IGF-II mRNA-binding protein 3 | Promoter & 1st exon |
| SC12E1 | 6p21 | NM_003897 | IER3 | Immediate early response 3, isoform | Promoter & 1st exon |
| SC13C2[a] | 2p23 | BC015430 | Predicted gene | Similar to transcription factor AKNA | Promoter & tst exon |
| SC13E11 | 5q22 | NM_053000 | TIGAl | TIGAl | Promoter & 1st exon |
| SC14F1 | ND[b] | ND[b] | ND[b] | No gene identified in this region | ND[b] |
| SC15A10[a] | 10q22 | ND[b] | Predicted gene | Twinscan gene predictions | ND[b] |
| SC15A8[a] | 7pl4 | AA478133 | Beyku | Acembly gene predictions | Promoter & 1st exon |
| SC15E3 | Xq26 | NM_006649 | SDCCAG16 | Serologically defined colon cancer antigen 16 | Promoter & 1st exon |
| SC17A9 | 4q31 | ND[b] | ND[b] | No gene identified in this region | ND[b] |
| SC17C6 | 14q23 | ND[b] | ND[b] | No gene identified in this region | ND[b] |
| SC18B4 | ND[b] | ND[b] | ND[b] | Sequence not determined | ND[b] |
| SC18E10 | 10p15 | ND[b] | ND[b] | No gene identified in this region | ND[b] |
| SC18E11 | 17p12 | ND[b] | Predicted gene | Gensc an gene predictions | ND[b] |
| SC18E12 | ND[b] | ND[b] | ND[b] | No gene identified in this region | ND[b] |

TABLE V-continued

List of methylation-independent genes up-regulated by epigenetic treatments

| Clone Name | Chromosome | Gene Bank | Gene Name | Description | Location |
|---|---|---|---|---|---|
| SC18H8 | 20q11 | AF287265 | HCA90 | Hepatocellular carcinoma-associated antigen 90 | Promoter & 1st exon |
| SC19D7 | 6q23 | AA360824.1 | KIAA1798 | Hypothetical protein KIAA 1798 | Promoter & tst exon |
| SC19F4 | ND[b] | ND[b] | ND[b] | Sequence not determined | ND[b] |
| SC22B8 | 1p31 | AI435457.1 | FOXD3.e | Forkhead box D3 transcript e | Promoter & 1st exon |
| SC22C6 | 19p13 | ND[b] | ND[b] | No gene identified in this region | ND[b] |
| SC28C11 | 1p13 | NM_005645 | TAF2K | TATA box binding protein (TBP)-associated | Promoter & 1st exon |
| SC29B12 | 1q21 | NM_003557 | PIP5KJA | Phosphatidylinositol-4-phosphate 5-kinase | Promoter & 1st exon |
| SC29G3 | 1q32 | AL52622 1.1 | TatD-Dnase | Acembly gene predictions | Promoter & 1st exon |
| SC2F9[a] | 4q34 | ND[b] | ND[b] | No gene identified in this region | ND[b] |
| SC37C8 | ND[b] | ND[b] | ND[b] | Sequence not determined | ND[b] |
| SC37H3[a] | 19q13 | AB028987.2 | C19orf7 | Chromosome 19 open reading frame 7 | First intron |
| SC40H2 | 5q11 | NM_021147 | UNG2 | Uracil-DNA glycosylase 2 | Promoter & 1st exon |
| SC41C2 | 1q21 | NM_003557 | PIP5K1A | Phosphatidylinositol-4-phosphate 5-kinase | First exon |
| SC41D5 | 7p15 | AI347402 | EST | Function unknown | ND[b] |
| SC4A11 | 19q13 | NM_015953 | NOSIP | eNOS interacting protein | Promoter & 1st exon |
| SC4B5 | ND[b] | ND[b] | ND[b] | Sequence not determined | NT[b] |
| SC4G5[a] | 7q33 | NM_145808 | L0C136319 | Granule cell differentiation protein | Promoter & 1st exon |
| SC4H11[a] | 11q24 | ND[b] | ND[b] | No gene identified in this region | ND[b] |
| SC5C5 | 7q11 | BE258578. | Glojoy | Acembly gene predictions | Promoter & 1st exon |
| SC62F2[a] | 5q14 | ND[b] | ND[b] | No gene identified in this region | ND[b] |
| SC66A7 | 6p22 | NM_003537 | H3FL | H3 histone family, member L | Promoter & 1st exon |
| SC69A9[a] | 5q11 | NM_021147 | UNG2 | Uracil-DNA glycosylase 2 | Promoter & 1st exon |
| SC71B6[a] | 20q11 | AK027550.1 | ZNF341e | Zinc finger protein 341 transcript 2 | First intron |
| SC71E3 | 1q25 | NM_032678 | MGC3413 | Hypothetical protein MGC3413 | First exon |
| SC71G10 | 19q13 | AK024429 | RhoGEF.16 | Acembly gene predictions | Promoter |
| SC73E9 | 7p14 | ND[b] | Predicted gene | Genscan gene predictions | Exon 3 |
| SC73G5[a] | 6p21 | BC000893 | H2BFA | H2B histone family, member A | Promoter & 1st exon |
| SC74C3 | 10p11 | ND[b] | ND[b] | No gene identified in this region | ND[b] |
| SC76D1 | 7p22 | B1085096 | spoyka | Acembly gene predictions | Promoter & 1st exon |
| SC76H9 | 19q13 | A1571106.1 | DDX34 | DEAD/H (Asp-Glu-Ala-Asp/His) box polypeptide | Promoter & 1st exon |
| SC77F2 | ND[b] | ND[b] | ND[b] | Sequence not determined | ND[b] |
| SC77F4[a] | 4q13 | ND[b] | Predicted gene | Genscan gene predictions | ND[b] |
| SC77H8 | 8p22 | NM_006094 | DLC1 | Deleted in liver cancer 1 | First exon |
| SC78C2 | 2q37 | AI208033.1 | Dudor | Acembly gene predictions | Exons 1 & 2 |
| SC78D5 | 1p35 | NM_001703 | BA12 | Brain-specific angiogenesis inhibitor 2 | Promoter |
| SC7E12[a] | 17p11 | ND[b] | ND[b] | No gene identified in this region | ND[b] |
| SC7H5[a] | 3p14 | BC003364.1 | ARF4 | ADP-rihosylation factor 4. | Promoter & 1st exon |
| SC86B10 | 3p13 | BI196363.1 | Glorfy | Acembly gene predictions | Exon 2 |
| SC86B2 | 4q34 | ND[b] | ND[b] | No gene identified in this region | ND[b] |
| SC86B9 | 6q13 | NM_133645 | MTO1 | MTOl protein isoform IV | Promoter & 1st exon |
| SC86G9 | 6q13 | NM_012123 | CGI-02 | CGI-02 protein | Promoter & 1st exon |
| SC87G12 | 11q13 | NM_053056 | CCND1 | Cyclin D1 | Promoter& 1st exon |
| SC88C10 | ND[b] | ND[b] | Predicted gene | Genscan gene predictions | ND[b] |
| SC88C8 | 12p13 | BG940697 | EST | Function unknown | ND[b] |
| SC88E12 | 12q13 | NM_005371 | MEITL1 | Methyltransferase-like protein 1, isoform a | Promoter & 1stexon |
| SC89A10 | 17q21 | AK056941 | FLJ32379 | Polyprotein homologue | Promoter & 1st exon |
| SC89H7 | 12q23 | AK001250.1 | FLJ100388 | Hypothetical protein FLJ10388 , RNA polymera | First intron |
| SC8D1 | 14q23 | NM_002788 | PSMA3 | Proteasome (prosome, macropain) subunit, alpgha | First exon |
| SC90B1 | 12p13 | NM_000719 | CACNA1C | Caclium Channel, voltage-dependent, L type, | Exon 7 |
| SC90B12 | 7p15 | NM_006547 | KOC1 | IGF-II mRNA-binding protein 3 | Promoter & 1st exon |
| SC90F10 | 9p23 | ND[b] | Predicted gene | Genscan gene predictions | ND[b] |

Up-regulation of Methylation-Silenced Genes in Response to Epigenetic Treatments. Within Group 1 genes, increased expression of only a few loci (n=11) was observed after treatment with DAC alone; however, the combined treatment of DAC and TSA resulted in up-regulation of 34 loci (FIG. 20D). No significant change in expression of Group 1 genes was seen in CP70 cells treated with TSA alone (FIG. 20D).

Figure 21:
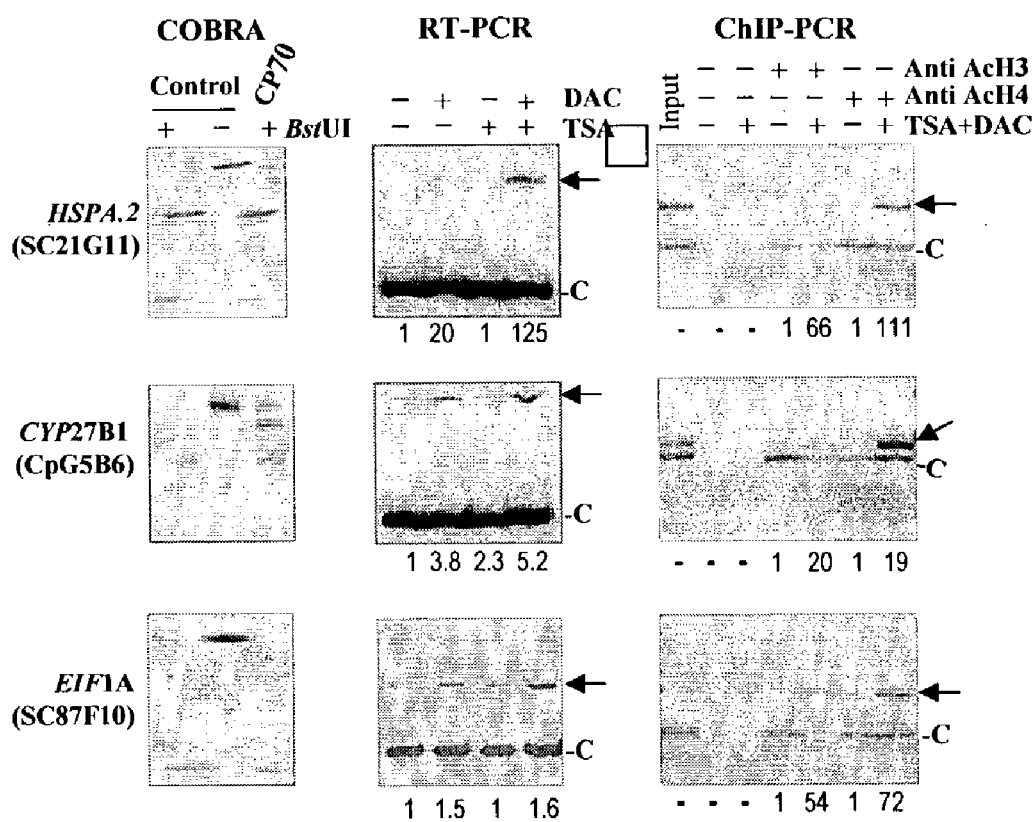
FIG. 21 shows a 'triple analysis' analysis, according to the present invention, of DNA methylation, gene expression, and histone acetylation in methylation-dependent ECIST loci in ovarian cancer cell line CP70 (gene names are shown at left). These results that the concerted action of DNA demethylation and histone hyperacetylation results in synergistic re-expression of methylation-silenced genes.

Three gene loci from Group 1 (HSPA.2, CYP27B1, and EIF1A) were further analyzed to confirm the microarray findings. FIG. 21 shows an analysis, according to the present invention, of DNA methylation, gene expression, and histone acetylation in methylation-dependent ECIST loci in ovarian cancer cell line CP70 (gene names are shown at left). Methylation analysis: COBRA (combined bisulfite restriction analysis) was used to determine the methylation status of ECIST loci. Briefly, genomic DNA (2 µg) was bisulfite-treated and subjected to PCR using primers flanking the interrogating BstUI site(s) in each ECIST locus. $^{32}$P-labeled products were digested with BstUI and separated on 8% polyacrylamide gels. As shown, the digested fragments reflect BstUI methylation within a CpG island. Control DNA was methylated in vitro with the SSI methylase. The symbol "+" refers to treatment with BstUI digestion, whereas the symbol "−" refers to assays without BstUI digestion. For expression analysis, total RNA (2 µg) was isolated from treated (+) or untreated (−) CP70 cells and used to generate cDNA for RT-PCR. "DAC" refers to 5-aza-2'-deoxycytidine, whereas "TSA" refers to trichostatin A. The arrows indicate positions of amplified fragments. The level of each ECIST expression was compared to that of β-actin (marked by "C"). For acetylation analysis, chromatin DNA was immunoprecipitated with anti-acetylated histone 3 (Anti AcH3) or 4 (Anti AcH4) and subjected to PCR using primers located at the 5'-ends of a test gene. The arrows indicate positions of amplified products. The level of histone acetylation for an ECIST locus was compared to that of a control locus "C" (either GTF2H4 or FLJ31996).

As shown in FIG. 21, hypermethylation of the HSPA.2 CpG island in CP70 cells was confirmed using COBRA (FIG. 21, row 1, left panel), and no expression of HSPA.2 was detected in untreated CP70 cells using RT-PCR (FIG. 21, row 1, middle panel). However, HSPA.2 expression was increased by DAC treatment, remained unchanged after treatment with TSA alone, and was markedly increased by the combined treatment of DAC and TSA (FIG. 21, row 1, middle panel). Furthermore, after treatment of CP70 cells with DAC plus TSA, histones H3 and H4 in the promoter region of HSPA.2 were determined to be hyperacetylated using ChIP-PCR (FIG. 21, row 1, right panel). These results are consistent with previous reports (Suzuki et al., *Nature Genet.* 31:141-149, 2002; Cameron et al., *Nature Genet.* 21:103-107, 1999) that the concerted action of DNA demethylation and histone hyperacetylation results in synergistic re-expression of methylation-silenced genes.

In untreated CP70 cells, partial methylation of the CYP27B1 CpG island was observed and expression of CYP27B1 was low; however, treatment of CP70 cells with DAC plus TSA resulted in histone hyperacetylation and increased expression of CYP27B1 (FIG. 21, row 2). In contrast, and despite the strong hyperacetylation observed at the EIF1A locus, expression of EIF1A remained largely unaffected by the epigenetic treatments (FIG. 21, row 3). The EIF1A locus we identified, located on human chromosome 1 (Dever et al., *J. Biol. Chem.* 269:3212-3218, 1994), was determined to be hypermethylated in CP70 cells by using COBRA. It has been reported that multiple copies of EIF1A exist at different chromosomal regions, e.g., chromosomes X and Y (Lahn & Page, *Science (Wash. DC)* 278:675-680, 1997), and it is reasonably likely that one or more of these loci remain unmethylated, and thus contribute to the significant basal expression of EIF1A detected by RT-PCR (FIG. 21, row 3).

Up-regulation of Methylation-Independent Genes in Response to Epigenetic Treatments. With respect to Group 2 genes, a total of 116 loci were up-regulated (≧4-fold) by the epigenetic treatments (FIG. 20C, blue spots; and FIG. 20D), but expression of these loci appeared to be unrelated to DNA methylation. From this group, for example, eight loci were further analyzed using COBRA, RT-PCR and ChIP-PCR (FIGS. 22A and 22B).

Figures 22A, 22B:
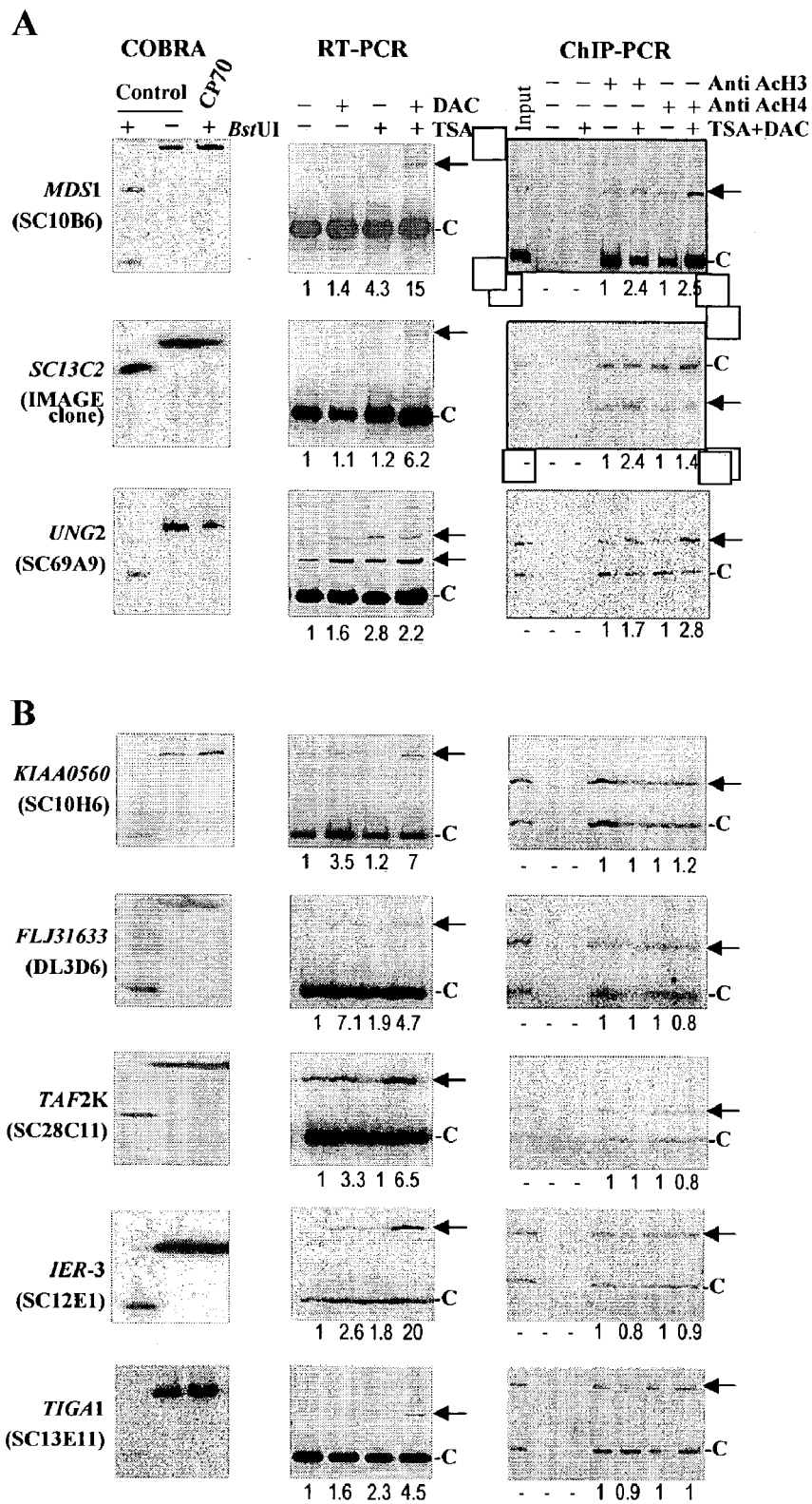
FIGS. 22A and 22B show 'triple analyses' of Group 2a ECIST loci (22A: methylation-independent and histone acetylation-enhanced) and Group 2b loci (22B: methylation- and histone acetylation-independent), respectively (see EXAMPLE 13, under "Results" for definition of Groups 2a and 2b). The eight representative loci of FIGS. 22A and 22B were unmethylated in CP70 cells, and expression of these loci was low or absent in untreated CP70 cells. Increased expression of some of these loci was observed after treatment with DAC or TSA alone. The combined treatment induced expression of all eight loci, but histone hyperacetylation was seen in only the promoter regions of MDS1, SC13C2, and UNG2 (FIG. 22A).

For FIGS. 22A and 22B, methylation analysis, COBRA (combined bisulfite restriction analysis), was used to determine the methylation status of ECIST loci in ovarian cancer cell line CP70 (gene names are shown at left). Genomic DNA (2 µg) was bisulfite-treated and subjected to PCR using primers flanking the interrogating BstUI site(s) in each ECIST locus. $^{32}$P-labeled products were digested with BstUI and separated on 8% polyacrylamide gels. As shown, the digested fragments reflect BstUI methylation within a CpG island. Control DNA was methylated in vitro with the SSI methylase. +: BstUI digestion; −: without BstUI digestion. Expression analysis: total RNA (2 µg) isolated from treated (+) or untreated (−) CP70 cells was used to generate cDNA for RT-PCR. DAC, 5-aza-2'-deoxycytidine; TSA, trichostatin A. Arrows indicate the positions of amplified fragments. The level of each ECIST expression was compared to that of β-actin (marked by C). Acetylation analysis: CP70 cells were treated with DAC plus TSA (+) or untreated (−). Chromatin DNA was then immunoprecipitated with (+) or without (−) anti-acetylated histone 3 (Anti AcH3) or 4 (Anti AcH4) and subjected to PCR using primers located at the 5-ends of a test gene. Arrows indicate the positions of amplified products. The level of histone acetylation for an ECIST locus was compared to that of a control locus "C" (either GTF2H4 or FLJ31996).

With respect to FIGS. 22A and 22B, the eight loci were unmethylated in CP70 cells, and expression of these loci was low or absent in untreated CP70 cells. Increased expression of some of these loci was observed after treatment with DAC or TSA alone. The combined treatment induced expression of all eight loci, but histone hyperacetylation was seen in only the promoter regions of MDS1, SC13C2, and UNG2 (FIG. 22A). Based on the response of these eight loci to the epigenetic treatments, we further sub-divided the methylation-independent loci into two subgroups: subgroup 2a, methylation-independent, histone acetylation-enhanced genes (n=33) and subgroup 2b, methylation- and histone acetylation-independent genes (n=83).

Summary of Example 13

An integrated 'triple' microarray system that combines parallel analysis of gene expression, DNA methylation, and DNA-protein interactions was developed to further define epigenetic modifications and the order of epigenomic events at CpG islands on a global scale. This is a novel genomic approach and method for dissecting the complex hierarchy of transcriptional controls orchestrated by the epigenomic machinery. This integrated microarray system allows for both the identification of individual genes and a systematic analysis of the relationship between the epigenetic machinery, promoter targets and downstream responses regulated by the epigenome.

Using the triple analysis approach, both primary and secondary responses to epigenetic factors were identified, and these were further categorized into three groups of genes based on their methylation status: Group 1 (methylation-dependent) and Groups 2a and 2b (methylation-independent). For Group 1 genes, transcriptional silencing is dominated by methylation (FIG. 21). Reactivation of genes silenced by CpG methylation would presumably involve a series of steps, including removal of MBD proteins from demethylated DNA and/or transcriptional repressors that are recruited by MBD proteins (Jones & Baylin, *Nature Rev. Genet.* 3:415-428, 2002). Epigenetic complexes have been shown to possess chromatin-remodeling activity and produce structures refractory to transcriptional activation (Id). Disrupting these complexes would presumably diminish their activity and result in a more open, transcriptionally active chromatin configuration. A physical association between methylated DNAs and deacetylated histones has recently been shown (Robertson et al., *Nucleic Acids Res.* 28:2108-2113), and the synergistic reactivation of methylation-silenced genes (Group 1) achieved herein by the combined treatment supports a mechanism comprising a functional interaction between the epigenetic modifications. Whether this functional relationship is due to a direct or indirect interaction between the molecular targets remains to be elucidated.

The inventive triple array analysis also revealed an effect of the drug treatments on methylation-independent gene expression. Group 2a represents a class of distinct genes with unmethylated promoters whose increased expression is produced by TSA alone or the combined treatment, but not by DAC alone. It is unclear how DAC and TSA act mechanistically on unmethylated promoters, but has been shown that DNA methyltransferase DNMT1 (DNA methyltransferase 1), in the absence of DNA methylation, can directly suppress transcription through actions with histone deacetylases (Suzuki et al., *Nature Genet.* 31:141-149, 2002; Robertson et al., *Nucleic Acids Res.* 28:2108-2113). The present observation that enhanced histone hyperacetylation of MDS1 required both DAC and TSA supports a role for a methylation-independent effect of DNMT1 in ovarian cancer cells. Furthermore, these observations indicate that histone deacetylase activity may play a role in the epigenetic-associated control of Group 2a gene expression.

The majority of genes identified in the present triple array analysis belonged to Group 2b, which showed enhanced expression independent of both DNA demethylation and histone acetylation. Up-regulation of these loci by DAC plus TSA treatments is most likely due to an event downstream of modulations in the epigenetic cascade. There are several possible, but not mutually exclusive, mechanisms that may account for this secondary effect, including increased post-transcriptional processing (RNA stability), reactivation of an upstream transcription factor, or regulation by target genes in an induced signal transduction pathway (Karpf & Jones, *Oncogene,* 21:5496-5503, 2002).

Induction of some of the genes in Group 2 is likely to be associated with cellular responses to drug toxicity or stress, as shown by using microarrays to examine gene expression profiles in DAC-treated human cancer cell lines (Suzuki et al., *Nature Genet.* 31:141-149, 2002; Liang et al., *Cancer Res.,* 62:961-966, 2002; and Milutinovic et al., *J. Biol. Chem.,* 278 (e-publication ahead of print), 2003). Furthermore, many of the stress-response genes induced by DAC show similar early and transient expression characteristics (Milutinovic et al., supra). For example, early induction of the apoptosis promoting factor BIK was observed after DAC treatment of a human lung cancer cell line, and BIK expression returned to control levels by 72 hours after treatment with DAC (Id). Interestingly, the BIK gene, which does not contain a CpG island, is also induced in a methylation-independent manner by TSA (Suzuki et al., supra). In contrast, DAC treatment gradually induces expression of methylation-dependent genes and their downstream targets (Liang et al., supra; Milutinovic et al., supra), and expression of these genes has been shown to be prolonged or increased as demethylation progresses (Liang et al., supra; Milutinovic et al., supra). Significantly, the inventive triple microarray system is well suited for distinguishing early stress-response genes from late genes induced by epigenetic treatments over time.

The present inventive integrated approach is useful for identifying novel therapeutic targets, determining the mechanisms underlying epigenetic gene silencing and the specificity of epigenetic therapies, based on reactivating the expression of methylation-silenced genes in cancer and other diseases.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07563567B1). An electronic copy of the "Sequence Listing" will also be available from the USPTO upon request and payment of the fee set forth in 37 CFR 1.19(b)(3).

The invention claimed is:

1. A high-throughput method for assessing genomic CpG methylation and expression of genomic sequences of a tissue sample, comprising:
   obtaining a microarray, or replicates thereof, having a plurality of affixed CpG-rich genomic probe fragments each comprising a first exon sequence or a detectably hybridizable portion of the first exon sequence of an expressible gene; and
   hybridizing, to the microarray or replicate thereof, CpG-rich genomic DNA-derived target sequences of a tissue sample, and mRNA-derived target sequences having exon 1 sequences of the respective expressible genes of the tissue sample, wherein the DNA-derived target sequences and the mRNA-derived target sequences are detectibly labeled, wherein the extent of said target hybridizations with each such represented expressible gene probe is reflective of the presence of methylated genomic CpG sequences and genomic expression, respectively, in the tissue sample, and whereby both genomic CpG methylation and genomic expression of particular expressible genes represented on the microarray, or replicate thereof, are, at least in part, assessed.

2. The method of claim 1, further comprising hybridization of the microarray or replicate thereof to CpG-rich genomic DNA-derived target sequences of a second tissue sample and to mRNA-derived target sequences of the second tissue sample, wherein the DNA-derived target sequences of the first and second tissue samples are distinguishably labeled and co-hybridized to the microarray or replicate thereof, and wherein the mRNA-derived target sequences of the first and second tissue samples are distinguishably labeled and co-hybridized to the microarray or replicate thereof, and whereby differences, between the tissue samples, in both genomic CpG methylation and genomic expression of particular expressible genes represented on the microarray or replicate thereof, are, at least in part, assessed.

3. The method of claim 2, wherein the first and second tissue samples are different, and correspond to test and control tissue samples.

4. The method of claim 3, wherein the test and control tissue samples correspond to cancer and normal tissue, respectively.

5. The method of claim 2, wherein each of the plurality of affixed CpG-rich genomic probe fragments comprises part of a promoter and first exon of a gene.

6. The method of claim 2, wherein each of the plurality of affixed CpG-rich genomic probe fragments comprises a CpG island sequence, or portion thereof.

7. The method of claim 2, wherein each of the plurality of affixed CpG-rich genomic probe fragments comprises an expressed CpG island sequence tag (ECIST).

8. The method of claim 2, wherein the plurality of affixed CpG-rich genomic probe fragments is derived from a CpG dinucleotide rich genomic library.

9. The method of claim 2, wherein the hybridizable CpG-rich genomic DNA-derived target sequences are prepared by a method comprising amplification of CpG-rich DNA fragments corresponding to genomic DNA sequences having one or more methylated CpG sequences.

10. The method of claim 2, wherein the hybridizable CpG-rich genomic DNA-derived target sequences are prepared by a method comprising use of a methylation-sensitive restriction enzyme.

11. The method of claim 2, wherein preparation of the CpG-rich genomic DNA-derived target sequences and hybridization thereof to the microarray, or to replicates thereof, is performed according to the method of differential methylation hybridization (DMH), comprising the generation of target amplicons corresponding to methylated CpG island loci.

12. The method of claim 2, wherein preparation of the mRNA-derived target sequences comprises at least one of RNA ligase-mediated cDNA synthesis (RLCS), and RT-PCR.

13. The method of claim 2, wherein microarray hybridization to the CpG-rich genomic DNA-derived target sequences and to the mRNA-derived target sequences is sequential, using a single microarray or replicates thereof.

14. The method of claim 2, wherein microarray hybridization to the CpG-rich genomic DNA-derived target sequences and to the mRNA-derived target sequences is performed in parallel, using replicate microarrays.

15. A high-throughput method for assessing genomic CpG methylation and expression of genomic sequences of a tissue sample, comprising:
   a) obtaining, from a tissue sample, genomic DNA and preparing therefrom hybridizable CpG-rich genomic DNA-derived target sequences having a detectable label;
   b) obtaining, from the tissue sample, mRNA and preparing therefrom hybridizable mRNA-derived target sequences having exon 1 sequences of the respective expressible genes and having a detectable label;
   c) hybridizing both the labeled DNA-derived target sequences and the labeled mRNA-derived target sequences to a microarray or replicate thereof having a plurality of affixed CpG-rich genomic probe fragments each comprising a first exon sequence or a detectably hybridizable portion of the first exon sequence of an expressible gene, and wherein the extent of said hybridizations with each such represented expressible gene probe is reflective of the presence of methylated genomic CpG sequences and genomic expression, respectively, in the tissue sample; and
   d) assessing, based at least in part on said hybridizations, both genomic CpG methylation and genomic expression of particular expressible genes represented on the microarray or replicate thereof.

16. The method of claim 15, further comprising preparing, from a second tissue sample, both CpG-rich genomic DNA-derived target sequences and mRNA-derived target sequences, wherein the DNA-derived target sequences of the first and second tissue samples are distinguishably labeled and co-hybridized to the microarray or replicate thereof, and wherein the mRNA-derived target sequences of the first and second tissue samples are distinguishably labeled and co-hybridized to the microarray or replicate thereof, and whereby differences, between the tissue samples, in both genomic CpG methylation and genomic expression of particular expressible genes represented on the microarray or replicate thereof, are, at least in part, assessed.

17. The method of claim 16, wherein the first and second tissue samples are different, and correspond to test and control tissue samples.

18. The method of claim 17, wherein the test and control tissue samples correspond to cancer and normal tissue, respectively.

19. The method of claim 16, wherein each of the plurality of affixed CpG-rich genomic probe fragments comprises part of a promoter and first exon of a gene.

20. The method of claim 16, wherein each of the plurality of affixed CpG-rich genomic probe fragments comprises a CpG island sequence, or portion thereof.

21. The method of claim 16, wherein each of the plurality of affixed CpG-rich genomic probe fragments comprises an expressed CpG island sequence tag (ECIST).

22. The method of claim 16, wherein the plurality of affixed CpG-rich genomic probe fragments is derived from a CpG dinucleotide rich genomic library.

23. The method of claim 16, wherein preparing the hybridizable CpG-rich genomic DNA-derived target sequences comprises amplification of CpG-rich DNA fragments corresponding to genomic DNA sequences having one or more methylated CpG sequences.

24. The method of claim 16, wherein preparing the hybridizable CpG-rich genomic DNA-derived target sequences comprises use of a methylation-sensitive restriction enzyme.

25. The method of claim 16, wherein preparing of the CpG-rich genomic DNA-derived target sequences and hybridization thereof to the microarray or to replicates thereof comprises use of the method of differential methylation hybridization (DMH), comprising the generation of target amplicons corresponding to methylated CpG island loci.

26. The method of claim 16, wherein preparing of the mRNA-derived target sequences comprises at least one of RNA ligase-mediated cDNA synthesis (RLCS), and RT-PCR.

27. The method of claim 16, wherein hybridizing of the CpG-rich genomic DNA-derived target sequences and the mRNA-derived target sequences to the single microarray or replicates thereof is sequential.

28. The method of any one of claims 2 or 16, wherein the first and second tissue samples are identical, and further comprising treating of one of the tissue samples with a demethylating agent prior to preparing CpG-rich genomic DNA-derived target sequences and mRNA-derived target sequences from the treated tissue sample, whereby the effects of the agent on at least one of genomic CpG methylation or genomic expression of particular expressible genes represented on the microarray, or replicates thereof, is, at least in part, assessed, and whereby assessment of gene silencing is afforded.

29. The method of claim 28, wherein the demethylating agent comprises 5-aza-2'-deoxycytidine.

30. The method of claim 16, wherein hybridizing of the CpG-rich genomic DNA-derived target sequences and the mRNA-derived target sequences is performed in parallel, using replicate microarrays.

31. The method of any one of claims 1 or 15, further comprising hybridization of the microarray or replicate thereof, to target sequences derived from acetylated histone-associated DNA of the target tissue, wherein the extent of said histone-associated target sequence hybridization with each represented expressible gene probe is reflective of the presence of gene-associated acetylated histones, and whereby at least one of genomic CpG methylation, genomic expression, or gene-associated acetylated histones of particular expressible genes represented on the microarray, or replicates thereof, is, at least in part, assessed.

32. The method of claim 31, further comprising hybridization of the microarray or replicate thereof, to CpG-rich genomic DNA-derived target sequences of a second tissue sample, to mRNA-derived target sequences of the second tissue sample, and to target sequences derived from acetylated histone-associated DNA of the second target tissue, wherein the respective target sequences of the first and second tissue samples are distinguishably labeled and, in each case, co-hybridized to the microarray or replicate thereof, and whereby differences, between the tissue samples, in at least one of genomic CpG methylation, genomic expression, or gene-associated histone acetylation of particular expressible genes represented on the microarray or replicate thereof, is, at least in part, assessed.

33. The method of claim 32, wherein the first and second tissue samples are identical, and further comprising treating of one of the tissue samples with at least one of a demethylating agent or an inhibitor of a histone deacetylase prior to preparing mRNA-derived target sequences and target sequences derived from acetylated histone-associated DNA from the treated tissue sample, whereby the effects of the agents, alone or in combination, on at least one of genomic CpG methylation, genomic expression, or gene-associated histone acetylation of particular expressible genes represented on the microarray or replicate thereof, is, at least in part, assessed, and whereby assessment of relationships between epigenetic events and gene expression is afforded.

34. The method of claim 33, wherein the demethylating agent is 5-aza-2'-deoxycytidine, and the inhibitor of histone deacetylases is trichostatin A.

35. The method of claim 32, wherein the first and second tissue samples are different, and correspond to test and control tissue samples.

36. The method of claim 35, wherein the test and control tissue samples correspond to cancer and normal tissue, respectively.

37. The method of claim 31, wherein each of the plurality of affixed CpG-rich genomic probe fragments comprises part of a promoter and first exon of a gene.

38. The method of claim 31, wherein each of the plurality of affixed CpG-rich genomic probe fragments comprises a CpG island sequence, or portion thereof.

39. The method of claim 31, wherein each of the plurality of affixed CpG-rich genomic probe fragments comprises an expressed CpG island sequence tag (ECIST).

40. The method of claim 31, wherein the plurality of affixed CpG-rich genomic probe fragments is derived from a CpG dinucleotide rich genomic library.

41. The method of claim 31, wherein the hybridizable CpG-rich genomic DNA-derived target sequences are prepared by a method comprising amplification of CpG-rich DNA fragments corresponding to genomic DNA sequences having one or more methylated CpG sequences.

42. The method of claim 31, wherein the hybridizable CpG-rich genomic DNA-derived target sequences are prepared by a method comprising use of a methylation-sensitive restriction enzyme.

43. The method of claim 31, wherein preparation of the CpG-rich genomic DNA-derived target sequences and hybridization thereof to the microarray, or to replicates thereof, is performed according to the method of differential methylation hybridization (DMH), comprising the generation of target amplicons corresponding to methylated CpG island loci.

44. The method of claim 31, wherein preparation of the mRNA-derived target sequences comprises at least one of RNA ligase-mediated cDNA synthesis (RLCS), and RT-PCR.

45. The method of claim 31, wherein microarray hybridization to the CpG-rich genomic DNA-derived target sequences and to the mRNA-derived target sequences is sequential, using a single microarray or replicates thereof.

46. The method of claim 31, wherein microarray hybridization to the CpG-rich genomic DNA-derived target sequences and to the mRNA-derived target sequences is performed in parallel, using replicate microarrays.

47. The method of claim 31, wherein preparation of the hybridizable target sequences derived from acetylated histone-associated DNA of the target tissue comprises immunoprecipitation using anti-histone antibodies.

\* \* \* \* \*